US007989633B2

(12) United States Patent
Kuhl et al.

(10) Patent No.: US 7,989,633 B2
(45) Date of Patent: Aug. 2, 2011

(54) 4-CHROMENONYL-1,4-DIHYDROPYRIDINES AND THEIR USE

(75) Inventors: Alexander Kuhl, Hagen (DE); Peter Kolkhof, Wuppertal (DE); Heike Heckroth, Odenthal (DE); Karl-Heinz Schlemmer, Wuppertal (DE); Ingo Flamme, Reichshof (DE); Santiago Figueroa Perez, Leverkusen (DE); Heike Gielen-Haertwig, Monheim (DE); Rolf Grosser, Leverkusen (DE); Jens-Kerim Ergüden, Wülfrath (DE); Dieter Lang, Velbert (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 192 days.

(21) Appl. No.: 11/989,277

(22) PCT Filed: Jul. 12, 2006

(86) PCT No.: PCT/EP2006/006809
§ 371 (c)(1),
(2), (4) Date: Sep. 22, 2009

(87) PCT Pub. No.: WO2007/025604
PCT Pub. Date: Mar. 8, 2007

(65) Prior Publication Data
US 2010/0022484 A1 Jan. 28, 2010

(30) Foreign Application Priority Data

Jul. 22, 2005 (DE) .................. 10 2005 034 267

(51) Int. Cl.
*C07D 213/62* (2006.01)
(52) U.S. Cl. ..................................... 546/298
(58) Field of Classification Search ........................ None
See application file for complete search history.

(56) References Cited

U.S. PATENT DOCUMENTS

| 3,775,422 | A | 11/1973 | Bossert et al. |
| 3,862,161 | A | 1/1975 | Bossert et al. |
| 3,966,948 | A | 6/1976 | Bossert et al. |
| 4,540,789 | A | 9/1985 | Goldmann et al. |
| 4,555,512 | A | 11/1985 | Goldmann et al. |
| 4,628,107 | A | 12/1986 | Goldmann et al. |

FOREIGN PATENT DOCUMENTS

| DE | 2003146 A1 | 7/1971 |
| DE | 3311003 A1 | 9/1984 |
| DE | 3311005 A1 | 9/1984 |
| EP | 0223744 | 5/1987 |

OTHER PUBLICATIONS

R. E. Booth et al.: "Aldosterone," Advances in Physiology Education, vol. 26, No. 1, Mar. 2002, pp. 8-20.

B. Pitt et al.: "Eplerenone, A Selective Aldosterone Blocker, in Patients with Left Ventricular Dysfunction after Myocardial Infarction," The New England Journal of Medicine, vol. 348, No. 14, Apr. 3, 2003, pp. 1309-1321.
B. Pitt et al.: "The Effect of Spironolactone on Morbidity and Mortality in Patients with Severe Heart Failure," The New England Journal of Medicine, vol. 341, No. 10, pp. 709-717, 1999.
H. A. Kuhn et al.: Innere Medizin—Ein Lehrbuch fur Studierende der Medizin and Arzte Bergrundet von Ludwig Heilmeyer, Springer-Verlag, Berlin, Heidelberg, New York, 1982.
M. A. Zaman et al.; "Drugs Targeting the Renin-Angiotension-Aldosterone System," Nature Reviews Drug Discovery, vol. 1, Aug. 2002, pp. 621-636.
N. M. Kaplan: "The Current Epidemic of Primary Aldosteronism: Causes and Consequences," Journal of Hypertension, 2004, vol. 22, pp. 863-869.
A. Chiarini et al.: "Negative Inotropic and Chronotropic Activity of Calcium Channel Ligands Possessing a Xanthone 1,4-Dihydropyridine Backbone," Forsch Drug Research, vol. 42, No. 6, 1992, pp. 797-801.
D. M. Stout et al.: "Recent Advances in the Chemistry of Dihydropyridines," Chem. Rev., vol. 82, 1982, pp. 223-243.
H. Meyer et al.: "Dihydropyridniie, II—Synthese von 1,4-Dihydropyridinen mit Bruckenkppf-N-Atom," Liebigs Ann. Chem., 1977, pp. 1888-1894.
H. Meyer et al.: "Synthese von 2-Aminodihydropyridinen durch Michael-Addition," Liebigs Ann. Chem., 1977, pp. 1985-1908.
H. Meyer et al.: :Synthese von 6-Alkoxy-2-Amino-4,5-Dihydropyridin-3,5-Dicarbon-Saureestern, Liebigs Ann. Chem., 1976, pp. 1762-1766.
R. J. Gould et al.: "[$^3$H]Nitrendipine-Labeled Calcium Channels Discriminate Inorganic Calcium Agonists and Antagonists," Proc. Natl. Acad. Sci., vol. 79, Jun. 1982, pp. 3656-3660.
P. Babin: "Nouveau Mode de Cyclisation de Ceto-Ylures. Application a une Synthese Originale D'Acyl-3-Hydroxy-4-Coumarines et de L'Hydroxy-11 Benzo-(b) 12[H] Xanthone-12," Tetradedrno, vol. 37, 1981, pp. 1131-1139.
R. J. Chambers et al.: "Development of 2,2-Dimethylchromanol Cysteinyl $LT_1$ Receptor Antagonists," Bioorganic & Medicinal Chemistry Letters, vol. 8, 1998, pp. 3577-3582.
D. Alker et al.: "Long-Acating Digydropyridine Calcium Antagonists. 9. Structure Activity Relationships around Amlodipine," Eur. J. Med. Chem., vol. 26, 1991, pp. 907-913.
F. J. Ehlert et al.: "The Binding of [$^3$H]Nitrendifine to Receptors for Calcium Channel Antagonists in the Heart, Cerebral Cortex, and Ileum of Rats," Life Sciences, vol. 30, 1982, pp. 2191-2202.
J. I. Ubeda et al.: Synthesis of 6-Formyl Derivatives of 5,8-Dimethoxycarbostyryl,: Heterocycles, vol. 38, No. 12, 1994, pp. 2677-2689.

(Continued)

*Primary Examiner* — Janet L Andres
*Assistant Examiner* — Heide Reese
(74) *Attorney, Agent, or Firm* — Jonathan R. Harris; William F. Gray

(57) ABSTRACT

The present application relates to novel 4-chromenonyl-1,4-dihydropyridines, process for their preparation, their use for the treatment and/or prophylaxis of diseases, and their use for the manufacture of medicaments for the treatment and/or prophylaxis of diseases, especially cardiovascular disorders.

6 Claims, No Drawings

OTHER PUBLICATIONS

H. J. Bestmann et al.: "Chromones from Acylsalicylic Acids," Chemistry Letters, 1983, pp. 997-998.

C. Kashima et al.: "The Alkylation of 3,5-Dimethylisoxazole," Bulletin of the Chemical Society of Japan, vol. 46, No. 1, 1973, pp. 310-313.

S. G. Jagadeesh et al.: "Synthesis of 3-Methylchromone-8-Acetic Acids and 2-Methyl-Chromone-8-Carboxylic Acids," Synthetic Communications, vol. 31, No. 10, 2001, pp. 1547-1557.

Budriesi, et al., 1,4-Dihydropyridine derivatives as calcium channel modulators: the role of 3-methoxy-flavone moiety, Bioorg. Med. Chem., 13(10): 3423-3430 (2005).

4-CHROMENONYL-1,4-DIHYDROPYRIDINES AND THEIR USE

The present application relates to novel 4-chromenonyl-1,4-dihydropyridines, process for their preparation, their use for the treatment and/or prophylaxis of diseases, and their use for the manufacture of medicaments for the treatment and/or prophylaxis of diseases, especially cardiovascular disorders.

Aldosterone plays a key part in maintaining fluid and electrolyte homeostasis by promoting, in the epithelium of the distal nephron, sodium retention and potassium secretion, thus contributing to keeping the extracellular volume constant and thus to regulating blood pressure. Besides this, aldosterone displays direct effects on the structure and function of the cardiac and vascular system, but the underlying mechanisms thereof are not yet fully explained [R. E. Booth, J. P. Johnson, J. D. Stockand, Adv. Physiol. Educ. 26 (1), 8-20 (2002)].

Aldosterone is a steroid hormone which is formed in the adrenal cortex. Its production is regulated indirectly very substantially depending on the renal blood flow. Any decrease in renal blood flow leads to release in the kidney of the enzyme renin into the circulating blood. This in turn activates the formation of angiotensin II, which on the one hand has a constricting effect on the arterial blood vessels, but on the other hand also stimulates the formation of aldosterone in the adrenal cortex. Thus, the kidney acts as blood pressure sensor, and thus indirect volume sensor, in the circulating blood and counteracts, via the renin-angiotensin-aldosterone system, critical losses of volume by on the one hand increasing the blood pressure (angiotensin II effect), and on the other hand, by rebalancing the state of filling of the vascular system by increased reabsorption of sodium and water in the kidney (aldosterone effect).

This control system may be pathologically impaired in diverse ways. Thus, a chronic reduction in renal blood flow (e.g. as a result of heart failure and the congestion of blood in the venous system caused thereby) leads to a chronically excessive release of aldosterone. In turn it is followed by an expansion of the blood volume and thereby increases the weakness of the heart through an excessive supply of volume to the heart. Congestion of blood in the lungs with shortness of breath and formation of edema in the extremities, and ascites and pleural effusions may be the result; the renal blood flow falls further. In addition, the excessive aldosterone effect leads to a reduction in the potassium concentration in the blood and in the extracellular fluid. In heart muscles which have been previously damaged otherwise, cardiac arrhythmias with a fatal outcome may be induced if there is a deviation below a critical minimum level. This is likely to be one of the main causes of the sudden cardiac death which frequently occurs in patients with heart failure.

In addition, aldosterone is also thought to be responsible for a number of the myocardial remodeling processes typically to be observed in heart failure. Thus, hyperaldosteronism is a crucial component in the pathogenesis and prognosis of heart failure which may originally be induced by various types of damage such as, for example, a myocardial infarction, a myocardial inflammation or high blood pressure. This assumption is supported by the fact that there was a marked reduction in overall mortality in wide-ranging clinical studies on groups of patients with chronic heart failure and post acute myocardial infarction through the use of aldosterone antagonists [B. Pitt, F. Zannad, W. J. Remme et al., N. Engl. J. Med. 341, 709-717 (1999); B. Pitt, W. Remme, F. Zannad et al., N. Engl. J. Med. 348, 1309-1321 (2003)]. It was possible to achieve this inter alia by reducing the incidence of sudden cardiac death.

According to recent studies, a not inconsiderable number of patients suffering from essential hypertension are also found to have nonphysiological elevation of the plasma aldosterone concentration [N. M. Kaplan, The current epidemic of primary aldosteronism: Causes and consequences, J. Hypertens. 22, 863-869 (2004)]. The cause of this hyperaldosteronism and whether those affected represent a special risk group in relation to dying from sudden cardiac death or developing heart failure is unknown. However, it is to be assumed that a hyperaldosteronism diagnosed in connection with essential hypertension provides the starting point for a causal and prophylactically worthwhile therapy.

Another pathological state associated typically with an elevation of the plasma aldosterone concentration is advanced cirrhosis of the liver. The cause of the aldosterone elevation in this case is mainly the restricted aldosterone breakdown resulting from the impairment of liver function. Volume overload, edema and hypokalemia are the typical consequences, which can be successfully alleviated in clinical practice by aldosterone antagonists.

Far less common than the types of hyperaldosteronism detailed above are pathological states in which the impairment either is to be found in the hormone-producing cells of the adrenal itself, or the number or mass thereof is increased through hyperplasia or proliferation. Adenomas or diffuse hyperplasias of the adrenal cortex are the commonest cause of the primary hyperaldosteronism referred to as Conn's syndrome. The priority here too, besides surgical removal of the diseased tissue, is medical therapy with aldosterone antagonists [H. A. Kühn, and J. Schirmeister (Editors), Innere Medizin, 4th edition, Springer Verlag, Berlin, 1982].

The effects of aldosterone are mediated by the mineralocorticoid receptor which has an intracellular location in the target cells. The aldosterone antagonists available to date have, like aldosterone itself, a basic steroid structure. The utility of such steroidal antagonists is limited by their interactions with the receptors of other steroid hormones, which in some cases lead to considerable side effects such as gynecomastia and impotence and to discontinuation of the therapy [M. A. Zaman, S. Oparil, D. A. Calhoun, Nature Rev. Drug Disc. 1, 621-636 (2002)].

The use of potent, non-steroidal antagonists which are more selective for the mineralocorticoid receptor provides the possibility of avoiding this profile of side effects and thus achieving a distinct therapeutic advantage.

It is an object of the present invention to provide novel compounds which can be employed as selective mineralocorticoid receptor antagonists for the treatment of disorders, especially of cardiovascular disorders.

4-Aryl-1,4-dihydropyridine derivatives with coronary activity are disclosed in DE 2 003 146. Chromone- and thiochromone-substituted 1,4-dihydropyridines are described in DE 3 311 003-A1 and DE 3 311 005-A1 as cardiotonics and antihypotensives. EP 0 223 744-A2 claims 2-phenyl-chromone-substituted 1,4-dihydropyridine diesters as calcium antagonists. 4-Xanthenonyl-1,4-dihydropyridines having calcium-antagonistic activity are reported in Arzneim. Forsch. 42 (6), 797-801 (1992).

The present invention relates to compounds of the general formula (I)

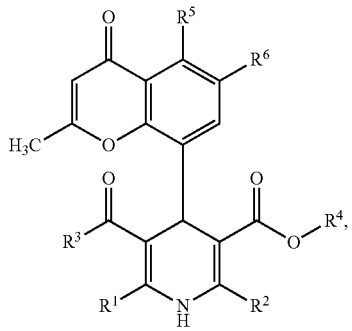

(I)

in which
R¹ and R² are identical or different and are independently of one another (C₁-C₄)-alkyl, trifluoro-methyl, cyclopropyl or cyclobutyl,
R³ is (C₃-C₇)-cycloalkyl, is (C₁-C₆)-alkyl which may be substituted by (C₃-C₇)-cycloalkyl or once to three times by fluorine, or is phenyl which may be substituted by halogen, cyano, (C₁-C₄)-alkyl, trifluoromethyl, (C₁-C₄)-alkoxy or trifluoromethoxy,
R⁴ is (C₃-C₇)-cycloalkyl or is (C₁-C₆)-alkyl which may be substituted by (C₃-C₇)-cycloalkyl or once to three times by fluorine,
R⁵ is hydrogen, halogen, cyano, nitro, trifluoromethyl, (C₁-C₄)-alkyl or (C₁-C₄)-alkoxy,
and
R⁶ is hydrogen or fluorine,
and the salts, solvates and solvates of the salts thereof.

Compounds of the invention are the compounds of the formula (I) and the salts, solvates and solvates of the salts thereof; the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds of the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds of the invention may occur in tautomeric forms, the present invention encompasses all tautomeric forms.

Salts which are preferred for the purposes of the present invention are physiologically acceptable salts of the compounds of the invention. Also encompassed are salts which are themselves unsuitable for pharmaceutical uses but can be used for example for isolating or purifying the compounds of the invention.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refers for the purposes of the invention to those forms of the compounds of the invention which form, in the solid or liquid state, a complex by coordination with solvent molecules. Hydrates are a specific form of solvates in which the coordination takes place with water. Hydrates are preferred solvates in the context of the present invention.

The present invention additionally encompasses prodrugs of the compounds of the invention. The term "prodrugs" encompasses compounds which themselves may be biologically active or inactive, but are converted during their residence time in the body into compounds of the invention (for example by metabolism or hydrolysis).

In the context of the present invention, the substituents have the following meaning, unless specified otherwise:
C₁-C₆-Alkyl and (C₁-C₄)-alkyl represent in the context of the invention a straight-chain or branched alkyl radical having respectively 1 to 6 and 1 and 4 carbon atoms. A straight-chain or branched alkyl radical having 1 to 4 carbon atoms is preferred. Mention may be made by way of example and preferably of: methyl, ethyl, n-propyl, isopropyl, n-butyl, iso-butyl, sec-butyl, tert-butyl, 1-ethylpropyl, n-pentyl, iso-pentyl and n-hexyl.
(C₃-C₇)-Cycloalkyl, (C₃-C₅)-cycloalkyl and (C₁-C₇)-cycloalkyl represent in the context of the invention a saturated monocyclic cycloalkyl group having respectively 3 to 7, 3 to 5 and 5 to 7 carbon atoms. Mention may be made by way of example and preferably of: cyclopropyl, cyclobutyl, cyclopentyl, cyclohexyl and cycloheptyl.
(C₁-C₄)-Alkoxy represents in the context of the invention a straight-chain or branched alkoxy radical having 1 to 4 carbon atoms. Mention may be made by way of example and preferably of: methoxy, ethoxy, n-propoxy, isopropoxy, n-butoxy and tert-butoxy.
Halogen includes in the context of the invention fluorine, chlorine, bromine and iodine. Fluorine or chlorine are preferred.

If radicals in the compounds of the invention are substituted, the radicals may be substituted one or more times, unless specified otherwise. In the context of the present invention, all radicals which occur more than once have a mutually independent meaning. Substitution by one, two or three identical or different substituents is preferred. Substitution by one substituent is very particularly preferred.

Preference is given to compounds of the formula (I) in which
R¹ and R² are identical or different and are methyl or trifluoromethyl,
R³ is (C₅-C₇)-cycloalkyl, is (C₁-C₆)-alkyl which may be substituted by (C₃-C₅)-cycloalkyl or once to three times by fluorine, or is phenyl which may be substituted by fluorine, chlorine, trifluoromethyl, methyl, isopropyl, tert-butyl or methoxy,
R⁴ is (C₃-C₅)-cycloalkyl or is (C₁-C₄)-alkyl which may be substituted by (C₃-C₅)-cycloalkyl or once to three times by fluorine, R⁵ is hydrogen, fluorine, chlorine, nitro or methyl,
and
R⁶ is hydrogen or fluorine,
and the salts, solvates and solvates of the salts thereof.

Particular preference is given to compounds of the formula (I) in which
R¹ is methyl or trifluoromethyl,
R² is methyl,
R³ is methyl, trifluoromethyl, isobutyl, isopentyl, cyclobutylmethyl, cyclopentylmethyl, 2-(cyclopropyl)ethyl, 2-(cyclobutyl)ethyl, 2-(cyclopentyl)ethyl or is phenyl which may be substituted in the para position by fluoro, trifluoromethyl, methyl or methoxy,
R⁴ is methyl, ethyl, 2,2,2-trifluoroethyl, n-propyl, isopropyl, tert-butyl, cyclobutyl, cyclopentyl, cyclopropylmethyl or cyclobutylmethyl,
R⁵ is hydrogen, fluorine or chlorine,
and
R⁶ is hydrogen,
and the salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds of the invention of the formula (I), characterized in that compounds of the formula (II)

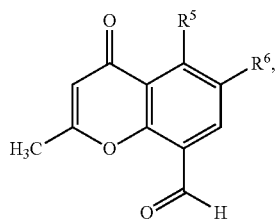

(II)

in which R⁵ and R⁶ each have the abovementioned meanings,
either
[A] are reacted in a one-stage process (one-pot reaction) with a compound of the formula (III)

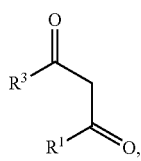

(III)

in which R¹ and R³ each have the abovementioned meanings,
and a compound of the formula (IV)

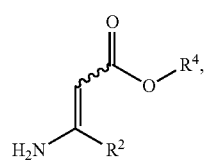

(IV)

in which R² and R⁴ each have the abovementioned meanings, or
[B] are reacted in a one-stage process (one-pot reaction) with a compound of the formula (V)

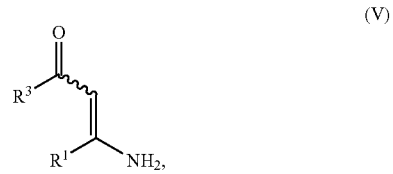

(V)

in which R¹ and R³ each have the abovementioned meanings,
and a compound of the formula (VI)

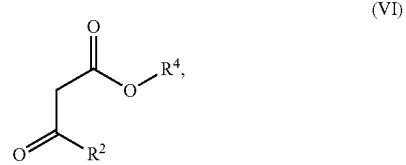

(VI)

in which R² and R⁴ each have the abovementioned meanings,
or
[C] are converted in a two-stage process firstly with a compound of the formula (III) into compounds of the formula (VII)

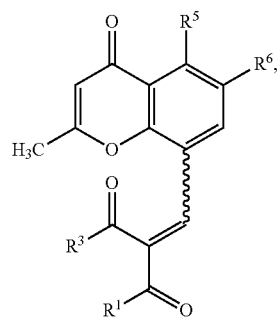

(VII)

in which R¹, R³, R⁵ and R⁶ each have the abovementioned meanings,
and the latter are then reacted in a second step with a compound of the formula (IV),
or
[D] are converted in a two-stage process firstly with a compound of the formula (VI) into compounds of the formula (VIII)

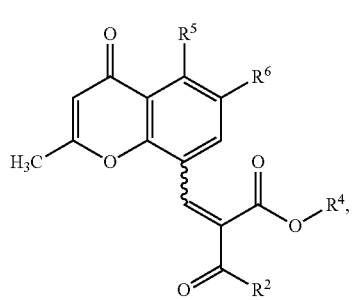

(VIII)

in which R², R⁴, R⁵ and R⁶ each have the abovementioned meanings,
and the latter are then reacted in a second step with a compound of the formula (V), the resulting compounds of the formula (I) are separated where appropriate by methods known to the skilled worker into their enantiomers and/or diastereomers, and the compounds of the formula (I) are converted where appropriate with the appropriate (i) solvents and/or (ii) bases or acids into the solvates, salts and/or solvates of the salts thereof.

In these process variants it is possible where appropriate also initially to employ easily cleavable carboxylic esters for the group —C(O)—O—R⁴, which are then cleaved by methods known to the skilled worker and reacted with the appropriate alcohols to give the compounds of the formula (I).

The reactions in processes [A] and [B], and in the second stage of processes [C] and [D] generally take place in inert solvents, where appropriate in the presence of an acid, in a temperature range from +20° C. to the boiling point of the solvent under atmospheric pressure.

Examples of inert solvents for this purpose are alcohols such as methanol, ethanol, n-propanol, isopropanol, n-butanol or tert-butanol, or other solvents such as acetonitrile, tetrahydrofuran, dioxane, 1,2-dimethoxyethane, toluene or glacial acetic acid. The reactions are preferably carried out in ethanol or isopropanol at the respective reflux temperature under atmospheric pressure.

The reactions in processes [A] and [B] are preferably carried out in the presence of an acid such as, for example, acetic acid, trifluoroacetic acid, p-toluenesulfonic acid, methanesulfonic acid or tetrabutylammonium hydrogen sulfate; addition of acetic acid is particularly preferred.

The reactions in the first stage of processes [C] and [D] generally take place in inert solvents, where appropriate in the presence of a base and/or acid, in a temperature range from +20° C. to the boiling point of the solvent under atmospheric pressure.

Examples of suitable inert solvents in this connection are halohydrocarbons such as dichloro-methane, trichloromethane, tetrachloromethane, trichloroethane or 1,2-dichloroethane, or other solvents such as acetonitrile, pyridine, benzene, toluene, chlorobenzene or hexane. The reactions preferably take place in dichloromethane or toluene at the respective reflux temperature under atmospheric pressure.

The reactions in the first stage of processes [C] and [D] are preferably carried out in the presence of an acid in combination with piperidine or pyridine as base and/or a dehydrating agent such as, for example, molecular sieves. Examples of suitable acids are acetic acid or p-toluenesulfonic acid. The reaction is particularly preferably carried out with addition of piperidinium acetate in conjunction with molecular sieves.

The compounds of the formula (II) are known from the literature or can be prepared in analogy to processes known from the literature, for example by ozonolysis of compounds of the formula (IX)

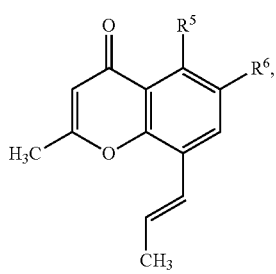

(IX)

in which R⁵ and R⁶ each have the abovementioned meanings, or by mono- or dibromination of compounds of the formula (X)

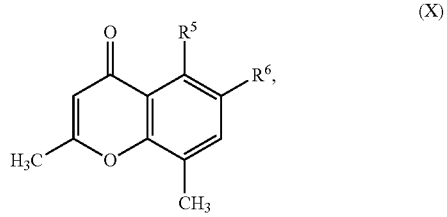

(X)

in which R⁵ and R⁶ each have the abovementioned meanings, to give compounds of the formula (XI) or (XII)

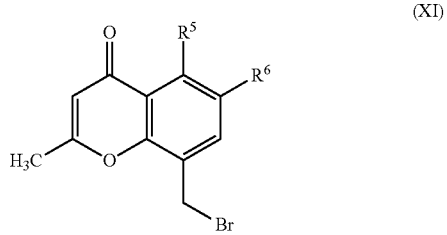

(XI)

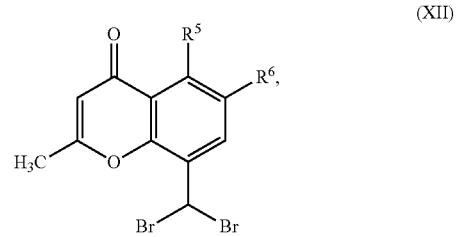

(XII)

in which R⁵ and R⁶ each have the abovementioned meanings, and subsequent reaction with N-methylmorpholine N-oxide. The starting compounds of the formulae (IX) and (X) are known from the literature or can be obtained by processes known from the literature [cf., for example, for (IX) and the reaction (IX)→(II): a) S. G. Jagadeesh et al., *Synth. Commun.* 31 (10), 1547-1557 (2001); b) DE 3 311 005-A1 and literature cited therein; for (X) and the reaction (X)→(XI)/(XII)→(II): a) P. Babin et al., *Tetrahedron* 37, 1131-1139 (1981); b) H. J. Bestmann, G. Schade, *Chem. Lett.*, 997-998 (1983); c) J. I. Ubeda et al., *Heterocycles* 38, 2677-2690 (1994); d) R. J. Chambers et al., *Bioorg. Med. Chem. Lett.* 8, 3577-3582 (1998); see also Schemes 1 and 3].

The compounds of the formulae (III), (IV), (V) and (VI) are commercially available, known from the literature or can be prepared by methods known from the literature [for the synthesis of 1,4-dihydropyridines cf. also D. M. Stout, A. I. Meyers, *Chem. Rev.* 1982, 82, 223-243; H. Meier et al., *Liebigs Ann. Chem.* 1977, 1888; H. Meier et al., *Liebigs Ann. Chem.* 1977, 1895 and H. Meier et al., *Liebigs Ann. Chem.* 1976, 1762].

The preparation of the compounds of the invention can be illustrated by the following synthesis schemes:

Scheme 1

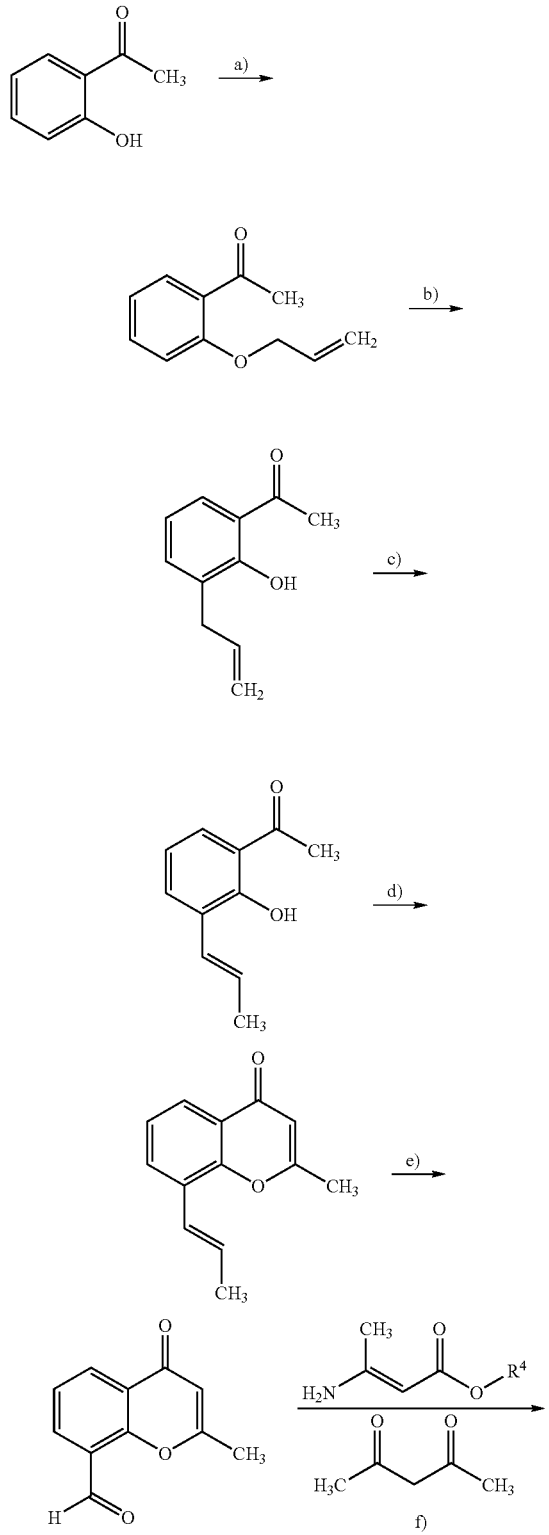

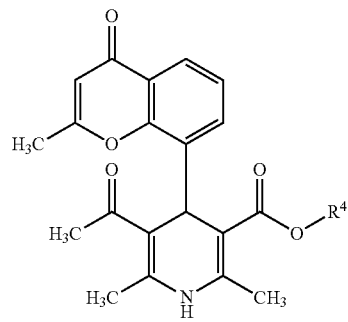

a): Allyl bromide, potassium carbonate, cat. potassium iodide, acetone, reflux;
b): 230° C., 4 h;
c): bis(benzonitrile)dichloropalladium(II), toluene, 120° C., 16 h;
d): acetyl chloride, sodium hydride, THF, 10-25° C., 16 h;
e): 1. ozone, dichloromethane, -60° C., 30 min; 2. dimethyl sulfide;
f): glacial acetic acid, 2-propanol, reflux, 10 h.

Scheme 2

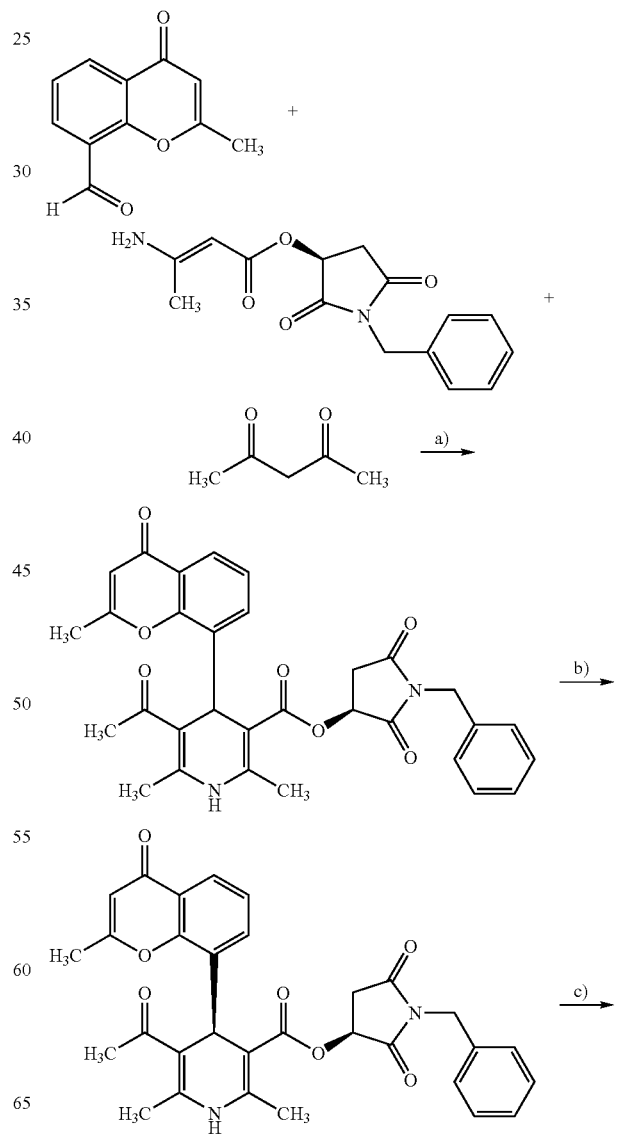

11
-continued
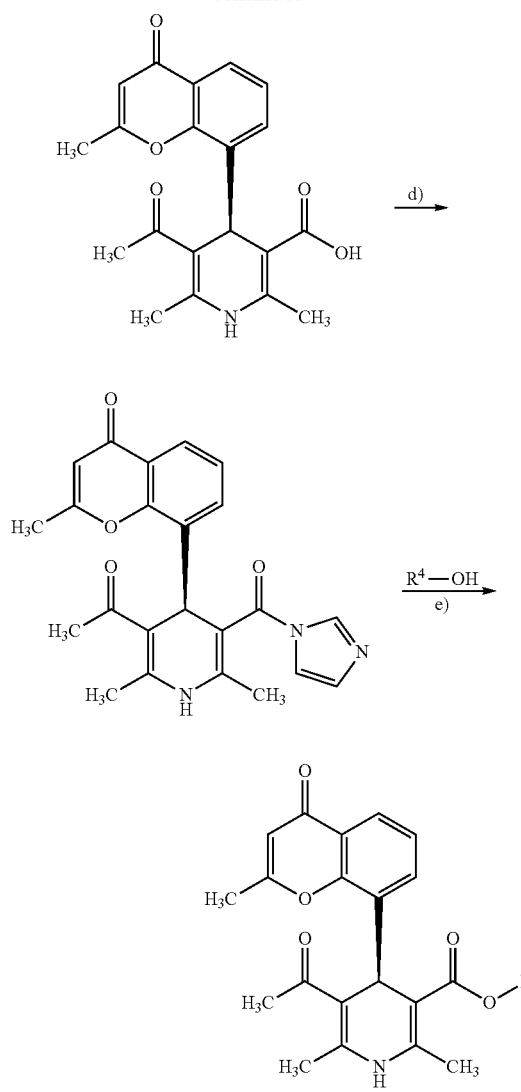
a): glacial acetic acid, 2-propanol, reflux;
b): diastereomer separation by crystallization;
c): DBU, ethyl acetate, RT, 8 h;
d): 1,1'-carbonyldiimidazole, THF, 50° C., 6 h;
e): reflux, 3 h.
Scheme 3
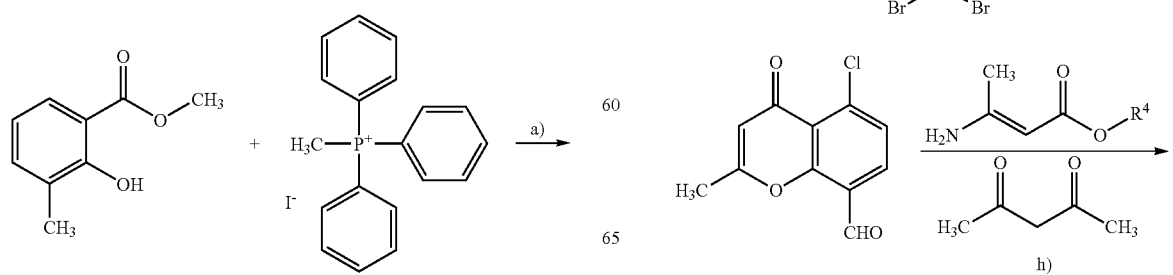
12
-continued
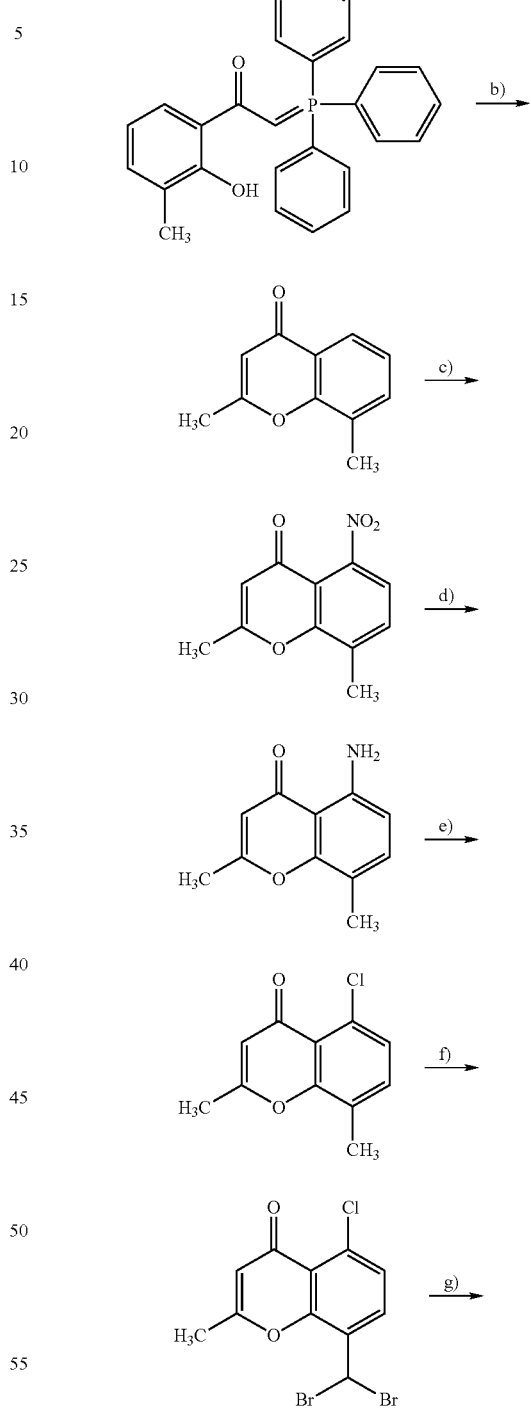

-continued

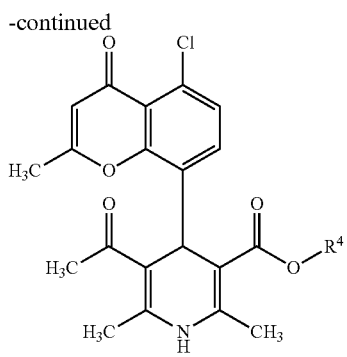

a): n-Butyllithium, THF, 60° C., 3 h;
b): acetic anhydride, pyridine, reflux, 6 h;
c): conc. H$_2$SO$_4$, HNO$_3$, 0° C., 1 h;
d): tin(II) chloride dihydrate, ethyl acetate, 70° C.;
e): tert-butyl nitrite, copper(II) chloride, acetonitrile, 65° C.;
f): N-bromosuccinimide, AIBN, tetrachloromethane, reflux;
g): N-methylmorpholine N-oxide, acetonitrile, reflux;
h): glacial acetic acid, 2-propanol, reflux].

The compounds of the invention act as antagonists of the mineralocorticoid receptor and show a valuable range of pharmacological effects which could not have been predicted. They are therefore suitable for use as medicaments for the treatment and/or prophylaxis of diseases in humans and animals.

The compounds of the invention are suitable for the prophylaxis and/or treatment of various disorders and disease-related conditions, especially of disorders which are characterized by or associated with an elevation of the plasma aldosterone concentration. Examples which may be mentioned are: idiopathic primary hyperaldosteronism, hyperaldosteronism associated with adrenal hyperplasia and/or adrenal adenomas and/or adrenal carcinomas, hyperaldosteronism associated with cirrhosis of the liver, hyperaldosteronism associated with heart failure, and hyperaldosteronism associated with essential hypertension.

The compounds of the invention are also suitable, because of their mechanism of action, for the prophylaxis of sudden cardiac death in patients at increased risk of dying of sudden cardiac death. These are in particular patients suffering for example from one of the following disorders: hypertension, heart failure, coronary heart disease, stable and unstable angina pectoris, myocardial ischemia, myocardial infarction, shock, arteriosclerosis, atrial and ventricular arrhythmia, transient and ischemic attacks, stroke, inflammatory cardiovascular disorders, peripheral and cardiac vascular disorders, peripheral blood flow disturbances, pulmonary hypertension, spasms of the coronary arteries and peripheral arteries, thromboses, thromboembolic disorders, and vasculitis.

The compounds of the invention can additionally be used for the prophylaxis and/or treatment of edema formation, such as, for example, pulmonary edema, renal edema or heart failure-related edema, and of restenoses such as following thrombolysis therapies, percutaneous transluminal angioplasties (PTA) and transluminal coronary angioplasties (PTCA), heart transplants and bypass operations.

The compounds of the invention are further suitable for use as diuretic and for electrolyte disturbances such as, for example, hypercalcemia.

The compounds of the invention can additionally be employed for the prophylaxis and/or treatment of diabetes mellitus and diabetic sequelae such as, for example, neuropathy and nephropathy, of acute and chronic renal failure, and of chronic renal insufficiency.

The present invention further relates to the use of the compounds of the invention for the treatment and/or prevention of disorders, especially of the aforementioned disorders.

The present invention further relates to the use of the compounds of the invention for the manufacture of a medicament for the treatment and/or prevention of disorders, especially of the aforementioned disorders.

The present invention further relates to a method for the treatment and/or prevention of disorders, especially of the aforementioned disorders, by using an effective amount of at least one of the compounds of the invention.

The compounds of the invention can be employed alone or, if required, in combination with other active ingredients. The present invention further relates to medicaments comprising at least one of the compounds of the invention and one or more further active ingredients, especially for the treatment and/or prevention of the aforementioned disorders. Suitable active ingredients for combinations are by way of example and preferably: ACE inhibitors, renin inhibitors, angiotensin II receptor antagonists, beta blockers, acetylsalicylic acid, diuretics, potassium supplements, calcium antagonists, statins, digitalis (digoxin) derivatives, calcium sensitizers such as levosimendan, nitrates, anticoagulants, antiarrhythmics, vasodilators, and thrombolytics.

The present invention further relates to medicaments which comprise at least one compound of the invention, normally together with one or more inert, non-toxic, pharmaceutically suitable excipients, and to the use thereof for the aforementioned purposes.

The compounds of the invention may have systemic and/or local effects. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds of the invention can be administered in administration forms suitable for these administration routes.

Suitable for oral administration are administration forms which function according to the prior art and deliver the compounds of the invention rapidly and/or in a modified manner, and which contain the compounds of the invention in crystalline and/or amorphized and/or dissolved form, such as, for example, tablets (uncoated and coated tablets, for example having coatings which are resistant to gastric juice or are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other routes of administration are, for example, pharmaceutical forms for inhalation (inter alia powder inhalers, nebulizers), nasal drops, solutions, sprays; tablets for lingual, sublingual or buccal administration, films/wafers or capsules, suppositories, preparations for the ears and eyes, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

Oral or parenteral administration are preferred, especially oral administration.

The compounds of the invention can be converted into the stated administration forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorings (e.g. inorganic pigments such as, for example, iron oxides) and masking flavors and/or odors.

It has generally proved to be advantageous on parenteral administration to administer amounts of about 0.001 to 1 mg/kg, preferably about 0.01 to 0.5 mg/kg of body weight per day to achieve effective results. On oral administration, the dosage is about 0.01 to 100 mg/kg, preferably about 0.01 to 20 mg/kg, and very particularly preferably about 0.1 to 10 mg/kg of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. Where relatively large amounts are administered, it may be advisable to distribute these in a plurality of single doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data of liquid/liquid solutions are based in each case on the volume.

A. EXAMPLES

Abbreviations and Acronyms

| | |
|---|---|
| Ac | Acetyl |
| AIBN | 2,2'-Azobis-2-methylpropanenitrile |
| cat. | Catalytic |
| conc. | Concentrated |
| CI | Chemical ionization (in MS) |
| DBU | 1,8-Diazabicyclo[5.4.0]undec-7-ene |
| DMF | Dimethylformamide |
| DMSO | Dimethyl sulfoxide |
| ESI | Electrospray ionization (in MS) |
| GC-MS | Coupled gas chromatography-mass spectroscopy |
| h | Hour(s) |
| HPLC | High pressure, high performance liquid chromatography |
| LC-MS | Coupled liquid chromatography-mass spectroscopy |
| min | Minute(s) |
| MS | Mass spectroscopy |
| NMR | Nuclear magnetic resonance spectroscopy |
| $R_f$ | Retention index (in TLC) |
| $R_t$ | Retention time (in HPLC) |
| RT | Room temperature |
| THF | Tetrahydrofuran |
| TLC | Thin layer chromatography |

LC-MS GC-Ms and HPLC Methods:

Method 1 (LC-MS):

MS instrument type: Micromass ZQ; HPLC instrument type: Waters Alliance 2795; column: Phenomenex Synergi 2µ Hydro-RP Mercury 20 mm×4 mm; Eluent A: 1 l water+0.5 ml 50% formic acid, Eluent B: 1 l acetonitrile+0.5 ml 50% formic acid; gradient: 0.0 min 90% A →2.5 min 30% A→3.0 min 5% A→4.5 min 5% A; flow rate: 0.0 min 1 ml/min →2.5 min/3.0 min/4.5 min 2 ml/min; oven: 50° C.; UV detection: 210 nm.

Method 2 (LC-MS):

MS instrument type: Micromass ZQ; HPLC instrument type: HP 100 Series; UV DAD; column: Phenomenex Synergi 2µ Hydro-RP Mercury 20 mm×4 mm; Eluent A: 1 l water+0.5 ml 50% formic acid, Eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min →2.5 min/3.0 min/4.5 min 2 ml/min; oven: 50° C.; UV detection: 210 nm.

Method 3 (LC-MS):

Instrument: Micromass Quattro LCZ with HPLC Agilent Series 1100; column: Phenomenex Synergi 2µ Hydro-RP Mercury 20 mm×4 mm; Eluent A: 1 l water+0.5 ml 50% formic acid, Eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min →2.5 min/3.0 min/4.5 min 2 ml/min; oven: 50° C.; UV detection: 208-400 nm.

Method 4 (HPLC, Enantiomer Separation):

Column: Daicel Chiralpak AD-H, 5 µm, 250 mm×20 mm; Eluent: isohexane/2-propanol 75:25+2.5% diethylamine; temperature: 35° C.; flow rate: 15 ml/min; UV detection: 220 nm.

Method 5 (HPLC, Enantiomer Separation):

Column: KBD 840, 250 mm×46 mm, based on the chiral selector poly(N-methacryloyl-L-leucine 1-menthylamide); eluent: isohexane/2-propanol 1:9; temperature: 24° C.; flow rate: 1 ml/min; UV detection: 280 nm.

Method 6 (GC-MS):

Instrument: Micromass GCT, GC 6890; column: Restek RTX-35MS, 30 m×250 µm×0.25 µm; constant flow with helium: 0.88 ml/min; oven: 60° C.; inlet: 250° C.; gradient: 60° C. (maintained for 0.30 min), 50° C./min →120° C., 16° C./min →250° C., 30° C./min →300° C. (maintained for 1.7 min).

EXEMPLARY EMBODIMENTS

Where structurally possible, and unless indicated otherwise, the alkenes used as starting materials or intermediates are in the form of E/Z mixtures.

General Method for Preparing 3-Aminocrotonic Esters:

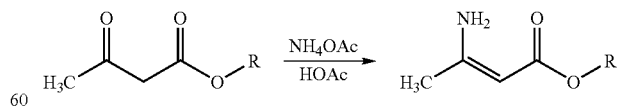

2 equivalents of ammonium acetate and 0.9 equivalent of glacial acetic acid are added to a solution of the appropriate acetoacetic ester in toluene, and the mixture is stirred under reflux with a water trap overnight. After cooling, the reaction solution is diluted with ethyl acetate and washed successively with sodium bicarbonate solution and sodium chloride solu-

Example 1

Ethyl 5-acetyl-2,6-dimethyl-4-(2-methyl-4-oxo-4H-chromen-8-yl)-1,4-dihydropyridine-3-carboxylate Stage 1a):

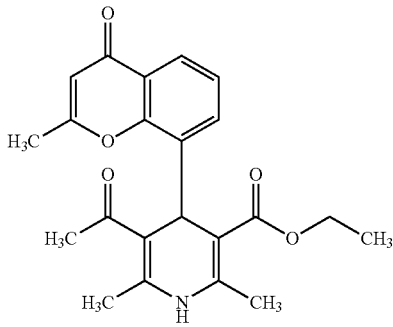

1-[2-(Allyloxy)phenyl]ethanone

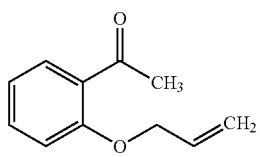

542 g (3.9 mol) of 2-hydroxyacetophenone are heated to reflux with 592 g (4.9 mol) of allyl bromide, 1000 g (7.2 mol) of potassium carbonate and 13.2 g (79 mmol) of potassium iodide in 2.4 litres of acetone for 24 h. Cooling to room temperature is followed by filtration and removal of the solvent in vacuo. The residue is dissolved in toluene and washed with 10% strength sodium hydroxide solution and water. Concentration results in 689 g (98% of theory) of the title compound.

$^1$H-NMR (300 MHz, CDCl$_3$): δ=2.68 (s, 3H), 4.68 (dd, 2H), 5.89 (dd, 2H), 6.09 (m, 1H), 6.99 (dd, 2H), 7.44 (m, 1H), 7.71 (d, 1H).

Stage 1b):

1-(3-Allyl-2-hydroxyphenyl)ethanone

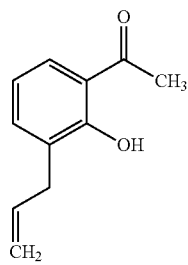

160 g (0.9 mol) of 1-[2-(allyloxy)phenyl]ethanone are stirred at 230-240° C. in a metal bath for 4 h. After cooling to room temperature, the product is distilled through a thin-film evaporator at 140° C. and 0.4 mbar. 155 g (97% of theory) of the title compound are obtained.

$^1$H-NMR (300 MHz, CDCl$_3$): δ=2.68 (s, 3H), 3.44 (d, 2H), 5.09 (m, 2H), 6.01 (m, 1H), 6.85 (t, 1H), 7.38 (dd, 1H), 7.62 (dd, 1H), 12.61 (s, 1H).

Stage 1c):

1-{2-Hydroxy-3-[(1E)-prop-1-en-1-yl]phenyl}ethanone

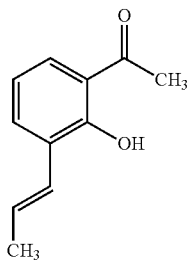

40 g (227 mmol) of 1-(3-allyl-2-hydroxyphenyl)ethanone are dissolved in 120 ml of toluene, and 2.17 g (5.6 mmol) of bis(benzonitrile)dichloropalladium(II) are added. The reaction mixture is heated at 120° C. overnight. Cooling to room temperature is followed by filtration through kieselguhr and removal of the solvent in vacuo. 20.9 g (95% of theory) of the title compound are obtained and are reacted without further purification in the next stage.

LC-MS (Method 1): R$_t$=2.36 min; [M+H]$^+$=177

$^1$H-NMR (300 MHz, CDCl$_3$): δ=1.91 (dd, 3H), 2.63 (s, 3H), 6.32 (m, 1H), 6.73 (dd, 1H), 6.85 (t, 1H), 7.59 (m, 2H), 12.74 (s, 1H).

Stage 1d):

2-Methyl-8-[(1E)-prop-1-en-1-yl]-4H-chromen-4-one

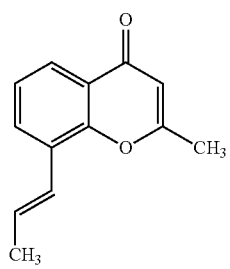

12.52 g (313.2 mmol) of 60% sodium hydride (suspension in mineral oil) are introduced into 300 ml of absolute THF at 10° C. under argon. 18.4 g (104.4 mmol) of 1-{2-hydroxy-3-[(1E)-prop-1-en-1-yl]phenyl}ethanone are slowly added dropwise to the suspension. After 15 min, 9 g (114.9 mmol) of acetyl chloride are added. The reaction mixture is stirred at room temperature overnight. It is hydrolyzed with 300 ml of water and extracted several times with ethyl acetate. Washing of the organic phase with saturated sodium chloride solution is followed by drying over sodium sulfate. The solvent is then removed in vacuo. The residue is taken up in 200 ml of methanol and heated with 50 ml of 20% strength hydrochloric acid at 80° C. for 30 min. The solvent is then removed in vacuo, and the residue is mixed with 400 ml of water. It is extracted several times with dichloromethane. The organic phase is dried over magnesium sulfate and then the solvent is removed in vacuo, and the residue is purified by column chromatography (mobile phase: dichloromethane/methanol 98:2). 10.5 g (50.2% of theory) of the title compound are obtained as a yellow oil.

LC-MS (Method 3): $R_t$=2.07 min; [M+H]$^+$=201

$^1$H-NMR (300 MHz, CDCl$_3$): δ=1.98 (dd, 3H), 2.43 (s, 3H), 6.18 (s, 1H), 6.40 (m, 1H), 6.85 (dd, 1H), 7.31 (t, 1H), 7.72 (dd, 1H), 8.05 (dd, 1H).

Stage 1e):

2-Methyl-4-oxo-4H-chromene-8-carbaldehyde

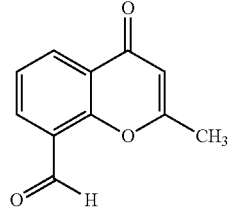

18.5 g (62.8 mmol) of 2-methyl-8-[(1E)-prop-1-en-1-yl]-4H-chromen-4-one are dissolved in 400 ml of dichloromethane and cooled to −60° C. Ozone is passed into the reaction solution for 30 min. Dimethyl sulfide is then added to the reaction mixture. After warming to room temperature, the solvent is removed in vacuo, and the residue is slurried in a little methanol. The solid remaining after filtration is recrystallized from diethyl ether. 9.1 g (77.4% of theory) of the title compound are obtained.

LC-MS (Method 1): $R_t$=1.31 min; [M+H]$^+$=189

$^1$H-NMR (300 MHz, CDCl$_3$): δ=2.48 (s, 3H), 6.27 (s, 1H), 7.51 (m, 1H), 8.21 (dd, 1H), 8.46 (dd, 1H), 10.67 (s, 1H).

Stage 1f):

Ethyl 5-acetyl-2,6-dimethyl-4-(2-methyl-4-oxo-4H-chromen-8-yl)-1,4-dihydropyridine-3-carboxylate

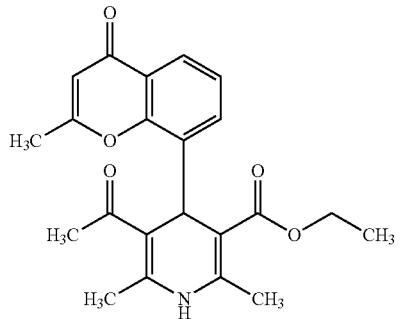

100 mg (0.53 mmol) of 2-methyl-4-oxo-4H-chromene-8-carbaldehyde are dissolved with 93.1 mg (0.93 mmol) of 2,4-pentanedione, 68.6 mg (0.53 mmol) of ethyl 3-aminocrotonate and 31.9 mg (0.53 mmol) of acetic acid in 5 ml of 2-propanol and heated to reflux under argon for 10 h. The solvent is removed in vacuo, and the residue is purified by preparative HPLC. 91 mg (45% of theory) of the title compound are obtained as a yellow solid.

LC-MS (Method 1): $R_t$=1.71 min; [M+H]$^+$=382

$^1$H-NMR (300 MHz, DMSO-d$_6$): δ=1.01 (t, 3H), 2.16 (s, 3H), 2.22 (s, 3H), 2.27 (s, 3H), 2.39 (s, 3H), 3.91 (q, 2H), 5.44 (s, 1H), 6.23 (s, 1H), 7.32 (t, 1H), 7.58 (dd, 1H), 7.79 (dd, 1H), 8.98 (s, 1H).

The racemate obtained in this way is separated into the enantiomers by HPLC on chiral phase (Method 4):

Enantiomer 1: $R_t$=5.043 min;

Enantiomer 2: $R_t$=5.433 min.

A single-crystal X-ray structural analysis revealed a (4R) configuration for enantiomer 2.

Example 2

Cyclopentyl 5-acetyl-2,6-dimethyl-4-(2-methyl-4-oxo-4H-chromen-8-yl)-1,4-dihydropyridine-3-carboxylate

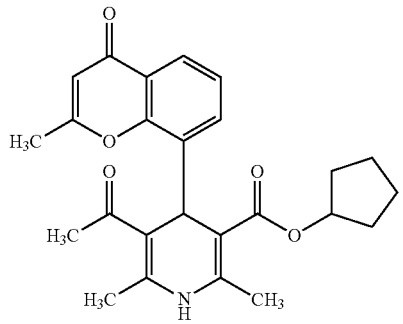

100 mg (0.53 mmol) of 2-methyl-4-oxo-4H-chromene-8-carbaldehyde are dissolved with 93.1 mg (0.93 mmol) of 2,4-pentanedione, 89.9 mg (0.53 mmol) of cyclopentyl 3-aminocrotonate and 31.9 mg (0.53 mmol) of acetic acid in 5 ml of 2-propanol and heated to reflux under argon for 10 h. The solvent is removed in vacuo, and the residue is purified by preparative HPLC. 84 mg (37.5% of theory) of the title compound are obtained as a yellow solid.

LC-MS (Method 1): $R_t$=2.02 min; [M+H]$^+$=422

$^1$H-NMR (300 MHz, DMSO-d$_6$): δ=1.19 (m, 1H), 1.39 (m, 2H), 1.56 (m, 4H), 1.75 (m, 1H), 2.17 (s, 3H), 2.20 (s, 3H), 2.28 (s, 3H), 2.39 (s, 3H), 4.95 (m, 1H), 5.38 (s, 1H), 6.22 (s, 1H), 7.32 (t, 1H), 7.58 (dd, 1H), 7.80 (dd, 1H), 8.96 (s, 1H).

Example 3

Isopropyl 5-acetyl-2,6-dimethyl-4-(2-methyl-4-oxo-4H-chromen-8-yl)-1,4-dihydropyridine-3-carboxylate

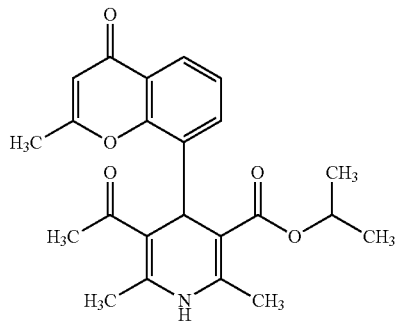

100 mg (0.53 mmol) of 2-methyl-4-oxo-4H-chromene-8-carbaldehyde are dissolved with 93.1 mg (0.93 mmol) of 2,4-pentanedione, 76.1 mg (0.53 mmol) of isopropyl 3-aminocrotonate and 31.9 mg (0.53 mmol) of acetic acid in 5 ml of 2-propanol and heated to reflux under argon for 10 h. The solvent is removed in vacuo, and the residue is purified by preparative HPLC. 62 mg (29% of theory) of the title compound are obtained as a yellow solid.

LC-MS (Method 1): $R_t$=1.84 min; $[M+H]^+$=396
$^1$H-NMR (300 MHz, DMSO-$d_6$): δ=0.84 (d, 3H), 1.13 (d, 3H), 2.16 (s, 3H), 2.22 (s, 3H), 2.27 (s, 3H), 2.40 (s, 3H), 4.76 (m, 1H), 5.41 (s, 1H), 6.22 (s, 1H), 7.32 (t, 1H), 7.58 (dd, 1H), 7.80 (dd, 1H), 8.94 (s, 1H).

Example 4

Methyl 5-acetyl-2,6-dimethyl-4-(2-methyl-4-oxo-4H-chromen-8-yl)-1,4-dihydropyridine-3-carboxylate

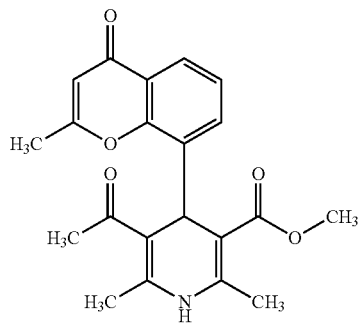

100 mg (0.53 mmol) of 2-methyl-4-oxo-4H-chromene-8-carbaldehyde are dissolved with 93.1 mg (0.93 mmol) of 2,4-pentanedione, 61.1 mg (0.53 mmol) of methyl 3-aminocrotonate and 31.9 mg (0.53 mmol) of acetic acid in 5 ml of 2-propanol and heated to reflux under argon for 10 h. The solvent is removed in vacuo, and the residue is purified by preparative HPLC. 77 mg (39% of theory) of the title compound are obtained as a yellow solid.

LC-MS (Method 1): $R_t$=1.59 min; $[M+H]^+$=368
$^1$H-NMR (300 MHz, DMSO-$d_6$): δ=2.15 (s, 3H), 2.24 (s, 3H), 2.26 (s, 3H), 2.40 (s, 3H), 3.48 (s, 3H), 5.45 (s, 1H), 6.22 (s, 1H), 7.32 (t, 1H), 7.54 (dd, 1H), 7.80 (dd, 1H), 9.01 (s, 1H).

Example 5 tert-Butyl 5-acetyl-2,6-dimethyl-4-(2-methyl-4-oxo-4H-chromen-8-yl)-1,4-dihydropyridine-3-carboxylate

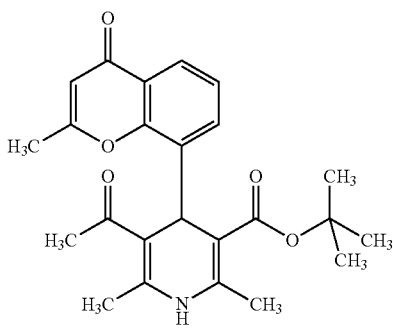

100 mg (0.53 mmol) of 2-methyl-4-oxo-4H-chromene-8-carbaldehyde are dissolved with 93.1 mg (0.93 mmol) of 2,4-pentanedione, 83.5 mg (0.53 mmol) of tert-butyl 3-aminocrotonate and 31.9 mg (0.53 mmol) of acetic acid in 5 ml of 2-propanol and heated to reflux under argon for 10 h. The solvent is removed in vacuo, and the residue is purified by column chromatography (mobile phase: dichloromethane/methanol 95:5). 87 mg (40% of theory) of the title compound are obtained as a yellow solid.

LC-MS (Method 1): $R_t$=1.97 min; $[M+H]^+$=410
$^1$H-NMR (300 MHz, DMSO-$d_6$): δ=1.25 (s, 9H), 2.16 (s, 3H), 2.20 (s, 3H), 2.24 (s, 3H), 2.38 (s, 3H), 5.35 (s, 1H), 6.22 (s, 1H), 7.33 (t, 1H), 7.56 (dd, 1H), 7.81 (dd, 1H), 8.88 (s, 1H).

Example 6

Cyclobutyl 5-acetyl-2,6-dimethyl-4-(2-methyl-4-oxo-4H-chromen-8-yl)-1,4-dihydropyridine-3-carboxylate

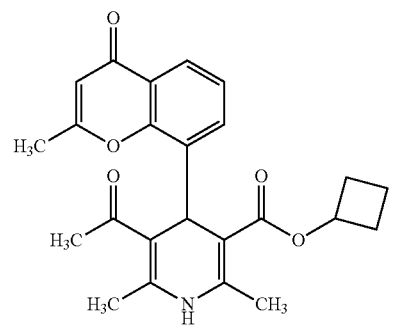

100 mg (0.53 mmol) of 2-methyl-4-oxo-4H-chromene-8-carbaldehyde are dissolved with 93.1 mg (0.93 mmol) of 2,4-pentanedione, 82.5 mg (0.53 mmol) of cyclobutyl 3-aminocrotonate and 31.9 mg (0.53 mmol) of acetic acid in 5 ml of 2-propanol and heated to reflux under argon for 10 h. The solvent is removed in vacuo, and the residue is purified by preparative HPLC. 82 mg (37% of theory) of the title compound are obtained as a yellow solid.

LC-MS (Method 1): $R_t$=1.92 min; $[M+H]^+$=408
$^1$H-NMR (300 MHz, DMSO-$d_6$): δ=1.55 (m, 3H), 1.92 (m, 1H), 2.04 (m, 1H), 2.16 (s, 3H), 2.22 (s, 3H), 2.23 (m, 1H), 2.27 (s, 3H), 2.40 (s, 3H), 4.78 (m, 1H), 5.42 (s, 1H), 6.23 (s, 1H), 7.33 (t, 1H), 7.61 (dd, 1H), 7.83 (dd, 1H), 8.98 (s, 1H).

The racemate obtained in this way is separated into the enantiomers by HPLC on chiral phase (Method 5):
Enantiomer 1: $R_t$=5.627 min;
Enantiomer 2: $R_t$=7.264 min.

Example 7

Methyl 2,6-dimethyl-4-(2-methyl-4-oxo-4H-chromen-8-yl)-5-(trifluoroacetyl)-1,4-dihydropyridine-3-carboxylate

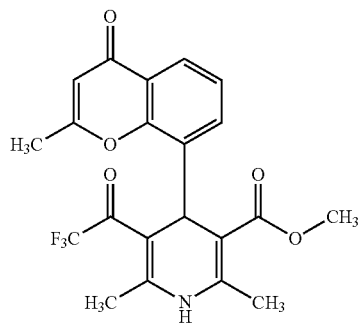

100 mg (0.53 mmol) of 2-methyl-4-oxo-4H-chromene-8-carbaldehyde are dissolved with 143.3 mg (0.93 mmol) of 1,1,1-trifluoroacetylacetone, 61.1 mg (0.53 mmol) of methyl 3-aminocrotonate and 31.9 mg (0.53 mmol) of acetic acid in 5 ml of 2-propanol and heated to reflux under argon for 10 h.

The solvent is removed in vacuo, and the residue is purified by preparative HPLC. 22 mg (9.8% of theory) of the title compound are obtained as a yellow solid.

LC-MS (Method 3): $R_t$=2.22 min; $[M+H]^+$=422

$^1$H-NMR (300 MHz, DMSO-$d_6$): δ=2.26 (s, 3H), 2.38 (s, 3H), 2.39 (s, 3H), 3.60 (s, 3H), 5.29 (s, 1H), 6.24 (s, 1H), 7.34 (t, 1H), 7.49 (dd, 1H), 7.84 (dd, 1H), 9.96 (s, 1H).

Example 8

Isopropyl 2,6-dimethyl-4-(2-methyl-4-oxo-4H-chromen-8-yl)-5-(trifluoroacetyl)-1,4-dihydro-pyridine-3-carboxylate

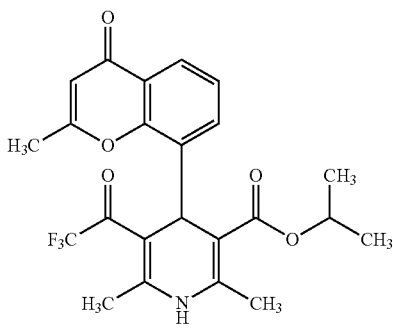

100 mg (0.53 mmol) of 2-methyl-4-oxo-4H-chromene-8-carbaldehyde are dissolved with 143.3 mg (0.93 mmol) of 1,1,1-trifluoroacetylacetone, 76.09 mg (0.53 mmol) of isopropyl 3-aminocrotonate and 31.9 mg (0.53 mmol) of acetic acid in 5 ml of 2-propanol and heated to reflux under argon for 10 h. The solvent is removed in vacuo, and the residue is purified by column chromatography (mobile phase: dichloromethane/methanol 95:5). 15 mg (6.2% of theory) of the title compound are obtained as a yellow solid.

LC-MS (Method 2): $R_t$=2.49 min; $[M+H]^+$=450

$^1$H-NMR (300 MHz, DMSO-$d_6$): δ=1.00 (d, 3H), 1.15 (d, 3H), 2.27 (s, 3H), 2.35 (s, 3H), 2.37 (s, 3H), 4.87 (m, 1H), 5.54 (s, 1H), 6.24 (s, 1H), 7.34 (t, 1H), 7.51 (dd, 1H), 7.85 (dd, 1H), 9.89 (s, 1H).

Example 9

Cyclobutyl 2,6-dimethyl-4-(2-methyl-4-oxo-4H-chromen-8-yl)-5-(trifluoroacetyl)-1,4-dihydro-pyridine-3-carboxylate

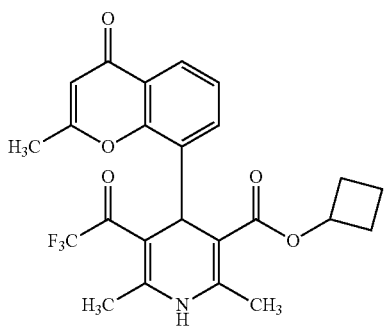

100 mg (0.53 mmol) of 2-methyl-4-oxo-4H-chromene-8-carbaldehyde are dissolved with 143.3 mg (0.93 mmol) of 1,1,1-trifluoroacetylacetone, 82.4 mg (0.53 mmol) of cyclobutyl 3-aminocrotonate and 31.9 mg (0.53 mmol) of acetic acid in 5 ml of 2-propanol and heated to reflux under argon for 10 h. The solvent is removed in vacuo, and the residue is purified by column chromatography (mobile phase: dichloromethane/methanol 95:5). 8 mg (3.2% of theory) of the title compound are obtained as a yellow solid.

LC-MS (Method 2): $R_t$=2.56 min; $[M+H]^+$=462

$^1$H-NMR (300 MHz, DMSO-$d_6$): δ=1.55 (m, 1H), 1.69 (m, 1H), 1.77 (m, 1H), 1.92 (m, 1H), 2.16 (m, 1H), 2.24 (m, 1H), 2.27 (s, 3H), 2.37 (s, 6H), 4.90 (m, 1H), 5.55 (s, 1H), 6.24 (s, 1H), 7.35 (t, 1H), 7.52 (dd, 1H), 7.85 (dd, 1H), 9.93 (s, 1H).

Example 10

Ethyl 2,6-dimethyl-4-(2-methyl-4-oxo-4H-chromen-8-yl)-5-(trifluoroacetyl)-1,4-dihydropyridine-3-carboxylate

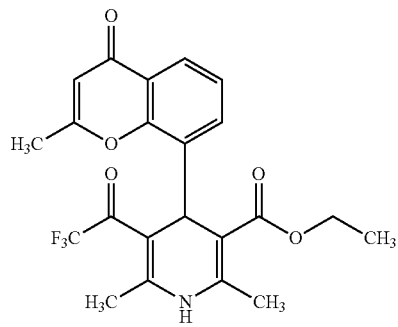

100 mg (0.53 mmol) of 2-methyl-4-oxo-4H-chromene-8-carbaldehyde are dissolved with 143.3 mg (0.93 mmol) of 1,1,1-trifluoroacetylacetone, 68.6 mg (0.53 mmol) of ethyl 3-aminocrotonate and 31.9 mg (0.53 mmol) of acetic acid in 5 ml of 2-propanol and heated to reflux under argon for 10 h. The solvent is removed in vacuo, and the residue is purified by column chromatography (mobile phase: dichloromethane/methanol 95:5). 16 mg (7% of theory) of the title compound are obtained as a yellow solid.

LC-MS (Method 2): $R_t$=2.38 min; $[M+H]^+$=436

$^1$H-NMR (300 MHz, DMSO-$d_6$): δ=1.09 (t, 3H), 2.27 (s, 3H), 2.37 (s, 3H), 2.38 (s, 3H), 4.05 (q, 2H), 5.58 (s, 1H), 6.24 (s, 1H), 7.34 (t, 1H), 7.48 (dd, 1H), 7.84 (dd, 1H), 9.93 (s, 1H).

Example 11

Ethyl 5-acetyl-2,6-dimethyl-4H-(5-fluoro-2-methyl-4-oxo-4H-chromen-8-yl)-4-dihydropyridine-3-carboxylate

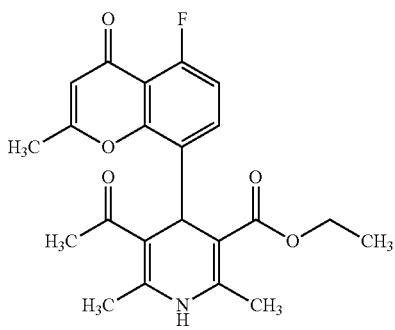

Stage 11a):

5-Fluoro-2-methyl-4-oxo-4H-chromene-8-carbaldehyde

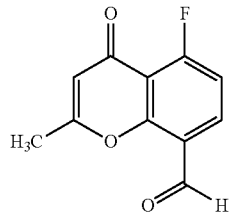

The title compound is obtained in analogy to Example 1, Stage a-e, starting from 4-fluoro-2-hydroxyacetophenone.

LC-MS (Method 3): $R_t$=1.47 min; [M+H]$^+$=207

$^1$H-NMR (300 MHz, CDCl$_3$): δ=2.45 (t, 3H), 6.21 (s, 1H), 7.15 (dd, 1H), 8.20 (dd, 1H), 10.57 (s, 1H).

Stage 11b):

3-[(5-Fluoro-2-methyl-4-oxo-4H-chromen-8-yl)methylene]pentane-2,4-dione

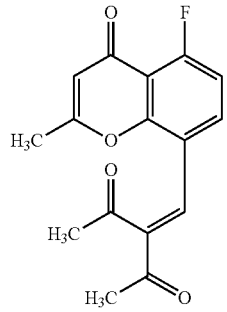

239 mg (1.16 mmol) of 5-fluoro-2-methyl-4-oxo-4H-chromene-8-carbaldehyde, 0.14 ml (1.28 mmol) of 2,4-pentanedione, 0.085 ml (1.45 mmol) of acetic acid and 0.01 ml (0.12 mmol) of piperidine are heated under reflux in 25 ml of anhydrous dichloromethane for 3 h. After addition of 80 mg of pyridinium para-toluenesulfonate and heating under reflux for a further 12 h, the reaction solution is washed with water and with brine and concentrated. 308.4 mg (91% of theory) of a red oil are obtained and are directly reacted further.

LC-MS (Method 3): R=1.72 min; [M+H]$^+$=289.

Stage 11c):

Ethyl 5-acetyl-2,6-dimethyl-4-(5-fluoro-2-methyl-4-oxo-4H-chromen-8-yl)-1,4-dihydropyridine-3-carboxylate

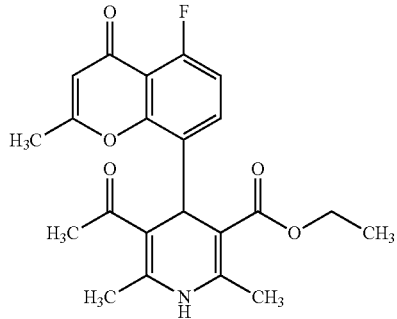

150 mg (0.52 mmol) of 3-[(5-fluoro-2-methyl-4-oxo-4H-chromen-8-yl)methylene]pentane-2,4-dione are dissolved with 33.6 mg (0.26 mmol) of ethyl 3-aminocrotonate in 5 ml of 2-propanol and heated under reflux under argon for 3 h. The solvent is removed in vacuo, and the residue is purified by column chromatography (mobile phase: ethyl acetate/cyclohexane 2:1). 50.1 mg (48% of theory) of the title compound are obtained as a yellow solid.

LC-MS (Method 3): $R_t$=1.82 min; [M+H]$^+$=400

$^1$H-NMR (300 MHz, CDCl$_3$): δ=1.14 (t, 3H), 2.24 (s, 3H), 2.29 (s, 3H), 2.37 (s, 3H), 2.38 (s, 3H), 4.07 (q, 2H), 5.53 (s, 1H), 5.73 (s, 1H), 6.11 (s, 1H), 6.91 (t, 1H), 7.49 (m, 1H).

Example 12

Cyclobutyl 5-acetyl-2,6-dimethyl-4-(5-fluoro-2-methyl-4-oxo-4H-chromen-8-yl)-1,4-dihydro-pyridine-3-carboxylate

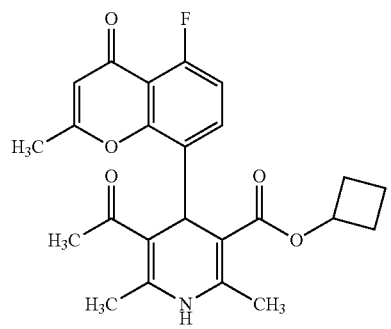

150 mg (0.52 mmol) of 3-[(5-fluoro-2-methyl-4-oxo-4H-chromen-8-yl)methylene]pentane-2,4-dione are dissolved with 40.4 mg (0.26 mmol) of cyclobutyl 3-aminocrotonate in 5 ml of 2-propanol and heated under reflux under argon for 3 h. The solvent is removed in vacuo, and the residue is purified by column chromatography (mobile phase: ethyl acetate/cyclohexane 2:1). 54.8 mg (50% of theory) of the title compound are obtained as a yellow solid.

LC-MS (Method 3): $R_t$=1.97 min; [M+H]$^+$=426

$^1$H-NMR (300 MHz, CDCl$_3$): δ=1.18 (m, 1H), 1.57 (m, 2H), 1.74 (m, 2H), 1.95 (m, 1H), 2.22 (s, 3H), 2.28 (s, 3H), 2.36 (s, 3H), 2.39 (s, 3H), 4.91 (quin, 1H), 5.52 (s, 1H), 5.79 (s, 1H), 6.11 (s, 1H), 6.92 (dd, 1H), 7.49 (m, 1H).

Example 13

Cyclobutyl 5-acetyl-2,6-dimethyl-4-(5,6-difluoro-2-methyl-4-oxo-4H-chromen-8-yl)-1,4-dihydro-pyridine-3-carboxylate

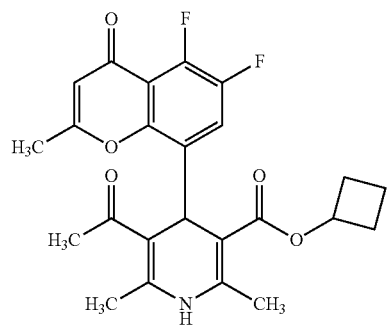

Stage 13a):

5,6-Difluoro-2-methyl-4-oxo-4H-chromene-8-carbaldehyde

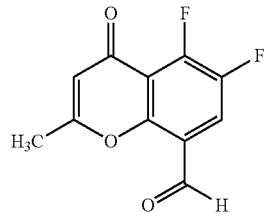

The title compound is obtained in analogy to Example 1, Stage a-e, starting from 4,5-difluoro-2-hydroxyacetophenone.

LC-MS (Method 1): $R_t$=1.42 min; [M+H]$^+$=225
$^1$H-NMR (300 MHz, CDCl$_3$): δ=2.48 (s, 3H), 6.20 (s, 1H), 8.03 (dd, 1H), 10.56 (s, 1H).

Stage 13b):

3-[(5,6-Difluoro-2-methyl-4-oxo-4H-chromen-8-yl)methylene]pentane-2,4-dione

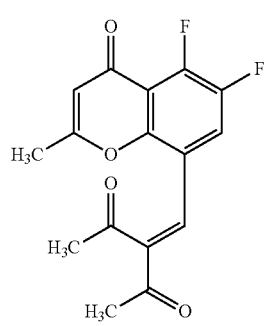

250 mg (1.12 mmol) of 5,6-difluoro-2-methyl-4-oxo-4H-chromene-8-carbaldehyde, 0.14 ml (1.34 mmol) of 2,4-pentanedione and 212.1 mg (1.12 mmol) of para-toluenesulfonic acid are heated in 100 ml of toluene under reflux with a water trap for 10 h. After cooling, 100 ml of ethyl acetate are added, and the reaction mixture is washed with water and with brine. Drying of the organic phase and concentration result in 269.7 mg (79% of theory) of the title compound as beige-coloured crystals.

LC-MS (Method 1): $R_t$=1.65 min; [M+H]$^+$=307
$^1$H-NMR (300 MHz, CDCl$_3$): δ=2.29 (s, 3H), 2.42 (s, 3H), 2.47 (s, 3H), 6.17 (s, 1H), 7.51 (dd, 1H), 7.75 (s, 1H).

Stage 13c):

Cyclobutyl 5-acetyl-2,6-dimethyl-4-(5,6-difluoro-2-methyl-4-oxo-4H-chromen-8-yl)-1,4-dihydro-pyridine-3-carboxylate

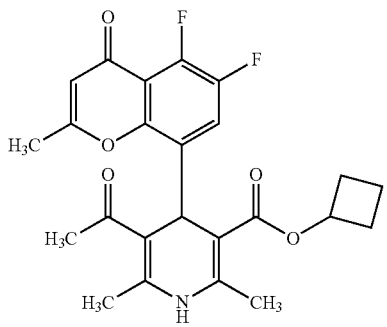

80 mg (0.26 mmol) of 3-[(5,6-difluoro-2-methyl-4-oxo-4H-chromen-8-yl)methylene]pentane-2,4-dione are dissolved with 40.4 mg (0.26 mmol) of cyclobutyl 3-aminocrotonate in 2 ml of 2-propanol and heated under reflux under argon for 12 h. The solvent is removed in vacuo, and the residue is purified by column chromatography (mobile phase: ethyl acetate/cyclohexane 1:2). 31.0 mg (27% of theory) of the title compound are obtained as a yellow solid.

LC-MS (Method 2): $R_t$=2.24 min; [M+H]$^+$=444
$^1$H-NMR (300 MHz, CDCl$_3$): δ=1.21 (m, 1H), 1.62 (m, 2H), 1.76 (m, 2H), 1.94 (m, 1H), 1.94 (s, 3H), 1.97 (s, 3H), 2.04 (s, 3H), 2.05 (s, 3H), 4.96 (quin, 1H), 5.54 (s, 1H), 5.82 (s, 1H), 6.11 (s, 1H), 7.36 (dd, 1H).

Example 14

Ethyl 5-benzoyl-2,6-dimethyl-4-(2-methyl-4-oxo-4H-chromen-8-yl)-1,4-dihydropyridine-3-carboxylate

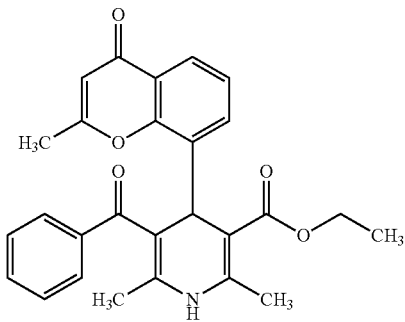

Stage 14a):

2-[(2-Methyl-4-oxo-4H-chromen-8-yl)methylene]-1-phenylbutane-1,3-dione

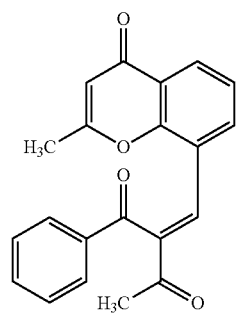

227 mg (1.20 mmol) of 2-methyl-4-oxo-4H-chromene-8-carbaldehyde, 196 mg (1.20 mmol) of 1-phenylbutane-1,3-dione, 17 µl (0.3 mmol) of acetic acid and 17 µl (0.3 mmol) of piperidine in 25 ml of anhydrous dichloromethane are, after addition of molecular sieves, heated under reflux for 24 h. After cooling, the suspension is filtered with suction, and the filtrate is washed successively with saturated sodium bicarbonate solution and saturated brine. The organic phase is dried over magnesium sulfate and concentrated. 353 mg (88% of theory) of a yellow solid are obtained and are directly reacted further.

LC-MS (Method 3): $R_t$=2.06 min; [M+H]$^+$=333.

Stage 14b):

Ethyl 5-benzoyl-2,6-dimethyl-4-(2-methyl-4-oxo-4H-chromen-8-yl)-1,4-dihydropyridine-3-carboxylate

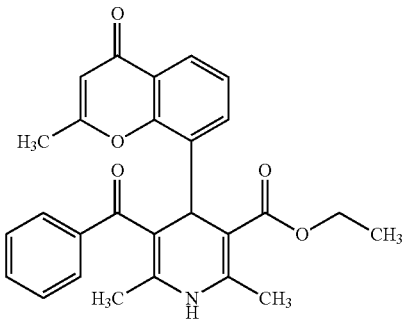

353 mg (1.06 mmol) of 2-[(2-methyl-4-oxo-4H-chromen-8-yl)methylene]-1-phenylbutane-1,3-dione are dissolved with 137 mg (1.06 mmol) of ethyl 3-aminocrotonate in 5 ml of ethanol and heated under reflux under argon for 24 h. The reaction solution is purified by preparative HPLC. Concentration of the product fractions and crystallization from ethyl acetate result in 245 mg (52% of theory) of the title compound as a yellow solid.

LC-MS (Method 3): $R_t$=2.16 min; [M+H]$^+$=444

$^1$H-NMR (300 MHz, DMSO-d$_6$): δ=0.91 (t, 3H), 1.73 (s, 3H), 2.04 (s, 3H), 2.38 (s, 3H), 3.87 (q, 2H), 5.56 (s, 1H), 6.11 (s, 1H), 7.33 (t, 1H), 7.38-7.51 (m, 5H), 7.53 (t, 1H), 7.77 (d, 2H), 8.95 (s, 1H).

Example 15

Cyclobutyl 5-benzoyl-2,6-dimethyl-4-(2-methyl-4-oxo-4H-chromen-8-yl)-1,4-dihydropyridine-3-carboxylate

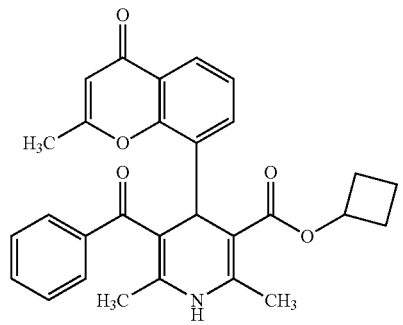

340 mg (1.02 mmol) of 2-[(2-methyl-4-oxo-4H-chromen-8-yl)methylene]-1-phenylbutane-1,3-dione are dissolved with 156 mg (1.8 mmol) of cyclobutyl 3-aminocrotonate in 5 ml of ethanol and heated under reflux under argon for 24 h. The reaction solution is purified by preparative HPLC. Concentration of the product fractions and crystallization from ethyl acetate result in 206 mg (43% of theory) of the title compound as a yellow solid.

LC-MS (Method 2): $R_t$=2.39 min; [M+H]$^+$=470

$^1$H-NMR (300 MHz, DMSO-d$_6$): δ=1.31-1.58 (m, 3H), 1.47 (m, 2H), 1.71 (s, 3H), 1.76 (m, 1H), 1.98 (m, 1H), 2.04 (s, 3H), 2.37 (s, 3H), 4.74 (m, 1H), 5.56 (s, 1H), 6.13 (s, 1H), 7.34 (t, 1H), 7.38-7.51 (m, 5H), 7.53 (t, 1H), 7.78 (d, 2H), 8.94 (s, 1H).

Example 16 n-Propyl 5-benzoyl-2,6-dimethyl-4-(2-methyl-4-oxo-4H-chromen-8-yl)-1,4-dihydropyridine-3-carboxylate

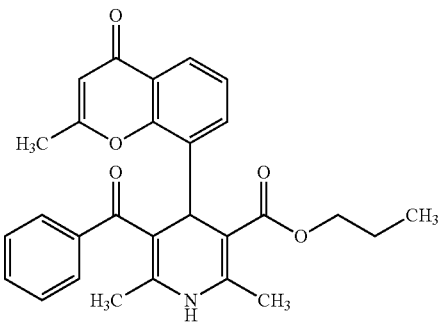

250 mg (0.75 mmol) of 2-[(2-methyl-4-oxo-4H-chromen-8-yl)methylene]-1-phenylbutane-1,3-dione are dissolved with 143 mg (1.0 mmol) of n-propyl 3-aminocrotonate in 5 ml of ethanol and heated under reflux under argon for 24 h. The reaction solution is purified by preparative HPLC.

Concentration of the product fractions and crystallization from ethyl acetate result in 130 mg (38% of theory) of the title compound as a yellow solid.

LC-MS (Method 2): $R_t$=2.35 min; [M+H]$^+$=458

$^1$H-NMR (300 MHz, DMSO-d$_6$): δ=0.57 (t, 3H), 1.31 (m, 2H), 1.73 (s, 3H), 2.00 (s, 3H), 2.40 (s, 3H), 3.79 (t, 2H), 5.57 (s, 1H), 6.10 (s, 1H), 7.33 (t, 1H), 7.38-7.51 (m, 5H), 7.54 (t, 1H), 7.77 (d, 2H), 8.95 (s, 1H).

Example 17

Methyl 5-benzoyl-2,6-dimethyl-4-(2-methyl-4-oxo-4H-chromen-8-yl)-1,4-dihydropyridine-3-carboxylate

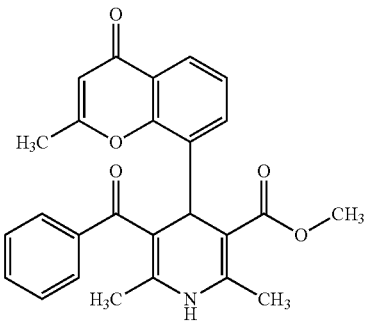

250 mg (0.75 mmol) of 2-[(2-methyl-4-oxo-4H-chromen-8-yl)methylene]-1-phenylbutane-1,3-dione are dissolved with 116 mg (1.0 mmol) of methyl 3-aminocrotonate in 5 ml of ethanol and heated under reflux under argon for 24 h. The reaction solution is purified by preparative HPLC. Concentration of the product fractions and crystallization from ethyl acetate result in 158 mg (49% of theory) of the title compound as a yellow solid.

LC-MS (Method 3): $R_t$=2.05 min; [M+H]$^+$=430

$^1$H-NMR (300 MHz, DMSO-d$_6$): δ=1.71 (s, 3H), 2.06 (s, 3H), 2.38 (s, 3H), 3.44 (s, 3H), 5.52 (s, 1H), 6.10 (s, 1H), 7.33 (t, 1H), 7.40 (m, 5H), 7.51 (m, 1H), 7.78 (d, 2H), 8.97 (s, 1H).

Example 18

Ethyl 5-benzoyl-2-methyl-4-(2-methyl-4-oxo-4H-chromen-8-yl)-6-(trifluoromethyl)-1,4-dihydro-pyridine-3-carboxylate

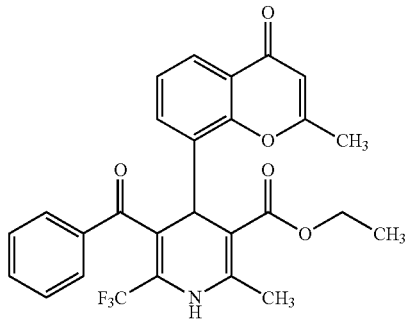

Stage 18a):

4,4,4-Trifluoro-2-[(2-methyl-4-oxo-4H-chromen-8-yl)methylene]-1-phenylbutane-1,3-dione

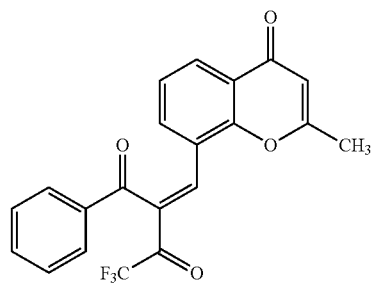

A solution of 200 mg (1.06 mmol) of 2-methyl-4-oxo-4H-chromene-8-carbaldehyde in 20 ml of dichloromethane is mixed with 229.73 mg (1.06 mmol) of 4,4,4-trifluoro-1-phenyl-1,3-butanedione, 0.08 ml (1.33 mmol) of acetic acid and 0.01 ml (0.11 mmol) of piperidine and stirred under reflux with a water trap overnight. After cooling, the mixture is diluted with dichloromethane and washed with saturated sodium chloride solution. The organic phase is dried over sodium sulfate and concentrated. 474 mg (>100% of theory) of the desired product are obtained as a yellow oil which is reacted further without purification.

LC-MS (Method 1): $R_t$=2.12 min;

MS (ESIpos): m/z=404 [M+H$_2$O]$^+$.

Stage 18b):

Ethyl 5-benzoyl-2-methyl-4-(2-methyl-4-oxo-4H-chromen-8-yl)-6-(trifluoromethyl)-1,4-dihydro-pyridine-3-carboxylate

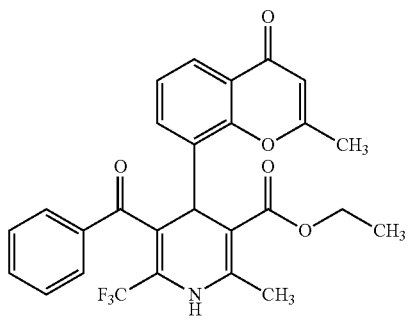

A solution of 410 mg (1.06 mmol) of 4,4,4-trifluoro-2-[(2-methyl-4-oxo-4H-chromen-8-yl)-methylene]-1-phenylbutane-1,3-dione in 10 ml of 2-propanol is mixed with 137.3 mg (1.06 mmol) of ethyl 3-aminocrotonate and stirred under reflux for 12 h. After cooling, the reaction mixture is concentrated, and the residue is taken up in 5 ml of acetic acid and again stirred under reflux for 12 h. The reaction solution is concentrated and the residue is purified by preparative HPLC. 160.3 mg (30.3% of theory) of the title compound are obtained.

LC-MS (Method 3): $R_t$=2.37 min

MS (ESIpos): m/z=498 [M+H]$^+$ $^1$H-NMR (300 MHz, CDCl$_3$): δ=8.0 (d, 1H), 7.58 (d, 4H), 7.47 (t, 1H), 7.35 (t, 1H), 7.32-7.22 (m, 1H), 5.95 (s, 1H), 5.78 (s, 1H), 5.6 (s, 1H), 3.95 (q, 2H), 2.58 (s, 3H), 2.04 (s, 3H), 0.96 (t, 3H).

Example 19

Ethyl 5-acetyl-2-methyl-4-(2-methyl-4-oxo-4H-chromen-8-yl)-6-(trifluoromethyl)-1,4-dihydropyridine-3-carboxylate

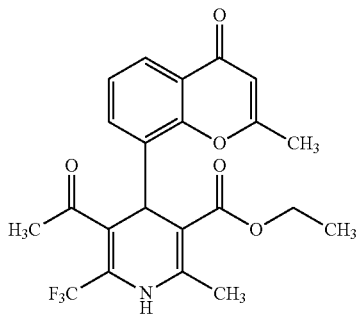

A solution of 2.1 g (11.16 mmol) of 2-methyl-4-oxo-4H-chromene-8-carbaldehyde in 60 ml of 2-propanol is mixed with 1.44 g (11.16 mmol) of ethyl 3-aminocrotonate, 17.2 g (111.6 mmol) of 1,1,1-trifluoro-2,4-pentanedione and 0.96 ml (16.74 mmol) of acetic acid and stirred under reflux for 12 h. After cooling, the reaction mixture is concentrated and the residue is taken up in 30 ml of acetic acid and again stirred under reflux for 12 h. After cooling, the reaction mixture is concentrated, and the residue is purified by preparative HPLC. The product fractions are concentrated and purified again on an Analogix cartridge (mobile phase: cyclohexane/ethyl acetate 2:1). 0.212 g (4.4% of theory) of the title compound are obtained.

LC-MS (Method 1): $R_t$=1.97 min

MS (ESIpos): m/z=436 [M+H]$^+$

¹H-NMR (300 MHz, CDCl₃): δ=8.1 (d, 1H), 7.53 (d, 1H), 7.32 (t, 1H), 6.2 (s, 1H), 5.78 (s, 1H), 5.55 (s, 1H), 4.0 (q, 2H), 2.45 (s, 3H), 2.4 (s, 3H), 2.12 (s, 3H), 1.07 (t, 3H).

Example 20 n-Propyl (4R)-5-acetyl-2,6-dimethyl-4-(2-methyl-4-oxo-4H-chromen-8-yl)-1,4-dihydropyridine-3-carboxylate

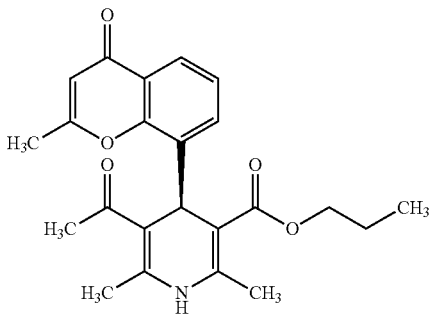

Stage 20a):

(3S)-1-Benzyl-2,5-dioxopyrrolidin-3-yl (4R)-5-acetyl-2,6-dimethyl-4-(2-methyl-4-oxo-4H-chromen-8-yl)-1,4-dihydropyridine-3-carboxylate

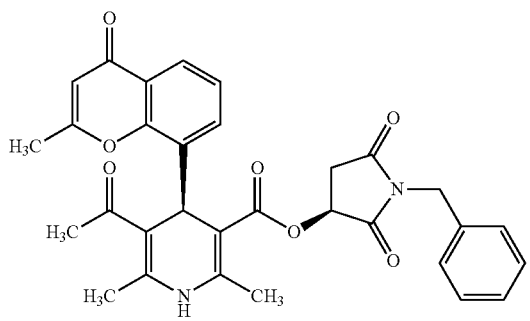

1 g (5.32 mmol) of 2-methyl-4-oxo-4H-chromene-8-carbaldehyde is introduced into 25 ml of 2-propanol and heated under reflux with 0.93 g (9.3 mmol) of 2,4-pentanedione and 1.53 g (5.32 mmol) of (3S)-1-benzyl-2,5-dioxopyrrolidin-3-yl (2E)-3-aminobut-2-enoate [preparation analogous to D. Alker et al., *Eur. J. Med. Chem.* 26 (9), 907-913 (1991), starting from (3S)-1-benzyl-3-hydroxypyrrolidine-2,5-dione] overnight. The solvent is removed in vacuo, and the residue is purified by preparative HPLC. 950 mg (33% of theory) of the desired product are obtained as 4R/4S diastereomer mixture.

The diastereomers are then separated by fractional crystallization from boiling ethanol. In this way, 290 mg (10.5% of theory) of the title compound are obtained as pure 4R-diastereomer.

LC-MS (Method 1): $R_t$=1.89 min; [M+H]⁺=541

¹H-NMR (300 MHz, DMSO-d₆): δ=2.14 (s, 3H), 2.22 (s, 3H), 2.27 (s, 3H), 2.31 (s, 3H), 2.67 (dd, 1H), 3.04 (dd, 1H), 4.52 (q, 2H), 5.42 (s, 1H), 5.49 (dd, 1H), 6.19 (s, 1H), 7.25 (m, 3H), 7.31 (m, 3H), 7.52 (dd, 1H), 7.78 (dd, 1H), 9.14 (s, 1H).

Stage 20b):

(4R)-5-Acetyl-2,6-dimethyl-4-(2-methyl-4-oxo-4H-chromen-8-yl)-1,4-dihydropyridine-3-carboxylic acid

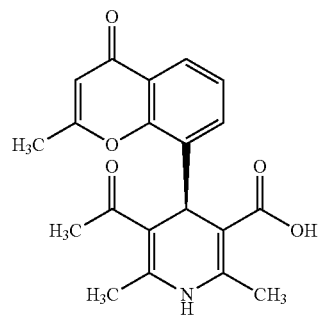

300 mg (0.555 mmol) of (3S)-1-benzyl-2,5-dioxopyrrolidin-3-yl (4R)-5-acetyl-2,6-dimethyl-4-(2-methyl-4-oxo-4H-chromen-8-yl)-1,4-dihydropyridine-3-carboxylate are dissolved in 10 ml of ethyl acetate, and 295.7 mg (1.942 mmol) of DBU are added. The mixture is stirred at room temperature for 8 h. Water is then added, and the pH is adjusted to pH 4-5 with 1 N hydrochloric acid. The aqueous phase is separated off and extracted with ethyl acetate. The combined organic phases are washed with saturated sodium chloride solution. After drying over magnesium sulfate, the solvent is removed in vacuo. The product obtained in this way is reacted further without purification.

LC-MS (Method 1): $R_t$=1.17 min; [M+H]⁺=354.

Stage 20c):

8-[(4R)-3-Acetyl-5-(1H-imidazol-1-ylcarbonyl)-2,6-dimethyl-1,4-dihydropyridin-4-yl]-2-methyl-4H-chromen-4-one

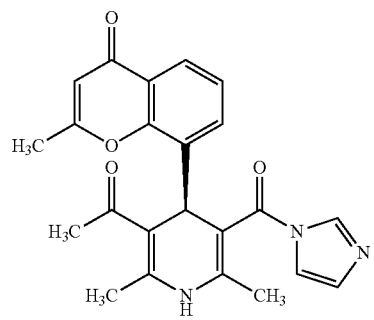

220 mg (0.623 mmol) of (4R)-5-acetyl-2,6-dimethyl-4-(2-methyl-4-oxo-4H-chromen-8-yl)-1,4-dihydropyridine-3-carboxylic acid are dissolved in 20 ml of THF. After addition of 202 mg (1.245 mmol) of 1,1'-carbonyldiimidazole, the mixture is heated at 50° C. for 6 h. The solvent is then removed in vacuo, and the residue is taken up in dichloromethane. After washing with water and saturated sodium chloride solution, the organic phase is dried over magnesium sulfate. The solvent is removed in vacuo, and the residue is purified by preparative HPLC. 90 mg (35.8% of theory) of the title compound are obtained.

LC-MS (Method 1): $R_t$=1.23 min; [M+H]⁺=403.

Stage 20d):

n-Propyl (4R)-5-acetyl-2,6-dimethyl-4-(2-methyl-4-oxo-4H-chromen-8-yl)-1,4-dihydropyridine-3-carboxylate

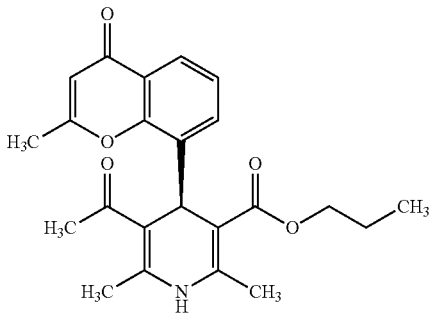

75 mg (0.186 mmol) of 8-[(4R)-3-acetyl-5-(1H-imidazol-1-ylcarbonyl)-2,6-dimethyl-1,4-dihydro-pyridin-4-yl]-2-methyl-4H-chromen-4-one are heated under reflux in 1.5 ml of 1-propanol under argon for 3 h. The solvent is removed in vacuo, and the residue is purified by preparative HPLC. 34 mg (46% of theory) of the title compound are obtained.

LC-MS (Method 1): $R_t$=1.79 min; $[M+H]^+$=396

$^1$H-NMR (300 MHz, DMSO-$d_6$): δ=0.66 (t, 3H), 1.42 (m, 2H), 2.17 (s, 3H), 2.22 (s, 3H), 2.29 (s, 3H), 2.39 (s, 3H), 3.86 (m, 2H), 5.45 (s, 1H), 6.22 (s, 1H), 7.32 (t, 1H), 7.56 (dd, 1H), 7.81 (dd, 1H), 8.99 (s, 1H).

Example 21 n-Propyl 5-acetyl-4-(5-chloro-2-methyl-4-oxo-4H-chromen-8-yl)-2,6-dimethyl-1,4-dihydro-pyridine-3-carboxylate

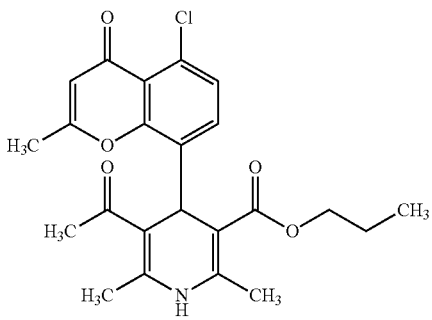

Stage 21a):

1-(2-Hydroxy-3-methylphenyl)-2-(triphenylphosphoranylidene)ethanone

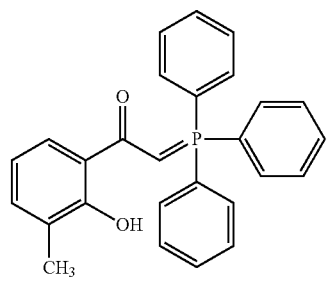

206.8 ml (330.9 mmol) of a 1.6 molar n-butyllithium solution in n-hexane are slowly added to 97.3 g (240.7 mmol) of methyltriphenylphosphonium iodide in 800 ml of absolute THF under argon. The mixture is stirred at room temperature for 3 h. Then 20.0 g (120.3 mmol) of methyl 2-hydroxy-3-methylbenzoate in 200 ml of absolute THF are added dropwise to the reaction mixture. The mixture is stirred at 60° C. for 3 h. After cooling to room temperature, the precipitated lithium iodide is filtered off. The filtrate is concentrated in vacuo, and the residue is recrystallized from methanol. 27 g (56% of theory) of the title compound are obtained.

LC-MS (Method 2): $R_t$=2.12 min; $[M+H]^+$=411.

Stage 21b):

2,8-Dimethyl-4H-chromen-4-one

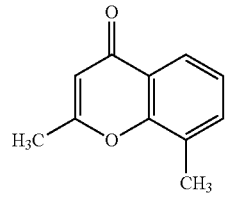

27.5 g (67 mmol) of 1-(2-hydroxy-3-methylphenyl)-2-(triphenylphosphoranylidene)ethanone in 200 ml of absolute toluene are heated to reflux. 13.7 g (134 mmol) of acetic anhydride and 11.1 g (141 mmol) of pyridine are slowly added dropwise to this solution. The reaction mixture is then heated under reflux for 6 h. After cooling to room temperature, the solution is washed with saturated sodium carbonate solution and dried over sodium sulfate. The solvent is removed in vacuo, and the residue is purified by column chromatography (mobile phase: cyclohexane/ethyl acetate 7:3→4:6). 7.5 g (64% of theory) of the title compound are obtained.

LC-MS (Method 3): $R_t$=1.99 min; $[M+H]^+$=175

$^1$H-NMR (300 MHz, DMSO-$d_6$): δ=2.41 (s, 3H), 2.44 (s, 3H), 6.24 (s, 3H), 7.34 (t, 1H), 7.63 (dd, 1H), 7.83 (dd, 1H).

Stage 21c):

2,8-Dimethyl-5-nitro-4H-chromen-4-one

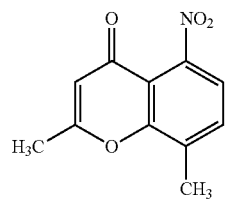

2 g (11.48 mmol) of 2,8-dimethyl-4H-chromen-4-one are dissolved in 15 ml of concentrated sulfuric acid and, at 0° C., 0.7 g (11.48 mmol) of fuming nitric acid is added, during which the temperature should not exceed 5° C. The mixture is then stirred at room temperature for 1 h. The reaction mixture is poured into ice-water, whereupon a colorless solid precipitates. This is filtered off and washed several times with water and ice-cold methanol. 2.3 g (90.8% of theory) of the title compound are obtained.

LC-MS (Method 2): $R_t$=1.74 min; $[M+H]^+$=220

$^1$H-NMR (300 MHz, DMSO-$d_6$): δ=2.41 (s, 3H), 2.48 (s, 3H), 6.34 (s, 1H), 7.65 (d, 1H), 7.80 (d, 1H).

Stage 21d):

5-Amino-2,8-dimethyl-4H-chromen-4-one

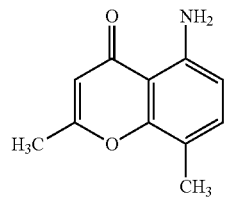

1.78 g (8.12 mmol) of 2,8-dimethyl-5-nitro-4H-chromen-4-one are heated with 9.16 g (40.6 mmol) of tin(II) chloride dihydrate in 70 ml of ethyl acetate at 70° C. overnight. After cooling to room temperature, the reaction mixture is brought to pH 9-10 with saturated sodium bicarbonate solution. After filtration through kieselguhr, the organic phase is separated off, and the aqueous phase is extracted several times with ethyl acetate. The combined organic phases are washed with saturated sodium chloride solution. After drying over sodium sulfate, the solvent is removed in vacuo. 1.5 g (99% of theory) of the title compound are obtained.

LC-MS (Method 1): $R_t$=1.74 min; $[M+H]^+$=190

$^1$H-NMR (300 MHz, DMSO-$d_6$): δ=2.17 (s, 3H), 2.30 (s, 3H), 6.00 (s, 1H), 6.42 (d, 1H), 7.17 (br. s, 2H), 7.18 (d, 1H).

Stage 21e):

5-Chloro-2,8-dimethyl-4H-chromen-4-one

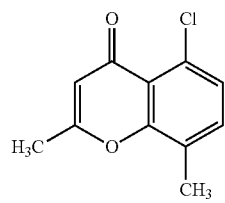

0.42 g (3.9 mmol) of copper(II) chloride and 0.45 g (3.96 mmol) of tert-butyl nitrite are introduced into 20 ml of acetonitrile and heated to 65° C. 0.5 g (2.63 mmol) of 5-amino-2,8-dimethyl-4H-chromen-4-one in 10 ml of acetonitrile are slowly added dropwise to this suspension. The reaction mixture is stirred at 65° C. for 10 min and then allowed to cool to room temperature, and subsequently 5 ml of concentrated hydrochloric acid are added. After extraction with diethyl ether, the combined organic phases are washed with water and dried over sodium sulfate. After removal of the solvent in vacuo, the remaining crude product is purified by preparative HPLC. 0.27 g (50% of theory) of the title compound is obtained.

LC-MS (Method 3): $R_t$=2.02 min; $[M+H]^+$=209

$^1$H-NMR (300 MHz, DMSO-$d_6$): δ=2.36 (s, 3H), 2.38 (s, 3H), 6.20 (s, 1H), 7.35 (d, 1H), 7.57 (d, 1H).

Stage 21f):

5-Chloro-8-(dibromomethyl)-2-methyl-4H-chromen-4-one

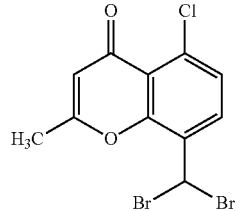

120 mg (0.57 mmol) of 5-chloro-2,8-dimethyl-4H-chromen-4-one are dissolved in 20 ml of tetrachloromethane and heated with 225 mg (1.26 mmol) of N-bromosuccinimide and 9.4 mg (0.06 mmol) of 2,2'-azobis-2-methylpropanenitrile under reflux overnight. After cooling to room temperature, the precipitated solid is filtered off and discarded. The filtrate is concentrated in vacuo, and the residue is reacted further without purification.

LC-MS (Method 1): $R_t$=2.25 min; $[M+H]^+$=365.

Stage 21g):

5-Chloro-2-methyl-4-oxo-4H-chromene-8-carbaldehyde

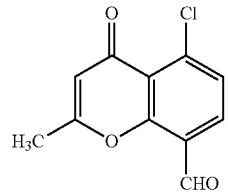

210 mg (0.57 mmol) of 5-chloro-8-(dibromomethyl)-2-methyl-4H-chromen-4-one are heated with 147 mg (1.2 mmol) of N-methylmorpholine N-oxide with the addition of molecular sieves in 15 ml of acetonitrile under reflux overnight. After filtration through kieselguhr, the solvent is removed in vacuo and the residue is purified by preparative HPLC. 22 mg (17% of theory) of the title compound are obtained.

LC-MS (Method 3): $R_t$=1.71 min; $[M+H]^+$=223

$^1$H-NMR (300 MHz, DMSO-$d_6$): δ=2.54 (s, 3H), 6.30 (s, 1H), 7.56 (d, 1H), 8.07 (d, 1H), 10.53 (s, 1H).

Stage 21 h):

n-Propyl 5-acetyl-4-(5-chloro-2-methyl-4-oxo-4H-chromen-8-yl)-2,6-dimethyl-1,4-dihydro-pyridine-3-carboxylate

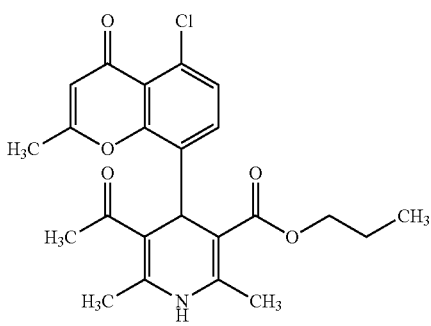

40 mg (0.18 mmol) of 5-chloro-2-methyl-4-oxo-4H-chromene-8-carbaldehyde are dissolved with 31 mg (0.18 mmol) of 2,4-pentanedione, 25 mg (0.18 mmol) of n-propyl 3-aminocrotonate and 11 mg (0.18 mmol) of acetic acid in 2 ml of 2-propanol and heated under reflux under argon for 10 h. The solvent is removed in vacuo, and the residue is purified by preparative HPLC. 33 mg (42% of theory) of the title compound are obtained as a yellow solid.

LC-MS (Method 2): $R_t$=2.71 min; $[M+H]^+$=430

$^1$H-NMR (300 MHz, DMSO-$d_6$): δ=0.69 (t, 3H), 1.43 (m, 2H), 2.16 (s, 3H), 2.22 (s, 3H), 2.28 (s, 3H), 2.35 (s, 3H), 3.86 (m, 2H), 5.41 (s, 1H), 6.19 (s, 1H), 7.35 (d, 1H), 7.46 (d, 1H), 8.98 (s, 1H).

The racemate obtained in this way is separated into the enantiomers by HPLC on chiral phase (Method 4):
Enantiomer 1: $R_t$=3.16 min;
Enantiomer 2: $R_t$=3.84 min.

Example 22

Ethyl 5-(4-methoxybenzoyl)-2,6-dimethyl-4-(2-methyl-4-oxo-4H-chromen-8-yl)-1,4-dihydro-pyridine-3-carboxylate

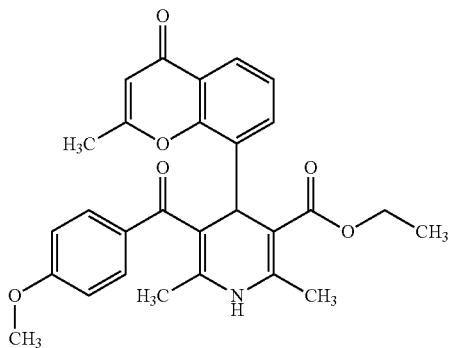

Stage 22a):

1-(4-Methoxyphenyl)-2-[(2-methyl-4-oxo-4H-chromen-8-yl)methylene]butane-1,3-dione

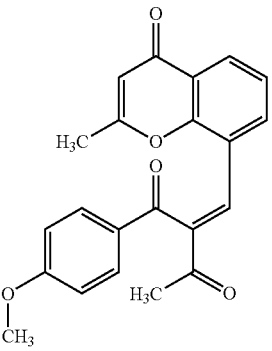

250 mg (1.32 mmol) of 2-methyl-4-oxo-4H-chromene-8-carbaldehyde are dissolved with 281 mg (1.46 mmol) of 1-(4-methoxyphenyl)butane-1,3-dione, 100 mg (1.66 mmol) of acetic acid and 11 mg (0.13 mmol) of piperidine in 5 ml of dichloromethane and, after addition of molecular sieves, heated under reflux under argon for 4 h. The solvent is removed after filtration in vacuo. 480 mg (99% of theory) of the title compound are obtained and are employed without further purification in the next stage.

LC-MS (Method 2): $R_t$=2.12 min; $[M+H]^+$=363.

Stage 22b):

Ethyl 5-(4-methoxybenzoyl)-2,6-dimethyl-4-(2-methyl-4-oxo-4H-chromen-8-yl)-1,4-dihydro-pyridine-3-carboxylate

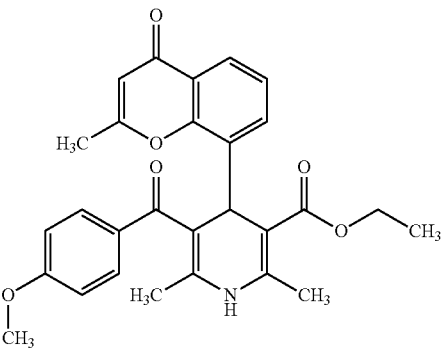

230 mg (0.63 mmol) of 1-(4-methoxyphenyl)-2-[(2-methyl-4-oxo-4H-chromen-8-yl)methylene]-butane-1,3-dione are heated with 81.9 mg (0.63 mmol) of ethyl 3-aminocrotonate in 5 ml of 2-propanol under reflux overnight. The solvent is removed in vacuo, and the residue is purified by preparative HPLC. 50 mg (16% of theory) of the title compound are obtained.

LC-MS (Method 1): $R_t$=1.99 min; $[M+H]^+$=474

$^1$H-NMR (300 MHz, DMSO-$d_6$): δ=0.91 (t, 3H), 1.68 (s, 3H), 2.06 (s, 3H), 2.38 (s, 3H), 3.78 (s, 3H), 3.87 (q, 2H), 5.53 (s, 1H), 6.11 (s, 1H), 6.95 (d, 2H), 7.34 (t, 1H), 7.45 (dd, 1H), 7.47 (d, 2H), 7.77 (dd, 1H), 8.82 (s, 1H).

Example 23 n-Propyl 5-(4-methoxybenzoyl)-2,6-dimethyl-4-(2-methyl-4-oxo-4H-chromen-8-yl)-1,4-dihydro-pyridine-3-carboxylate

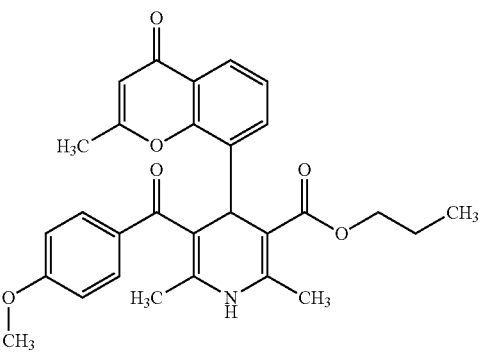

230 mg (0.63 mmol) of 1-(4-methoxyphenyl)-2-[(2-methyl-4-oxo-4H-chromen-8-yl)methylene]-butane-1,3-dione are heated with 90 mg (0.63 mmol) of n-propyl 3-aminocrotonate in 5 ml of 2-propanol under reflux overnight. The solvent is removed in vacuo, and the residue is purified by preparative HPLC. 74 mg (24% of theory) of the title compound are obtained.

LC-MS (Method 1): $R_t$=2.11 min; $[M+H]^+$=488

$^1$H-NMR (300 MHz, DMSO-$d_6$): δ=0.56 (t, 3H), 1.31 (m, 2H), 1.68 (s, 3H), 2.01 (s, 3H), 2.41 (s, 3H), 3.78 (s, 3H), 3.80 (t, 2H), 5.54 (s, 1H), 6.09 (s, 1H), 6.95 (d, 2H), 7.34 (t, 1H), 7.44 (dd, 1H), 7.47 (d, 2H), 7.75 (dd, 1H), 8.83 (s, 1H).

Example 24

Ethyl 5-(3-methoxybenzoyl)-2,6-dimethyl-4-(2-methyl-4-oxo-4H-chromen-8-yl)-1,4-dihydro-pyridine-3-carboxylate

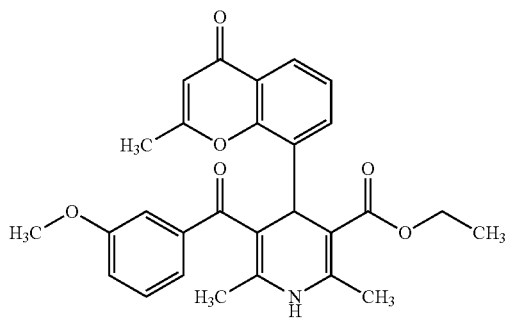

Stage 24a):

1-(3-Methoxyphenyl)-2-[(2-methyl-4-oxo-4H-chromen-8-yl)methylene]butane-1,3-dione

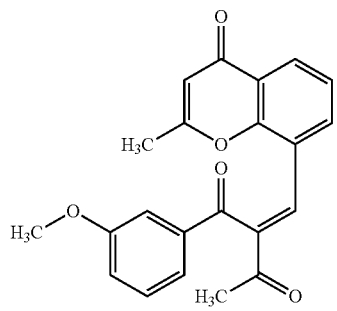

250 mg (1.32 mmol) of 2-methyl-4-oxo-4H-chromene-8-carbaldehyde are dissolved with 280.9 mg (1.46 mmol) of 1-(3-methoxyphenyl)butane-1,3-dione, 99.7 mg (1.66 mmol) of acetic acid and 11.3 mg (0.13 mmol) of piperidine in 5 ml of dichloromethane and, after addition of molecular sieves, heated under reflux under argon for 4 h. The solvent is removed after filtration in vacuo. 479 mg (98% of theory) of the title compound are obtained and are employed without further purification in the next stage.

LC-MS (Method 2): $R_t$=2.18 min; [M+H]$^+$=363.

Stage 24b):

Ethyl 5-(3-methoxybenzoyl)-2,6-dimethyl-4-(2-methyl-4-oxo-4H-chromen-8-yl)-1,4-dihydro-pyridine-3-carboxylate

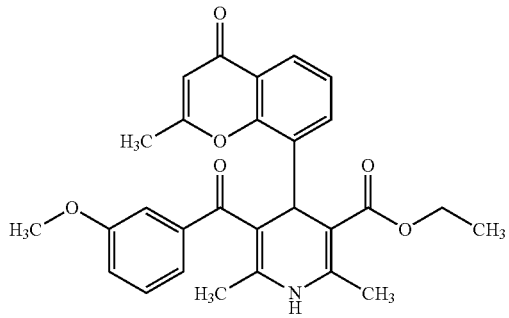

245 mg (0.67 mmol) of 1-(3-methoxyphenyl)-2-[(2-methyl-4-oxo-4H-chromen-8-yl)methylene]-butane-1,3-dione are heated with 87 mg (0.67 mmol) of ethyl 3-aminocrotonate in 5 ml of 2-propanol under reflux overnight. The solvent is removed in vacuo, and the residue is purified by preparative HPLC. 102 mg (32% of theory) of the title compound are obtained.

LC-MS (Method 3): $R_t$=2.18 min; [M+H]+=474

$^1$H-NMR (300 MHz, DMSO-d$_6$): δ=0.92 (t, 3H), 1.72 (s, 3H), 2.09 (s, 3H), 2.37 (s, 3H), 3.68 (s, 3H), 3.88 (q, 2H), 5.55 (s, 1H), 6.12 (s, 1H), 6.87 (m, 1H), 7.00 (d, 1H), 7.09 (dd, 1H), 7.33 (m, 2H), 7.45 (dd, 1H), 7.79 (dd, 1H), 8.93 (s, 1H).

Example 25 n-Propyl 5-(3-methoxybenzoyl)-2,6-dimethyl-4-(2-methyl-4-oxo-4H-chromen-8-yl)-1,4-dihydro-pyridine-3-carboxylate

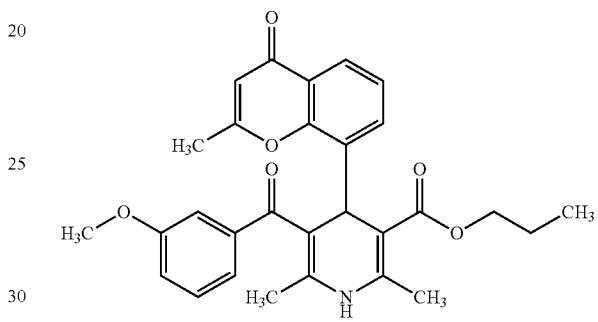

245 mg (0.67 mmol) of 1-(3-methoxyphenyl)-2-[(2-methyl-4-oxo-4H-chromen-8-yl)methylene]-butane-1,3-dione are heated with 96 mg (0.67 mmol) of n-propyl 3-aminocrotonate in 5 ml of 2-propanol under reflux overnight. The solvent is removed in vacuo, and the residue is purified by preparative HPLC. 94 mg (28% of theory) of the title compound are obtained.

LC-MS (Method 3): $R_t$=2.30 min; [M+H]$^+$=488

$^1$H-NMR (300 MHz, DMSO-d$_6$): δ=0.58 (t, 3H), 1.31 (m, 2H), 1.72 (s, 3H), 2.05 (s, 3H), 2.40 (s, 3H), 3.68 (s, 3H), 3.80 (t, 2H), 5.57 (s, 1H), 6.11 (s, 1H), 6.91 (m, 1H), 7.04 (d, 1H), 7.1 (dd, 1H), 7.34 (m, 2H), 7.44 (dd, 1H), 7.77 (dd, 1H), 8.95 (s, 1H).

Example 26 n-Propyl 5-(2-methoxybenzoyl)-2,6-dimethyl-4-(2-methyl-4-oxo-4H-chromen-8-yl)-1,4-dihydro-pyridine-3-carboxylate

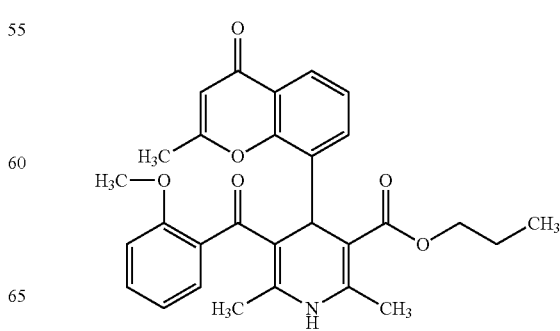

Stage 26a):

1-(2-Methoxyphenyl)-2-[(2-methyl-4-oxo-4H-chromen-8-yl)methylene]butane-1,3-dione

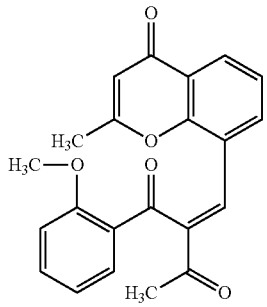

250 mg (1.32 mmol) of 2-methyl-4-oxo-4H-chromene-8-carbaldehyde are dissolved with 280.9 mg (1.46 mmol) of 1-(2-methoxyphenyl)butane-1,3-dione, 99.7 mg (1.66 mmol) of acetic acid and 11.3 mg (0.13 mmol) of piperidine in 5 ml of dichloromethane and, after addition of molecular sieves, heated under reflux under argon for 4 h. The solvent is removed after filtration in vacuo. 480 mg (99% of theory) of the title compound are obtained and are employed without further purification in the next stage.

LC-MS (Method 2): $R_t$=2.08 min; [M+H]$^+$=363.

Stage 26b):

n-Propyl 5-(2-methoxybenzoyl)-2,6-dimethyl-4-(2-methyl-4-oxo-4H-chromen-8-yl)-1,4-dihydro-pyridine-3-carboxylate

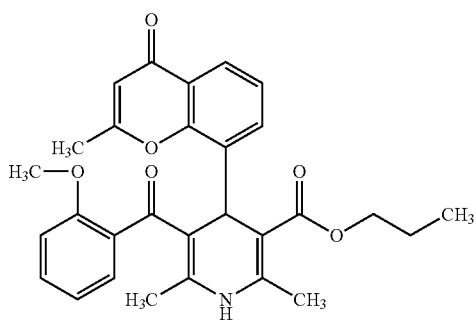

240 mg (0.62 mmol) of 1-(2-methoxyphenyl)-2-[(2-methyl-4-oxo-4H-chromen-8-yl)methylene]-butane-1,3-dione are heated with 94 mg (0.62 mmol) of n-propyl 3-aminocrotonate in 5 ml of 2-propanol under reflux overnight. The solvent is removed in vacuo, and the residue is purified by preparative HPLC. 108 mg (33% of theory) of the title compound are obtained.

LC-MS (Method 3): $R_t$=2.21 min; [M+H]$^+$=488

$^1$H-NMR (300 MHz, DMSO-d$_6$): δ=0.64 (t, 3H), 1.37 (m, 2H), 1.89 (s, 3H), 2.21 (s, 3H), 2.29 (s, 3H), 3.50 (s, 3H), 3.81 (m, 2H), 5.43 (s, 1H), 6.15 (s, 1H), 6.85 (m, 2H), 6.99 (d, 1H), 7.27 (m, 2H), 7.36 (m, 1H), 7.78 (dd, 1H), 8.99 (s, 1H).

Example 27

Cyclobutylmethyl 5-acetyl-2,6-dimethyl-4-(2-methyl-4-oxo-4H-chromen-8-yl)-1,4-dihydro-pyridine-3-carboxylate

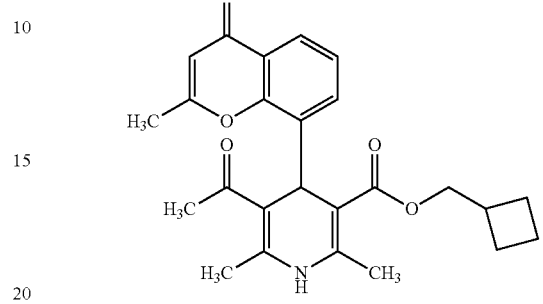

Stage 27a):

Cyclobutylmethyl 3-oxobutanoate

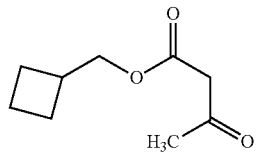

4.61 ml (35.17 mmol) of 2,2,6-trimethyl-1,3-dioxin-4-one and 3.32 ml (35.17 mmol) of cyclobutylmethanol are stirred in 20 ml of toluene under reflux under argon for 4 h. The solvent is then removed in vacuo. 7.51 g of a yellow oil are obtained and are employed without further purification.

$^1$H-NMR (300 MHz, DMSO-d$_6$): δ=1.65-1.92 (m, 6H), 2.17 (s, 3H), 2.36 (m, 1H), 3.60 (s, 2H), 4.03 (d, 2H).

Stage 27b):

Cyclobutylmethyl 2-[(2-methyl-4-oxo-4H-chromen-8-yl)methylene]-3-oxobutanoate

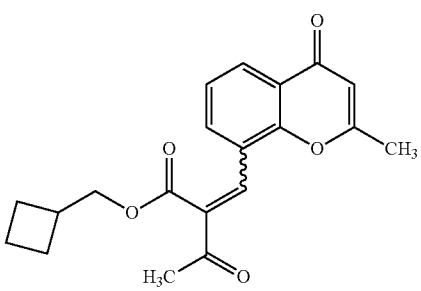

700 mg (3.72 mmol) of 2-methyl-4-oxo-4H-chromene-8-carbaldehyde, 760 mg (4.46 mmol) of cyclobutylmethyl 3-oxobutanoate, 53 µl (0.93 mmol) of acetic acid and 92 µl (0.93 mmol) of piperidine in 25 ml of anhydrous dichloromethane are heated after addition of 4 Å molecular sieves (1.5 g) under reflux for 24 h. After cooling, the suspension is filtered with suction and the filtrate is washed successively with saturated sodium bicarbonate solution and saturated sodium chloride solution. The organic phase is dried over magnesium sulfate and concentrated. The residue is purified by preparative HPLC. 962 mg (76% of theory) of the title compound are obtained as an E/Z mixture.

LC-MS (Method 1): $R_t$=2.12 and 2.29 min; [M+H]$^+$=341.

Stage 27c):

Cyclobutylmethyl 5-acetyl-2,6-dimethyl-4-(2-methyl-4-oxo-4H-chromen-8-yl)-1,4-dihydro-pyridine-3-carboxylate

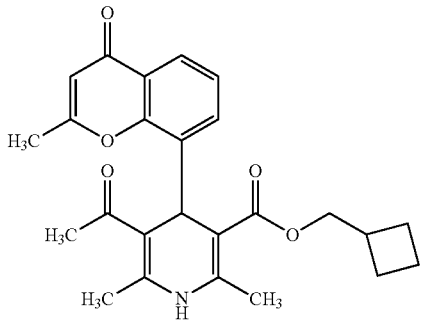

960 mg (2.82 mmol) of cyclobutylmethyl 2-[(2-methyl-4-oxo-4H-chromen-8-yl)methylene]-3-oxobutanoate are dissolved with 279 mg (2.82 mmol) of 4-aminopent-3-en-2-one in 10 ml of ethanol and heated under reflux under argon for 24 h. The solvent is removed in vacuo, and the residue is purified by preparative HPLC. Concentration of the product fractions and crystallization from ethyl acetate result in 532 mg (44% of theory) of the title compound as a white solid.

LC-MS (Method 2): $R_t$=2.26 min; [M+H]$^+$=422

$^1$H-NMR (300 MHz, DMSO-d$_6$): δ=1.51 (m, 2H), 1.62-1.88 (m, 4H), 2.17 (s, 3H), 2.21 (s, 3H), 2.29 (s, 3H), 2.39 (s, 3H), 2.41 (m, 1H), 3.89 (m, 2H), 5.43 (s, 1H), 6.22 (s, 1H), 7.32 (t, 1H), 7.54 (t, 1H), 7.80 (d, 2H), 9.00 (s, 1H).

Example 28

(1S)-1-Methylpropyl (4R)-5-acetyl-2,6-dimethyl-4-(2-methyl-4-oxo-4H-chromen-8-yl)-1,4-dihydropyridine-3-carboxylate

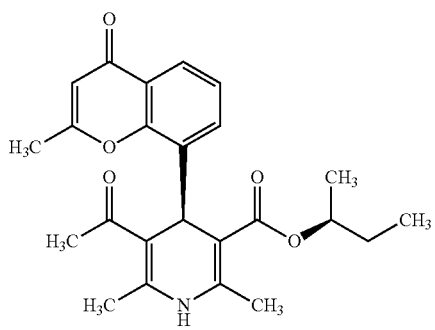

The title compound is obtained in analogy to Example 20, Stage 20d), from 75 mg (0.186 mmol) of 8-[(4R)-3-acetyl-5-(1H-imidazol-1-ylcarbonyl)-2,6-dimethyl-1,4-dihydropyridin-4-yl]-2-methyl-4H-chromen-4-one and 1.5 ml (20 mmol) of (S)-(+)-2-butanol.

Yield: 56 mg (73% of theory)

LC-MS (Method 1): $R_t$=1.85 min; [M+H]$^+$=410

$^1$H-NMR (300 MHz, DMSO-d$_6$): δ=0.80 (m, 6H), 1.46 (m, 2H), 2.17 (s, 3H), 2.22 (s, 3H), 2.28 (s, 3H), 2.39 (s, 3H), 4.64 (m, 1H), 5.43 (s, 1H), 6.23 (s, 1H), 7.32 (t, 1H), 7.57 (dd, 1H), 7.80 (dd, 1H), 8.94 (s, 1H).

Example 29

(1R)-1-Methylpropyl (4R)-5-acetyl-2,6-dimethyl-4-(2-methyl-4-oxo-4H-chromen-8-yl)-1,4-dihydropyridine-3-carboxylate

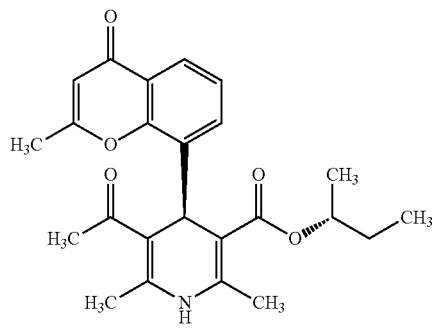

The title compound is obtained in analogy to Example 20, Stage 20d), from 75 mg (0.186 mmol) of 8-[(4R)-3-acetyl-5-(1H-imidazol-1-ylcarbonyl)-2,6-dimethyl-1,4-dihydropyridin-4-yl]-2-methyl-4H-chromen-4-one and 1.5 ml (20 mmol) of (R)-(−)-2-butanol.

Yield: 36 mg (47% of theory)

LC-MS (Method 1): $R_t$=1.81 min; [M+H]$^+$=410

$^1$H-NMR (300 MHz, DMSO-d$_6$): δ=0.30 (m, 3H), 1.10 (d, 3H), 1.27 (m, 2H), 2.17 (s, 3H), 2.21 (s, 3H), 2.30 (s, 3H), 2.40 (s, 3H), 4.64 (m, 1H), 5.43 (s, 1H), 6.23 (s, 1H), 7.32 (t, 1H), 7.57 (dd, 1H), 7.80 (dd, 1H), 8.94 (s, 1H).

Example 30

2,2,2-Trifluoro-1-methylethyl 5-acetyl-2,6-dimethyl-4-(2-methyl-4-oxo-4H-chromen-8-yl)-1,4-dihydropyridine-3-carboxylate

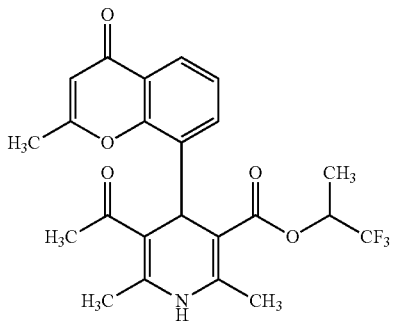

Stage 30a):

2,2,2-Trifluoro-1-methylethyl 3-oxobutanoate

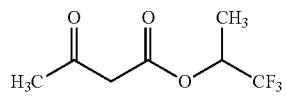

0.3 g (2.6 mmol) of 1,1,1-trifluoropropan-2-ol are dissolved in 5 ml of tetrahydrofuran, and 26 mg (0.23 mmol) of triethylamine are added. 0.26 g (3.1 mmol) of diketene in 5 ml of tetrahydrofuran are added dropwise. The reaction mixture is then heated under reflux for 4 h. The solvent is removed in vacuo. The resulting crude product (0.4 g, 76% of theory) is employed without further purification in the next stage.

Stage 30b):

2,2,2-Trifluoro-1-methylethyl 3-aminobut-2-enoate

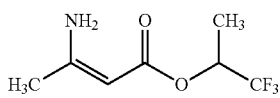

2.4 g (12 mmol) of 2,2,2-trifluoro-1-methylethyl 3-oxobutanoate are heated with 1.8 g (24.6 mmol) of ammonium acetate and 0.6 g (11 mmol) of acetic acid with the addition of molecular sieves at 110° C. for 5 h. After cooling to room temperature, the reaction mixture is mixed with water and extracted with ethyl acetate. Washing of the organic phase with water and saturated sodium chloride solution is followed by drying over magnesium sulfate. After filtration, the solvent is removed in vacuo. The resulting crude product (1.5 g, 77% purity, 77% of theory) is employed without further purification in the next stage.

GC-MS (Method 6): $R_t$=4.13 min; $[M+H]^+$=198.

Stage 30c):

2,2,2-Trifluoro-1-methylethyl 5-acetyl-2,6-dimethyl-4-(2-methyl-4-oxo-4H-chromen-8-yl)-1,4-dihydro-pyridine-3-carboxylate

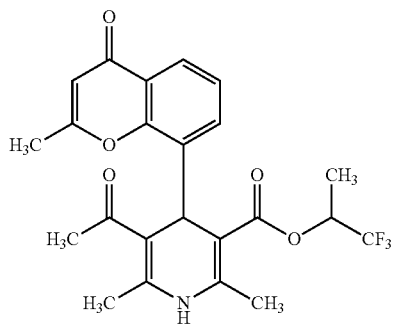

100 mg (0.53 mmol) of 2-methyl-4-oxo-4H-chromene-8-carbaldehyde are dissolved with 93 mg (0.93 mmol) of 2,4-pentanedione, 105 mg (0.53 mmol) of 2,2,2-trifluoro-1-methylethyl-3-aminobut-2-enoate and 23 mg (0.37 mmol) of acetic acid in 5 ml of 2-propanol and heated under reflux under argon for 16 h. The solvent is removed in vacuo and the residue is purified by preparative HPLC, separating the diastereomers. A total of 84 mg (32% of theory) of the title compound are obtained as a yellow solid.

Diastereomer 1:

LC-MS (Method 1): $R_t$=2.01 min; $[M+H]^+$=450

$^1$H-NMR (300 MHz, DMSO-$d_6$): δ=0.98 (d, 3H), 2.19 (s, 3H), 2.21 (s, 3H), 2.32 (s, 3H), 2.38 (s, 3H), 5.32 (m, 1H), 5.44 (s, 1H), 6.21 (s, 1H), 7.30 (t, 1H), 7.56 (dd, 1H), 7.80 (dd, 1H), 9.18 (s, 1H).

Diastereomer 2:

LC-MS (Method 1): $R_t$=2.05 min; $[M+H]^+$=450

$^1$H-NMR (300 MHz, DMSO-$d_6$): δ=1.02 (d, 3H), 2.18 (s, 3H), 2.22 (s, 3H), 2.31 (s, 3H), 2.37 (s, 3H), 5.32 (m, 1H), 5.40 (s, 1H), 6.22 (s, 1H), 7.33 (t, 1H), 7.56 (dd, 1H), 7.80 (dd, 1H), 9.19 (s, 1H).

Example 31

Cyclopropylmethyl 5-acetyl-2,6-dimethyl-4-(2-methyl-4-oxo-4H-chromen-8-yl)-1,4-dihydro-pyridine-3-carboxylate

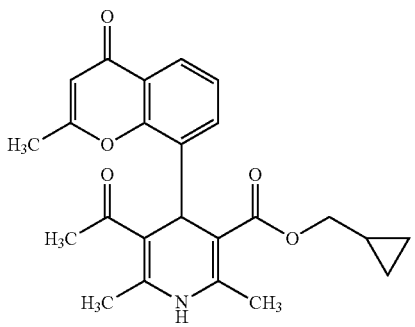

Stage 31a):

Cyclopropylmethyl 3-oxobutanoate

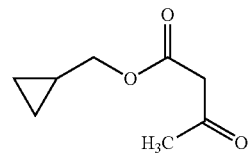

1.84 ml (14.06 mmol) of 2,2,6-trimethyl-1,3-dioxin-4-one and 1.11 ml (14.06 mmol) of cyclopropylmethanol are stirred in 15 ml of toluene under reflux under argon for 4 h. The solvent is then removed in vacuo. 2.06 g of a yellow oil are obtained and are employed without further purification.

$^1$H-NMR (300 MHz, DMSO-$d_6$): δ=0.26 (m, 2H), 0.51 (m, 2H), 1.08 (m, 1H), 2.18 (s, 3H), 3.60 (s, 2H), 3.89 (d, 2H).

Stage 31b):

Cyclopropylmethyl 2-[(2-methyl-4-oxo-4H-chromen-8-yl)methylene]-3-oxobutanoate

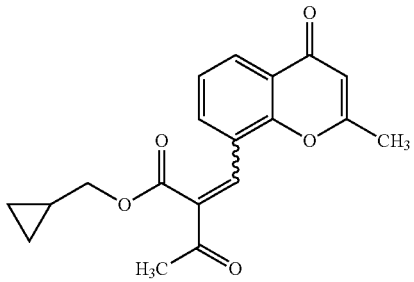

500 mg (2.65 mmol) of 2-methyl-4-oxo-4H-chromene-8-carbaldehyde, 798 mg (2.65 mmol) of cyclopropylmethyl 3-oxobutanoate, 38 µl (0.66 mmol) of acetic acid and 66 µl (0.66 mmol) of piperidine in 25 ml of anhydrous dichloromethane are heated after addition of 4 Å molecular sieves (1.5 g) under reflux for 24 h. After cooling, the suspension is filtered with suction and the filtrate is washed successively with saturated sodium bicarbonate solution and saturated sodium chloride solution. The organic phase is dried over magnesium sulfate and concentrated. The residue is purified by preparative HPLC. 650 mg (74% of theory) of the title compound are obtained as an E/Z mixture.

LC-MS (Method 1): $R_t$=1.91 and 2.07 min; [M+H]$^+$=327.

Stage 31c):

Cyclopropylmethyl 5-acetyl-2,6-dimethyl-4-(2-methyl-4-oxo-4H-chromen-8-yl)-1,4-dihydro-pyridine-3-carboxylate

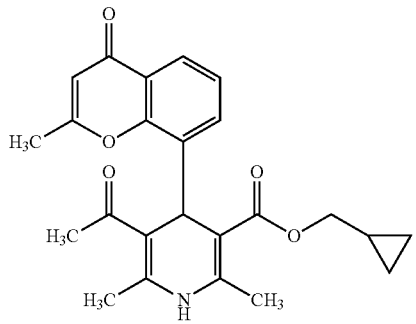

648 mg (1.98 mmol) of cyclopropylmethyl 2-[(2-methyl-4-oxo-4H-chromen-8-yl)methylene]-3-oxobutanoate are dissolved with 196 mg (1.98 mmol) of 4-aminopent-3-en-2-one in 10 ml of ethanol and heated under reflux under argon for 24 h. The solvent is removed in vacuo, and the residue is purified by preparative HPLC. Concentration of the product fractions and crystallization from ethyl acetate result in 327 mg (41% of theory) of the title compound as a white solid.

LC-MS (Method 2): R=2.17 min; [M+H]$^+$=408

$^1$H-NMR (300 MHz, DMSO-d$_6$): δ=0.03 (m, 1H), 0.11 (m, 1H), 0.36 (m, 2H), 0.92 (m, 1H), 2.16 (s, 3H), 2.23 (s, 3H), 2.29 (s, 3H), 2.38 (s, 3H), 3.73 (d, 2H), 5.45 (s, 1H), 6.21 (s, 1H), 7.32 (t, 1H), 7.59 (t, 1H), 7.80 (d, 2H), 8.98 (s, 1H).

Example 32

Methyl 2,6-dimethyl-4-(2-methyl-4-oxo-4H-chromen-8-yl)-5-(4-methylpentanoyl)-1,4-dihydro-pyridine-3-carboxylate

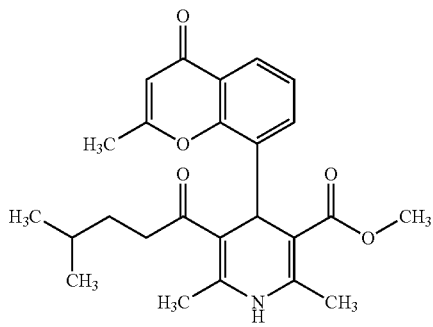

Stage 32a):

2-Amino-7-methyloct-2-en-4-one

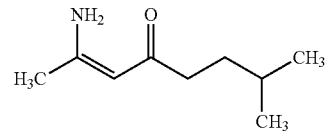

3-Methyl-5-(3-methylbutyl)isoxazole (3.90 g, 25.5 mmol) [synthesis analogous to C. Kashima et al., *Bull. Chem. Soc. Jpn.* 46, 310-313 (1973)] is introduced into 80 ml of ethanol, platinum(IV) oxide catalyst (390 mg, 1.72 mmol) is added, and the mixture is then hydrogenated under atmospheric pressure hydrogen for 2 h (slightly exothermic reaction). The catalyst is filtered off, the filtrate is concentrated, and the residue is purified by chromatography on a Biotage 40M cartridge (mobile phase: isohexane/ethyl acetate 3:1). The product fractions are concentrated. The resulting residue is an oil, which crystallizes after a short time. Drying in vacuo results in 3.41 g (86% of theory) of the title compound.

$^1$H-NMR (400 MHz, CDCl$_3$): δ=9.71 (br. s, 1H), 5.02 (s, 1H), 4.95 (br. s, 1H), 2.26 (m, 2H), 1.91 (s, 3H), 1.63-1.42 (m, 3H), 0.89 (d, 6H)

GC-MS (Method 6): $R_t$=6.21 min; MS (CIpos): m/z=156 [M+H]$^+$.

Stage 32b):

Methyl 2-[(2-methyl-4-oxo-4H-chromen-8-yl)methylene]-3-oxobutanoate

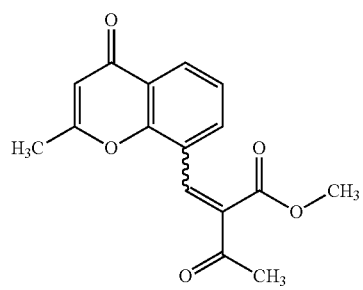

1 g (5.31 mmol) of 2-methyl-4-oxo-4H-chromene-8-carbaldehyde, 680 mg (5.84 mmol) of methyl 3-oxobutanoate, 456 μl (7.97 mmol) of acetic acid and 105 μl (1.06 mmol) of piperidine in 50 ml of anhydrous dichloromethane are stirred under reflux with a water trap for 24 h. After cooling, the reaction solution is diluted with dichloromethane (100 ml) and washed successively with saturated sodium bicarbonate solution and saturated sodium chloride solution. The organic phase is dried over magnesium sulfate and concentrated. The residue is recrystallized from isopropanol. 1.43 g (94% of theory) of the title compound are obtained as an E/Z mixture.

LC-MS (Method 3): $R_t$=1.77 and 1.85 min; [M+H]$^+$=287

$^1$H-NMR (300 MHz, DMSO-d$_6$): δ=2.33 (s, 1.5H), 2.42 (s, 1.5H), 2.43 (s, 1.5H), 2.54 (s, 1.5H), 3.67 (m, 1.5H), 3.83 (s, 1.5H), 6.32 (s, 0.5H), 6.33 (s, 0.5H), 7.47 (t, 0.5H), 7.52 (t, 0.5H), 7.65 (dd, 0.5H), 7.65 (dd, 0.5H), 7.98 (s, 0.5H), 8.07 (dd, 0.5H), 8.08 (s, 0.5H), 8.09 (dd, 0.5H).

Stage 32c):

Methyl 2,6-dimethyl-4-(2-methyl-4-oxo-4H-chromen-8-yl)-5-(4-methylpentanoyl)-1,4-dihydro-pyridine-3-carboxylate

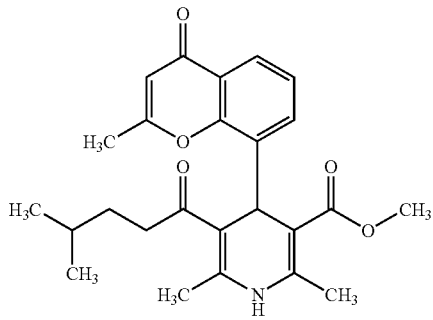

50 mg (0.175 mmol) of methyl 2-[(2-methyl-4-oxo-4H-chromen-8-yl)methylene]-3-oxobutanoate are dissolved with 35 mg (0.227 mmol) of 2-amino-7-methyloct-2-en-4-one in 3 ml of ethanol and heated under reflux under argon for 24 h. The reaction mixture is purified by preparative HPLC. Concentration of the fractions results in 45.3 mg (61% of theory) of the title compound as a white solid.

LC-MS (Method 2): $R_t$=2.46 min; $[M+H]^+$=424

$^1$H-NMR (300 MHz, DMSO-$d_6$): δ=0.70 (d, 3H), 0.73 (d, 3H), 1.16 (m, 1H), 1.22-1.38 (m, 2H), 2.18 (m, 1H), 2.20 (s, 3H), 2.26 (m+s, 4H), 2.40 (s, 3H), 2.61 (m, 1H), 3.49 (m, 3H), 5.49 (s, 1H), 6.23 (s, 1H), 7.33 (t, 1H), 7.55 (dd, 1H), 7.81 (dd, 1H), 8.96 (s, 1H).

Example 33

Methyl 5-(3-cyclobutylpropanoyl)-2,6-dimethyl-4-(2-methyl-4-oxo-4H-chromen-8-yl)-1,4-dihydro-pyridine-3-carboxylate

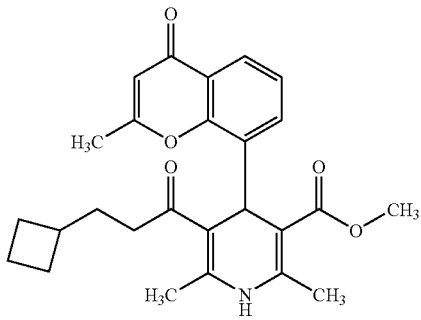

Stage 33a):

5-Amino-1-cyclobutylhex-4-en-3-one

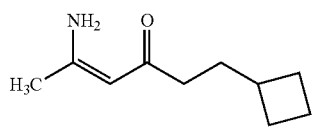

Preparation takes place in analogy to Example 32 (Stage 32a) starting from 5-(2-cyclobutylethyl)-3-methylisoxazole [obtainable in analogy to C. Kashima et al., *Bull. Chem. Soc. Jpn.* 46, 310-313 (1973)].

GC-MS (Method 6): $R_t$=7.82 min; MS (CIpos): m/z=168 $[M+H]^+$.

Stage 33b):

Methyl 5-(3-cyclobutylpropanoyl)-2,6-dimethyl-4-(2-methyl-4-oxo-4H-chromen-8-yl)-1,4-dihydro-pyridine-3-carboxylate

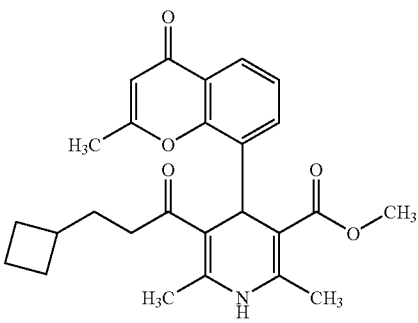

50 mg (0.175 mmol) of methyl 2-[(2-methyl-4-oxo-4H-chromen-8-yl)methylene]-3-oxobutanoate are dissolved with 38 mg (0.227 mmol) of 5-amino-1-cyclobutylhex-4-en-3-one in 3 ml of ethanol and heated under reflux under argon for 24 h. The reaction mixture is purified by preparative HPLC. Concentration of the fractions results in 43 mg (56% of theory) of the title compound as a white solid.

LC-MS (Method 2): $R_t$=2.53 min; $[M+H]^+$=436

$^1$H-NMR (300 MHz, DMSO-$d_6$): δ=1.33-1.58 (m, 4H), 1.63-1.87 (m, 4H), 1.91-2.05 (m, 2H), 2.18 (m, 1H), 2.20 (s, 3H), 2.26 (s, 3H), 2.40 (s, 3H), 3.49 (m, 3H), 5.47 (s, 1H), 6.23 (s, 1H), 7.33 (t, 1H), 7.54 (dd, 1H), 7.81 (dd, 2H), 8.95 (s, 1H).

Example 34

Methyl 5-(cyclobutylacetyl)-2,6-dimethyl-4-(2-methyl-4-oxo-4H-chromen-8-yl)-1,4-dihydro-pyridine-3-carboxylate

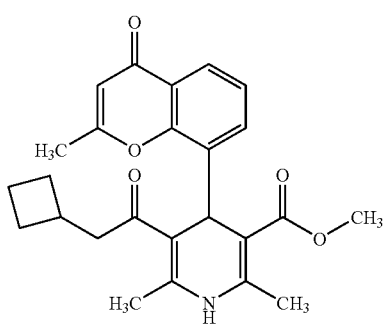

Stage 34a):

4-Amino-1-cyclobutylpent-3-en-2-one

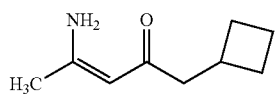

Preparation takes place in analogy to Example 32 (Stage 32a) starting from 5-(cyclobutylmethyl)-3-methylisoxazole [obtainable in analogy to C. Kashima et al., *Bull. Chem. Soc. Jpn.* 46, 310-313 (1973)].

GC-MS (Method 6): $R_t$=7.03 min; MS (CIpos): m/z=154 $[M+H]^+$.

Stage 34b):

Methyl 5-(cyclobutylacetyl)-2,6-dimethyl-4-(2-methyl-4-oxo-4H-chromen-8-yl)-1,4-dihydro-pyridine-3-carboxylate

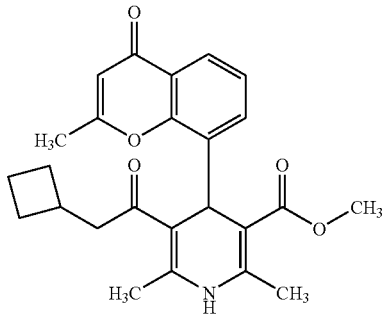

50 mg (0.175 mmol) of methyl 2-[(2-methyl-4-oxo-4H-chromen-8-yl)methylene]-3-oxobutanoate are dissolved with 34.7 mg (0.227 mmol) of 4-amino-1-cyclobutylpent-3-en-2-one in 3 ml of ethanol and heated under reflux under argon for 24 h. The reaction mixture is purified by preparative HPLC. Concentration of the fractions results in 36 mg (43% of theory) of the title compound as a white solid.

LC-MS (Method 2): $R_t$=2.38 min; [M+H]$^+$=422

$^1$H-NMR (300 MHz, DMSO-d$_6$): δ=1.38 (m, 1H), 1.48 (m, 1H), 1.57-1.79 (m, 2H), 1.85 (m, 1H), 1.94 (m, 1H), 2.18 (s, 3H), 2.27 (m+s, 4H), 2.41 (m+s, 4H), 2.80 (m, 1H), 3.49 (s, 3H), 5.48 (s, 1H), 6.23 (s, 1H), 7.33 (t, 1H), 7.55 (dd, 1H), 7.81 (dd, 1H), 8.94 (s, 1H).

Example 35

Methyl 2,6-dimethyl-5-(3-methylbutanoyl)-4-(2-methyl-4-oxo-4H-chromen-8-yl)-1,4-dihydro-pyridine-3-carboxylate

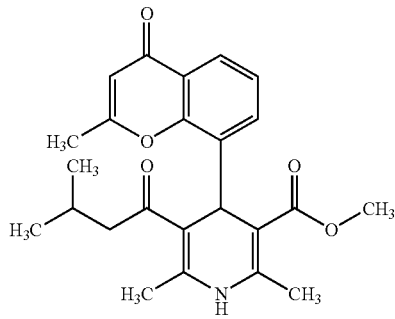

Stage 35a):

2-Amino-6-methylhept-2-en-4-one

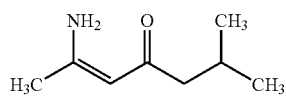

Preparation takes place in analogy to Example 32 (Stage 32a) starting from 4.50 g (32.3 mmol) of 5-isobutyl-3-methylisoxazole [obtainable in analogy to C. Kashima et al., *Bull. Chem. Soc. Jpn.* 46, 310-313 (1973)].

Yield: 4.02 g (88% of theory)

GC-MS (Method 6): $R_t$=5.30 min; MS (CIpos): m/z=142 [M+H]$^+$.

Stage 35b):

Methyl 2,6-dimethyl-5-(3-methylbutanoyl)-4-(2-methyl-4-oxo-4H-chromen-8-yl)-1,4-dihydro-pyridine-3-carboxylate

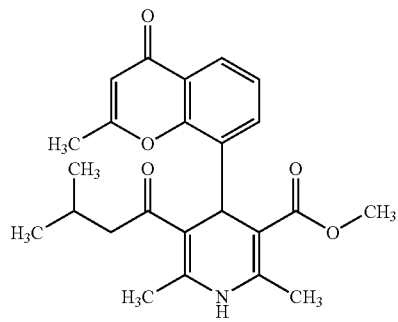

50 mg (0.175 mmol) of methyl 2-[(2-methyl-4-oxo-4H-chromen-8-yl)methylene]-3-oxobutanoate are dissolved with 34.7 mg (0.227 mmol) of 2-amino-6-methylhept-2-en-4-one in 3 ml of ethanol and heated under reflux under argon for 24 h. The reaction mixture is purified by preparative HPLC. Concentration of the fractions results in 36 mg (43% of theory) of the title compound as a white solid.

LC-MS (Method 1): $R_t$=1.97 min; [M+H]$^+$=410

$^1$H-NMR (300 MHz, DMSO-d$_6$): δ=0.65 (d, 3H), 0.78 (d, 3H), 1.92 (m, 1H), 2.18 (m+s, 4H), 2.27 (m+s, 4H), 2.41 (s, 3H), 2.57 (m, 1H), 3.49 (m, 3H), 5.50 (s, 1H), 6.24 (s, 1H), 7.33 (t, 1H), 7.54 (dd, 1H), 7.81 (dd, 1H), 8.95 (s, 1H).

Example 36

Methyl 5-(cyclopentylacetyl)-2,6-dimethyl-4-(2-methyl-4-oxo-4H-chromen-8-yl)-1,4-dihydro-pyridine-3-carboxylate

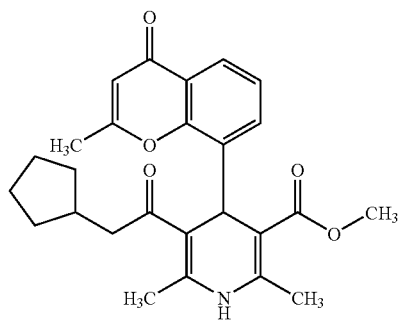

Stage 36a):

4-Amino-1-cyclopentylpent-3-en-2-one

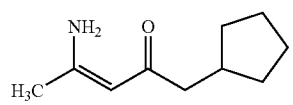

Preparation takes place in analogy to Example 32 (Stage 32a) starting from 5-(cyclopentylmethyl)-3-methylisoxazole [obtainable in analogy to C. Kashima et al., *Bull. Chem. Soc. Jpn.* 46, 310-313 (1973)].

$^1$H-NMR (300 MHz, DMSO-d$_6$): δ=1.07 (m, 2H), 1.50 (m, 4H), 1.67 (m, 2H), 1.81 (s, 3H), 2.11 (m, 3H), 4.87 (s, 1H), 7.37 (br. s, 1H), 9.51 (br. s, 1H).

Stage 36b):

Methyl 5-(cyclopentylacetyl)-2,6-dimethyl-4-(2-methyl-4-oxo-4H-chromen-8-yl)-1,4-dihydro-pyridine-3-carboxylate

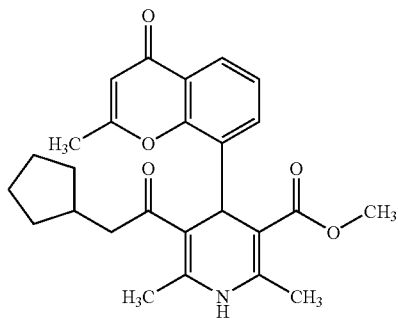

50 mg (0.175 mmol) of methyl 2-[(2-methyl-4-oxo-4H-chromen-8-yl)methylene]-3-oxobutanoate are dissolved with 38 mg (0.227 mmol) of 4-amino-1-cyclopentylpent-3-en-2-one in 3 ml of ethanol and heated under reflux under argon for 24 h. The reaction mixture is purified by preparative HPLC. Concentration of the fractions results in 43 mg (55% of theory) of the title compound as a white solid.

LC-MS (Method 3): R$_t$=2.34 min; [M+H]$^+$=436

$^1$H-NMR (300 MHz, DMSO-d$_6$): δ=0.81 (m, 1H), 0.95 (m, 1H), 1.08 (m, 1H), 1.32-1.71 (m, 5H), 2.03 (m, 1H), 2.18 (s, 3H), 2.27 (s, 3H), 2.31 (m, 1H), 2.41 (s, 3H), 2.69 (dd, 1H), 3.48 (m, 3H), 5.50 (s, 1H), 6.23 (s, 1H), 7.33 (t, 1H), 7.54 (dd, 1H), 7.81 (dd, 1H), 8.93 (s, 1H).

Example 37

Methyl 2,6-dimethyl-5-(4-methylbenzoyl)-4-(2-methyl-4-oxo-4H-chromen-8-yl)-1,4-dihydro-pyridine-3-carboxylate

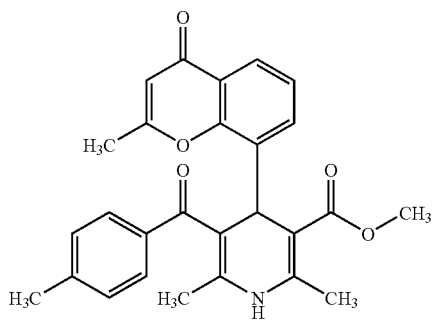

Stage 37a):

3-Methyl-5-(4-methylphenyl)isoxazole

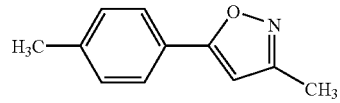

6.23 ml (57.39 mmol) of phenyl isocyanate are added dropwise at room temperature to a solution of 5 g (43.04 mmol) of 1-ethynyl-4-methylbenzene, 1 ml (14.34 mmol) of nitroethane and 0.4 ml (2.87 mmol) of triethylamine in 100 ml of benzene. The reaction mixture is then stirred under reflux for 12 h. After cooling, the suspension is mixed with water (50 ml) and stirred at room temperature for a further 4 h. The precipitate is filtered off with suction and washed with benzene (10 ml). The organic phase of the filtrate is separated off, dried with magnesium sulfate and concentrated. The residue is purified by column chromatography on silica gel (mobile phase: cyclohexane/ethyl acetate 6:1). 1.13 g (46% of theory) of the title compound are obtained as a colourless oil.

$^1$H-NMR (300 MHz, DMSO-d$_6$): δ=2.27 (s, 3H), 2.36 (s, 3H), 6.80 (s, 1H), 7.33 (d, 2H), 7.71 (d, 2H).

Stage 37b):

3-Amino-1-(4-methylphenyl)but-2-en-1-one

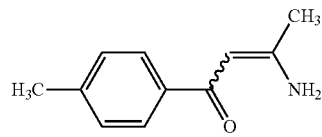

3-Methyl-5-(4-methylphenyl)isoxazole (1 g, 5.77 mmol) is introduced into 20 ml of ethanol, platinum(IV) oxide catalyst (100 mg) is added, and the mixture is then hydrogenated under atmospheric hydrogen for 12 h. The catalyst is filtered off and the filtrate is concentrated. 1.02 g (100% of theory) of the title compound are obtained as a white solid.

LC-MS (Method 1): R$_t$=1.61 min; [M+H]$^+$=176.

Stage 37c):

Methyl 2,6-dimethyl-5-(4-methylbenzoyl)-4-(2-methyl-4-oxo-4H-chromen-8-yl)-1,4-dihydro-pyridine-3-carboxylate

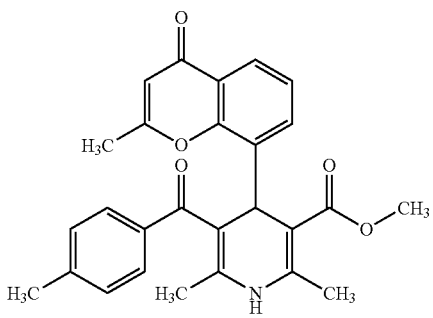

848 mg (4.50 mmol) of 2-methyl-4-oxo-4H-chromene-8-carbaldehyde are dissolved with 523 mg (4.50 mmol) of methyl 3-oxobutanoate, 790 mg (4.50 mmol) of 3-amino-1-(4-methylphenyl)but-2-en-1-one and 387 μl (6.72 mmol) of acetic acid in 10 ml of 2-propanol and heated under reflux under argon for 30 h. The solvent is removed in vacuo, and the residue is purified by preparative HPLC. 961 mg (44% of theory) of the title compound are obtained as a yellow solid.

LC-MS (Method 3): $R_t$=2.17 min; $[M+H]^+$=444

$^1$H-NMR (300 MHz, CDCl$_3$): δ=1.75 (s, 3H), 2.03 (s, 3H), 2.35 (s, 3H), 2.50 (s, 3H), 3.54 (m, 3H), 5.59 (s, 1H), 5.70 (s, 1H), 5.97 (s, 1H), 7.11 (d, 2H), 7.27 (t, 1H), 7.42 (d, 2H), 7.45 (dd, 1H), 7.98 (dd, 1H).

Example 38

Ethyl 2,6-dimethyl-5-(4-methylbenzoyl)-4-(2-methyl-4-oxo-4H-chromen-8-yl)-1,4-dihydro-pyridine-3-carboxylate

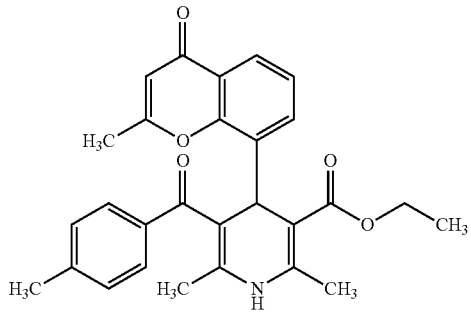

100 mg (0.53 mmol) of 2-methyl-4-oxo-4H-chromene-8-carbaldehyde are dissolved with 69 mg (0.53 mmol) of ethyl 3-oxobutanoate, 93 mg (0.53 mmol) of 3-amino-1-(4-methylphenyl)but-2-en-1-one and 3 μl (0.05 mmol) of acetic acid in 5 ml of 2-propanol and heated under reflux under argon for 30 h. The solvent is removed in vacuo, and the residue is purified by preparative HPLC. 180 mg (74% of theory) of the title compound are obtained as a yellow solid.

LC-MS (Method 1): $R_t$=2.12 min; $[M+H]^+$=458

$^1$H-NMR (300 MHz, DMSO-d$_6$): δ=0.90 (t, 3H), 1.69 (s, 3H), 2.05 (s, 3H), 2.35 (s, 3H), 2.38 (s, 3H), 3.86 (q, 2H), 5.54 (s, 1H), 6.11 (s, 1H), 7.21 (d, 2H), 7.33 (t, 1H), 7.35 (d, 2H), 7.45 (dd, 1H), 7.77 (dd, 1H), 8.88 (s, 1H).

Example 39

Propyl 2,6-dimethyl-5-(4-methylbenzoyl)-4-(2-methyl-4-oxo-4H-chromen-8-yl)-1,4-dihydro-pyridine-3-carboxylate

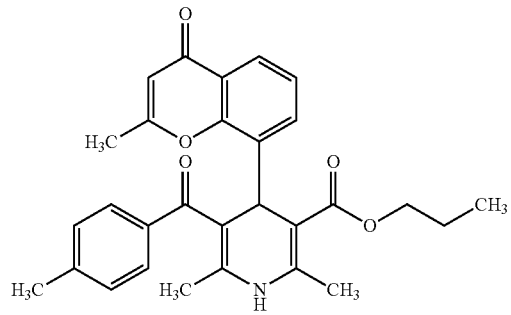

100 mg (0.53 mmol) of 2-methyl-4-oxo-4H-chromene-8-carbaldehyde are dissolved with 76 mg (0.53 mmol) of n-propyl 3-oxobutanoate, 93 mg (0.24 mmol) of 3-amino-1-(4-methylphenyl)but-2-en-1-one and 3 μl (0.05 mmol) of acetic acid in 5 ml of 2-propanol and heated under reflux under argon for 30 h. The solvent is removed in vacuo, and the residue is purified by preparative HPLC. 173 mg (69% of theory) of the title compound are obtained as a yellow solid.

LC-MS (Method 3): $R_t$=2.41 min; $[M+H]^+$=472

$^1$H-NMR (300 MHz, DMSO-d$_6$): δ=0.57 (t, 3H), 1.30 (m, 2H), 1.69 (s, 3H), 2.01 (s, 3H), 2.36 (s, 3H), 2.40 (s, 3H), 3.79 (t, 2H), 5.55 (s, 1H), 6.10 (s, 1H), 7.21 (d, 2H), 7.34 (t, 1H), 7.37 (d, 2H), 7.44 (dd, 1H), 7.76 (dd, 1H), 8.89 (s, 1H).

Example 40

Ethyl 2,6-dimethyl-5-(4-fluorobenzoyl)-4-(2-methyl-4-oxo-4H-chromen-8-yl)-1,4-dihydropyridine-3-carboxylate

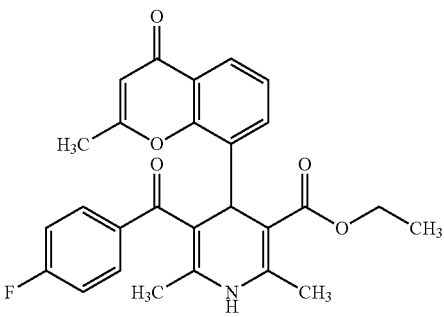

Stage 40a):

3-Methyl-5-(4-fluorophenyl)isoxazole

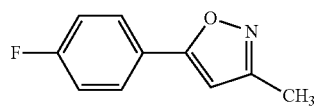

2.41 ml (22.19 mmol) of phenyl isocyanate are added dropwise at room temperature to a solution of 2 g (16.64 mmol) of 1-ethynyl-4-fluorobenzene, 0.4 ml (5.55 mmol) of nitroethane and 0.15 ml (1.11 mmol) of triethylamine in 40 ml of benzene. The reaction mixture is then stirred under reflux for 12 h. After cooling, the suspension is mixed with water (20 ml) and stirred at room temperature for a further 4 h. The precipitate is filtered off with suction and washed with benzene (10 ml). The organic phase of the filtrate is separated off, dried with magnesium sulfate and concentrated. The residue is purified by column chromatography on silica gel (mobile phase: cyclohexane/ethyl acetate 9:1). 0.62 g (63% of theory) of the title compound is obtained as a colorless oil.

$^1$H-NMR (300 MHz, DMSO-d$_6$): δ=2.28 (s, 3H), 6.87 (s, 1H), 7.37 (t, 2H), 7.89 (dd, 2H).

Stage 40b):

3-Amino-1-(4-fluorophenyl)but-2-en-1-one

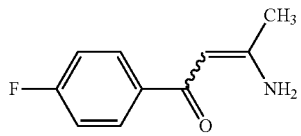

3-Methyl-5-(4-fluorophenyl)isoxazole (620 mg, 3.49 mmol) is introduced into 16 ml of ethanol, platinum(IV) oxide catalyst (62 mg) is added, and the mixture is then hydrogenated under atmospheric pressure hydrogen for 12 h. The catalyst is filtered off and the filtrate is concentrated. 573 mg (91% of theory) of the title compound are obtained as a white solid.

LC-MS (Method 3): $R_t$=1.63 min; [M+H]$^+$=180.

Stage 40c):

Ethyl 2,6-dimethyl-5-(4-fluorobenzoyl)-4-(2-methyl-4-oxo-4H-chromen-8-yl)-1,4-dihydropyridine-3-carboxylate

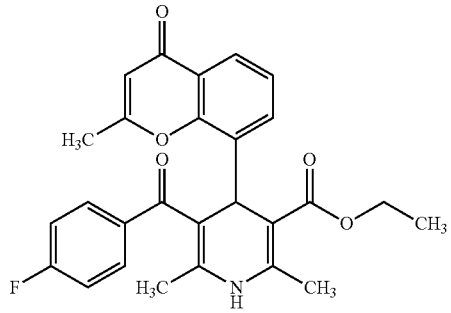

210 mg (1.11 mmol) of 2-methyl-4-oxo-4H-chromene-8-carbaldehyde are dissolved with 145 mg (1.11 mmol) of ethyl 3-oxobutanoate, 200 mg (1.11 mmol) of 3-amino-1-(4-fluorophenyl)but-2-en-1-one and 6 µl (0.11 mmol) of acetic acid in 10 ml of 2-propanol and heated under reflux under argon for 30 h. The solvent is removed in vacuo, and the residue is purified by preparative HPLC. 172 mg (33% of theory) of the title compound are obtained as a yellow solid.

LC-MS (Method 2): $R_t$=2.30 min; [M+H]$^+$=462

$^1$H-NMR (300 MHz, DMSO-d$_6$): δ=0.91 (t, 3H), 1.73 (s, 3H), 2.07 (s, 3H), 2.38 (s, 3H), 3.86 (q, 2H), 5.52 (s, 1H), 6.13 (s, 1H), 7.25 (t, 2H), 7.33 (t, 1H), 7.45 (dd, 1H), 7.52 (dd, 2H), 7.78 (dd, 1H), 8.96 (s, 1H).

Example 41

Propyl 2,6-dimethyl-5-(4-fluorobenzoyl)-4-(2-methyl-4-oxo-4H-chromen-8-yl)-1,4-dihydro-pyridine-3-carboxylate

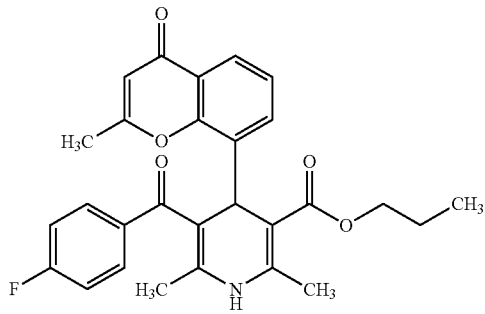

110 mg (0.54 mmol) of 2-methyl-4-oxo-4H-chromene-8-carbaldehyde are dissolved with 78 mg (0.54 mmol) of n-propyl 3-oxobutanoate, 97 mg (0.54 mmol) of 3-amino-1-(4-fluorophenyl)but-2-en-1-one and 6 µl (0.05 mmol) of acetic acid in 10 ml of 2-propanol and heated under reflux under argon for 30 h. The solvent is removed in vacuo, and the residue is purified by preparative HPLC. 228 mg (87% of theory) of the title compound are obtained as a yellow solid.

LC-MS (Method 2): $R_t$=2.42 min; [M+H]$^+$=476

$^1$H-NMR (300 MHz, DMSO-d$_6$): δ=0.57 (t, 3H), 1.31 (m, 2H), 1.73 (s, 3H), 2.03 (s, 3H), 2.41 (s, 3H), 3.79 (t, 2H), 5.54 (s, 1H), 6.12 (s, 1H), 7.26 (t, 2H), 7.34 (t, 1H), 7.45 (dd, 1H), 7.55 (dd, 2H), 7.78 (dd, 1H), 8.97 (s, 1H).

Example 42

Ethyl 2,6-dimethyl-5-[4-(trifluoromethyl)benzoyl]-4-(2-methyl-4-oxo-4H-chromen-8-yl)-1,4-dihydropyridine-3-carboxylate

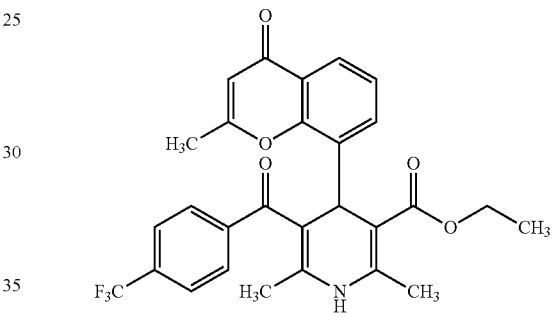

Stage 42a):

3-Methyl-5-[4-(trifluoromethyl)phenyl]isoxazole

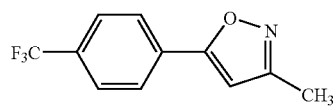

4.25 ml (39.18 mmol) of phenyl isocyanate are added dropwise at room temperature to a solution of 5 g (29.38 mmol) of 1-ethynyl-4-(trifluoromethyl)benzene, 0.7 ml (9.79 mmol) of nitroethane and 0.27 ml (1.95 mmol) of triethylamine in 40 ml of benzene. The reaction mixture is subsequently stirred under reflux for 12 h. After cooling, the suspension is mixed with water (20 ml) and stirred at room temperature for a further 4 h. The precipitate is filtered off with suction and washed with benzene (10 ml). The organic phase of the filtrate is separated off, dried with magnesium sulfate and concentrated. The residue is purified by column chromatography on silica gel (mobile phase: cyclohexane/ethyl acetate 9:1). 1.83 g (82% of theory) of the title compound are obtained as a colorless oil.

$^1$H-NMR (300 MHz, DMSO-d$_6$): δ=2.31 (s, 3H), 7.08 (s, 1H), 7.89 (d, 2H), 8.05 (d, 2H).

Stage 42b):

3-Amino-1-[4-(trifluoromethyl)phenyl]but-2-en-1-one

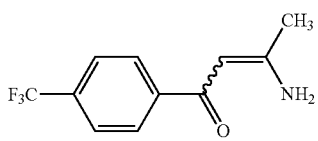

3-Methyl-5-[4-(trifluoromethyl)phenyl]isoxazole (1.8 g, 7.92 mmol) is introduced into 20 ml of ethanol, platinum(IV) oxide catalyst (180 mg) is added, and the mixture is then hydrogenated under atmospheric pressure hydrogen for 12 h. The catalyst is filtered off, and the filtrate is concentrated. 1.72 g (94% of theory) of the title compound are obtained as a white solid.

LC-MS (Method 1): $R_t$=2.69 min; [M+H]$^+$=230.

Stage 42c):

Ethyl 2,6-dimethyl-5-[4-(trifluoromethyl)benzoyl]-4-(2-methyl-4-oxo-4H-chromen-8-yl)-1,4-dihydropyridine-3-carboxylate

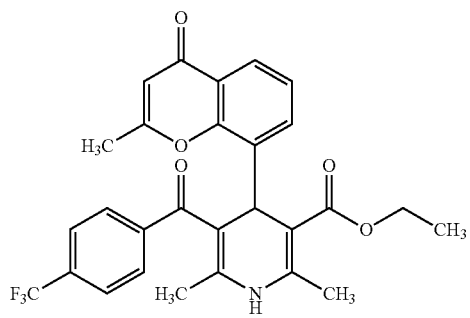

164 mg (0.87 mmol) of 2-methyl-4-oxo-4H-chromene-8-carbaldehyde are dissolved with 113 mg (0.87 mmol) of ethyl 3-oxobutanoate, 200 mg (0.87 mmol) of 3-amino-1-[4-(trifluoromethyl)phenyl]but-2-en-1-one and 5 μl (0.087 mmol) of acetic acid in 8 ml of 2-propanol and heated under reflux under argon for 30 h. The solvent is removed in vacuo, and the residue is purified by preparative HPLC. 59 mg (13% of theory) of the title compound are obtained as a yellow solid.

LC-MS (Method 3): $R_t$=2.47 min; [M+H]$^+$=512

$^1$H-NMR (300 MHz, DMSO-$d_6$): δ=0.91 (t, 3H), 1.80 (s, 3H), 2.06 (s, 3H), 2.36 (s, 3H), 3.87 (q, 2H), 5.52 (s, 1H), 6.13 (s, 1H), 7.33 (t, 1H), 7.48 (dd, 1H), 7.59 (t, 2H), 7.79 (m, 3H), 9.12 (s, 1H).

Example 43

Propyl 2,6-dimethyl-5-[4-(trifluoromethyl)benzoyl]-4-(2-methyl-4-oxo-4H-chromen-8-yl)-1,4-dihydro-pyridine-3-carboxylate

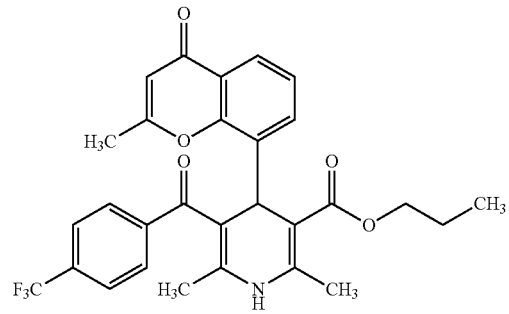

164 mg (0.87 mmol) of 2-methyl-4-oxo-4H-chromene-8-carbaldehyde are dissolved with 125 mg (0.87 mmol) of n-propyl 3-oxobutanoate, 200 mg (0.87 mmol) of 3-amino-1-[4-(trifluoromethyl)phenyl]but-2-en-1-one and 5 μl (0.087 mmol) of acetic acid in 8 ml of 2-propanol and heated under reflux under argon for 30 h. The solvent is removed in vacuo, and the residue is purified by preparative HPLC. 60 mg (13% of theory) of the title compound are obtained as a yellow solid.

LC-MS (Method 1): $R_t$=2.41 min; [M+H]$^+$=526

$^1$H-NMR (300 MHz, DMSO-$d_6$): δ=0.57 (t, 3H), 1.31 (m, 2H), 1.81 (s, 3H), 2.02 (s, 3H), 2.39 (s, 3H), 3.80 (t, 2H), 5.53 (s, 1H), 6.13 (s, 1H), 7.33 (t, 1H), 7.45 (dd, 1H), 7.62 (t, 2H), 7.78 (dd, 1H), 7.80 (d, 2H), 9.14 (s, 1H).

Example 44

Ethyl 2,6-dimethyl-5-[4-(tert-butyl)benzoyl]-4-(2-methyl-4-oxo-4H-chromen-8-yl)-1,4-dihydro-pyridine-3-carboxylate

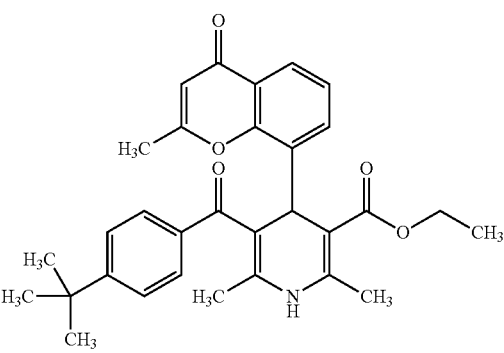

Stage 44a):

3-Methyl-5-[4-(tert-butyl)phenyl]isoxazole

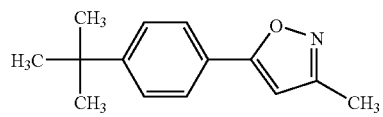

4.57 ml (42.12 mmol) of phenyl isocyanate are added dropwise at room temperature to a solution of 5 g (31.59 mmol) of 1-ethynyl-4-(tert-butyl)benzene, 0.75 ml (10.53 mmol) of nitroethane and 0.29 ml (2.10 mmol) of triethylamine in 100 ml of benzene. The reaction mixture is then stirred under reflux for 12 h. After cooling, the suspension is mixed with water (50 ml) and stirred at room temperature for a further 4 h. The precipitate is filtered off with suction and washed with benzene (10 ml). The organic phase of the filtrate is separated off, dried with magnesium sulfate and concentrated. The residue is purified by column chromatography on silica gel (mobile phase: cyclohexane/ethyl acetate 9:1). 989 mg (14% of theory) of the title compound are obtained as a colorless oil.

$^1$H-NMR (300 MHz, DMSO-d$_6$): δ=1.30 (s, 9H), 2.27 (s, 3H), 6.81 (s, 1H), 7.54 (d, 2H), 7.74 (d, 2H).

Stage 44b):

3-Amino-1-[4-(tert-butyl)phenyl]but-2-en-1-one

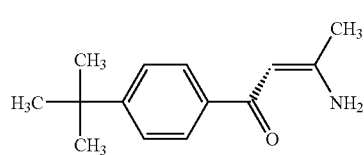

3-Methyl-5-[4-(tert-butyl)phenyl]isoxazole (900 mg, 4.18 mmol) is introduced into 20 ml of ethanol, platinum(IV) oxide catalyst (90 mg) is added and the mixture is then hydrogenated under atmospheric pressure hydrogen for 12 h. The catalyst is filtered off and the filtrate is concentrated. 897 mg (99% of theory) of the title compound are obtained as a white solid.

LC-MS (Method 3): R$_t$=2.76 min; [M+H]$^+$=218.

Stage 44c):

Ethyl 2,6-dimethyl-5-[4-(tert-butyl)benzoyl]-4-(2-methyl-4-oxo-4H-chromen-8-yl)-1,4-dihydro-pyridine-3-carboxylate

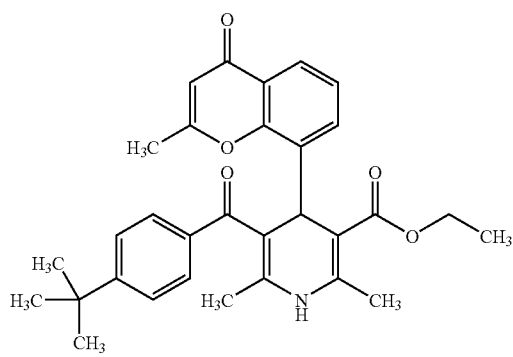

100 mg (0.53 mmol) of 2-methyl-4-oxo-4H-chromene-8-carbaldehyde are dissolved with 69 mg (0.53 mmol) of ethyl 3-oxobutanoate, 115 mg (0.53 mmol) of 3-amino-1-[4-(tert-butyl)phenyl]but-2-en-1-one and 5 μl (0.053 mmol) of acetic acid in 8 ml of 2-propanol and heated under reflux under argon for 30 h. The solvent is removed in vacuo, and the residue is purified by preparative HPLC. 169 mg (64% of theory) of the title compound are obtained as a yellow solid.

LC-MS (Method 3): R$_t$=2.65 min; [M+H]$^+$=500

$^1$H-NMR (300 MHz, DMSO-d$_6$): δ=0.88 (t, 3H), 1.27 (s, 9H), 1.74 (s, 3H), 1.97 (s, 3H), 2.38 (s, 3H), 3.84 (m, 2H), 5.58 (s, 1H), 6.10 (s, 1H), 7.33 (t, 1H), 7.44 (s, 4H), 7.47 (dd, 1H), 7.76 (dd, 1H), 8.89 (s, 1H).

Example 45

Propyl 2,6-dimethyl-5-[4-(tert-butyl)benzoyl]-4-(2-methyl-4-oxo-4H-chromen-8-yl)-1,4-dihydro-pyridine-3-carboxylate

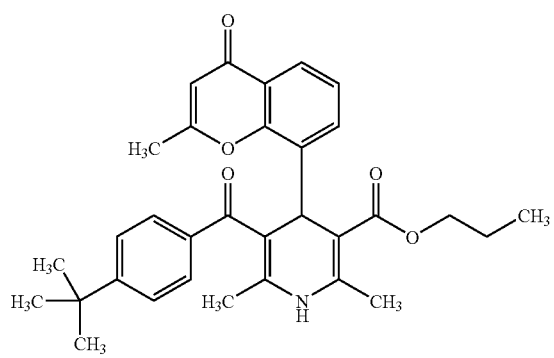

100 mg (0.53 mmol) of 2-methyl-4-oxo-4H-chromene-8-carbaldehyde are dissolved with 76 mg (0.53 mmol) of n-propyl 3-oxobutanoate, 115 mg (0.53 mmol) of 3-amino-1-[4-(tert-butyl)phenyl]but-2-en-1-one and 5 μl (0.053 mmol) of acetic acid in 8 ml of 2-propanol and heated under reflux under argon for 30 h. The solvent is removed in vacuo, and the residue is purified by preparative HPLC. 170 mg (62% of theory) of the title compound are obtained as a yellow solid.

LC-MS (Method 2): R$_t$=2.83 min; [M+H]$^+$=514

$^1$H-NMR (300 MHz, DMSO-d$_6$): δ=0.57 (t, 3H), 1.27 (m+s, 11H), 1.75 (s, 3H), 1.92 (s, 3H), 2.41 (s, 3H), 3.77 (m, 2H), 5.60 (s, 1H), 6.08 (s, 1H), 7.33 (t, 1H), 7.46 (m, 5H), 7.76 (dd, 1H), 8.92 (s, 1H).

Example 46

2,2,2-Trifluoroethyl 5-acetyl-2,6-dimethyl-4-(2-methyl-4-oxo-4H-chromen-8-yl)-1,4-dihydro-pyridine-3-carboxylate

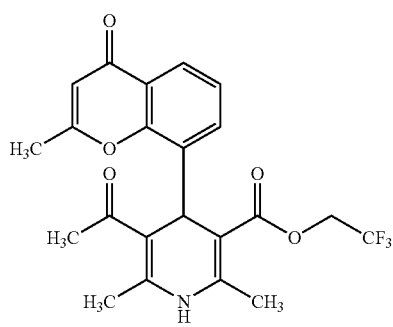

Stage 46a):

2,2,2-Trifluoroethyl 3-aminobut-2-enoate

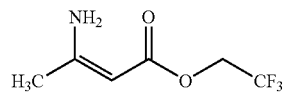

5 g (50 mmol) of 2,2,2-trifluoroethanol are dissolved in 30 ml of THF, and 505 mg (5 mmol) of triethylamine are added. Then 5.04 g (60 mmol) of diketene in 10 ml of THF are added dropwise. The reaction mixture is then heated to reflux for 4 h. Thereafter 7.7 g (100 mmol) of ammonium acetate, 2.8 ml (50 mmol) of acetic acid and 10 g of 4 Å molecular sieves are added, and the mixture is heated at 110° C. for 5 h. After cooling to room temperature, the reaction mixture is mixed with water and extracted with ethyl acetate. After washing with water and saturated sodium chloride solution, the organic phase is dried over magnesium sulfate. The solvent is removed in vacuo, and the residue is purified by column chromatography on silica gel (mobile phase: dichloromethane/methanol 95:5). The resulting product (8 g, 77% purity, 67% of theory) is employed without further purification in the next stage.

GC-MS (Method 6): $R_t$=3.98 min; $[M+H]^+$=183.

Stage 46b):

2,2,2-Trifluoroethyl 5-acetyl-2,6-dimethyl-4-(2-methyl-4-oxo-4H-chromen-8-yl)-1,4-dihydro-pyridine-3-carboxylate

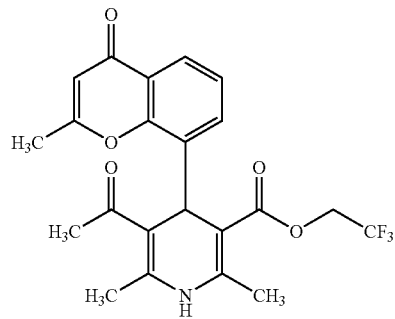

100 mg (0.53 mmol) of 2-methyl-4-oxo-4H-chromene-8-carbaldehyde are dissolved with 93.1 mg (0.93 mmol) of 2,4-pentanedione, 97 mg (0.53 mmol) of 2,2,2-trifluoroethyl 3-aminobut-2-enoate and 32 µl (0.55 mmol) of acetic acid in 5 ml of isopropanol and heated under reflux under argon for 10 h. The solvent is then removed in vacuo, and the residue is purified by column chromatography on silica gel (mobile phase: dichloromethane/methanol 95:5). 28 mg (12% of theory) of the title compound are obtained as a yellow solid.

$^1$H-NMR (300 MHz, DMSO-$d_6$): δ=2.18 (s, 3H), 2.22 (s, 3H), 2.32 (s, 3H), 2.38 (s, 3H), 4.59 (m, 2H), 5.45 (s, 1H), 6.21 (s, 1H), 7.31 (t, 1H), 7.55 (dd, 1H), 7.80 (dd, 1H), 9.22 (s, 1H).

B. ASSESSMENT OF THE PHARMACOLOGICAL ACTIVITY

Abbreviations
DMEM Dulbecco's modified Eagle medium
DNA deoxyribonucleic acid
FCS fetal calf serum
HEPES 4-(2-hydroxyethyl)-1-piperazineethanesulfonic acid
PCR polymerase chain reaction
Tris tris-(hydroxymethyl)methylamine The advantageous pharmacological properties of the compounds of the invention can be shown in the following assays:

1. Cellular In Vitro Assay to Determine the Inhibitory MR Activity and MR Selectivity Compared with Other Steroid Hormone Receptors Antagonists of the human mineralocorticoid receptor (MR) are identified, and the activity of the compounds described herein is quantified with the aid of a recombinant cell line. The cell is originally derived from a hamster ovary epithelial cell (Chinese Hamster Ovary, CHO K1, ATCC: American Type Culture Collection, VA 20108, USA).

An established chimera system in which the ligand-binding domains of human steroid hormone receptors are fused to the DNA-binding domain of the yeast transcription factor GAL4 is used in this CHO K1 cell line. The GAL4-steroid hormone receptor chimeras produced in this way are cotransfected and stably expressed with a reporter construct in the CHO cells.

Clonings:

To generate the GAL4-steroid hormone receptor chimeras, the GAL4 DNA binding domain (amino acids 1-147) from the vector pFC2-dbd (from Stratagene) is cloned with the PCR-amplified ligand-binding domains of the mineralocorticoid receptor (MR, amino acids 734-985), of the glucocorticoid receptor (GR, amino acids 443-777), of the progesterone receptor (PR, amino acids 680-933) and of the androgen receptor (AR, amino acids 667-919) into the vector pIRES2 (from Clontech). The reporter construct, which comprises five copies of the GAL4 binding site upstream of a thymidine kinase promoter, leads to expression of firefly-luciferase (*Photinus pyralis*) after activation and binding of the GAL4-steroid hormone receptor chimeras by the respective specific agonists aldosterone (MR), dexamethasone (GR), progesterone (PR) and dihydrotestosterone (AR).

Assay Procedure:

The MR, GR, PR and AR cells are plated out in medium (Optimem, 2.5% FCS, 2 mM glutamine, 10 mM HEPES) in 96- (or 384- or 1536-) well microtiter plates on the day before the assay and are kept in a cell incubator (96% humidity, 5% v/v $CO_2$, 37° C.). On the day of the assay, the substances to be tested are taken up in the abovementioned medium and added to the cells. About 10 to 30 minutes after addition of the test substances, the respective specific agonists of the steroid hormone receptors are added. After a further incubation time of 5 to 6 hours, the luciferase activity is measured with the aid of a video camera. The measured relative light units as a function of the substance concentration result in a sigmoidal stimulation curve. The $IC_{50}$ values are calculated with the aid of the GraphPad PRISM computer program (Version 3.02).

Table A shows the $IC_{50}$ values (MR) of representative exemplary compounds:

TABLE A

| Example No. | MR $IC_{50}$ [nM] |
|---|---|
| 1 (Racemate) | 75 |
| 1 (Enantiomer 2) | 43 |
| 2 | 22 |
| 3 | 39 |
| 4 | 235 |
| 8 | 19 |
| 11 | 74 |
| 14 | 104 |
| 34 | 18 |
| 37 | 27 |

2. In Vitro Assay to Determine Possible Binding Activity to the L-Type Calcium Channel Membrane preparations of the cerebral cortex of Wistar rats serve as starting material for a radioactive binding assay which is described in detail in the literature as standard assay [Ehlert, F. J., Roeske, W. R., Itoga E., Yamamura, H. I., *Life Sci.* 30, 2191-2202 (1982); Gould, R. J., Murphy, K. M. M., Snyder, S. H., *Proc. Natl. Acad. Sci. U.S.A.* 79, 3656-3660] and is used in contract investigations by commercial service suppliers (e.g. MDS Pharma Services). In this binding assay, serial dilutions of the test compounds in DMSO are incubated with the membrane preparations and the tritium-labeled ligand nitrendipine (0.1 nM) in a 50 mM TrisHCl buffer, pH 7.7, at 25° C. typically for 90 minutes, and the specific binding of the test compounds is determined by quantifying the specifically displaced, radiolabelled ligand. $IC_{50}$ values are determined by a nonlinear regression analysis.

The $IC_{50}$ determined in this L-type calcium channel binding assay for a conventional calcium antagonist of the dihydropyridine type such as, for example, nitrendipine is 0.3 nM, whereas the $IC_{50}$ values for investigated examples of the compounds of the invention described herein are of the order of 0.8 to 5 µM and thus the affinity shown for the L-type calcium channel is reduced by a factor of at least 1000. Compounds with such a low residual binding affinity for the L-type calcium channel no longer show pronounced hemodynamic effects mediated by the L-type calcium channel in vivo.

3. In Vitro Assay for Functional Characterization of Possible Calcium Channel-Agonistic or -Antagonistic Effects of Test Compounds: Potassium Chloride-Induced Stimulation of the Isolated Rabbit Aorta The freshly isolated thoraxic aorta of male New Zealand white rabbits is removed and cleaned of surrounding tissue. Then aortic rings with a length of 2 mm are put under an initial tension of 4 g in 10 ml organ parts with Krebs-Henseleit solution heated to 37° C. Contractions are induced by 40 mM KCl (submaximal contraction) and 15 mM KCl (minimal contraction) four times at an interval of 45 minutes in order to train the vessels and generate a stable resting tension. Each contraction is followed by a series of eleven rinsing cycles and a resting period of 30 minutes with previous retensioning. After the four pre-runs, the test substances are added to the organ baths in each case at the start of the resting period without further retensioning. The concentration of the test substances is increased by a factor of 10 for each of the four following contractions. To calculate the effect, the difference between the baseline tension and the value for the fourth pre-run contraction is set equal to 100%, and the following contraction peaks are related to this value. This experimental procedure makes it possible to differentiate calcium-agonistic (slight increase at the submaximal contraction, greater increase at the minimal contraction) and calcium-antagonistic effect of the substance (reduction at the submaximal contraction, greater reduction at the minimal contraction).

The $IC_{50}$ measured for a conventional calcium antagonist of the dihydropyridine type such as, for example, nifedipine in this functional assay on the isolated organ is from 0.1 nM to 0.4 nM, whereas the $IC_{50}$ values for investigated examples of the compounds of the invention described herein are of the order of 4 to 25 µM, and thus the affinity shown for the L-type calcium channel is reduced by a factor of at least 10 000. Compounds with such a low residual binding affinity for the L-type calcium channel no longer show pronounced hemodynamic effects mediated by the L-type calcium channel in vivo.

4. In Vivo Assay for Detecting the Cardiovascular Effect: Diuresis Investigations on Conscious Rats in Metabolism Cages Wistar rates (bodyweight 250-350 g) are kept with free access to feed (Altromin) and drinking water. From about 72 hours before the start of the test, the animals receive instead of the normal feed exclusively salt-reduced feed with a sodium chloride content of 0.02% (ssniff R/M–H, 10 mm with 0.02% Na, S0602-E081, ssniff Spezialdiäten GmbH, D-59494 Soest). During the test, the animals are housed singly in metabolism cages suitable for rats of this weight class (from Tecniplast Deutschland GmbH, D-82383 Hohenpeißenberg) with free access to salt-reduced feed and drinking water for about 24 hours. At the start of the test, the substance to be tested is administered into the stomach by means of gavage in a volume of 0.5 ml/kg of bodyweight of a suitable solvent. Control animals receive only solvent. Controls and substance tests are carried out in parallel on the same day. Control groups and substance-dose groups each consist of 3 to 6 animals. During the test, the urine excreted by the animals is continuously collected in a receiver on the base of the cage. The urine volume per unit time is determined separately for each animal, and the concentration of the sodium and potassium ions excreted in the urine is measured by standard methods of flame photometry. The sodium/potassium ratio is calculated from the measurements as a measure of the effect of the substance. The measurement intervals are typically the period up to 8 hours after the start of the test (day interval) and the period from 8 to 24 hours after the start of the test (night interval). In a modified test design, the urine is collected and measured at intervals of two hours during the day interval. In order to obtain a sufficient amount of urine for this purpose, the animals receive a defined amount of water by gavage at the start of the test and then at intervals of two hours.

C. EXEMPLARY EMBODIMENTS OF PHARMACEUTICAL COMPOSITIONS

The compounds of the invention can be converted into pharmaceutical preparations in the following ways:
Tablet:
Composition:

100 mg of the compound of the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.
Production:

The mixture of compound of the invention, lactose and starch is granulated with a 5% strength solution (m/m) of the PVP in water. The granules are mixed with the magnesium stearate for 5 minutes after drying. This mixture is compressed with a conventional tablet press (see above for format of the tablet). A guideline compressive force for the compression is 15 kN.
Suspension which can be Administered Orally:
Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.
Production:

The Rhodigel is suspended in ethanol, and the compound of the invention is added to the suspension. The water is added while stirring. The mixture is stirred for about 6 h until the swelling of the Rhodigel is complete.

Solution which can be Administered Orally:
Composition:

500 mg of the compound of the invention, 2.5 g of polysorbate and 97 g of polyethylene glycol 400. 20 g of oral solution correspond to a single dose of 100 mg of the compound according to the invention.

Production:

The compound of the invention is suspended in the mixture of polyethylene glycol and polysorbate with stirring. The stirring process is continued until the compound according to the invention has completely dissolved.

i.v. Solution:

The compound of the invention is dissolved in a concentration below the saturation solubility in a physiologically tolerated solvent (e.g. isotonic saline solution, 5% glucose solution and/or 30% PEG 400 solution). The solution is sterilized by filtration and used to fill sterile and pyrogen-free injection containers.

The invention claimed is:

1. A compound of the formula (I)

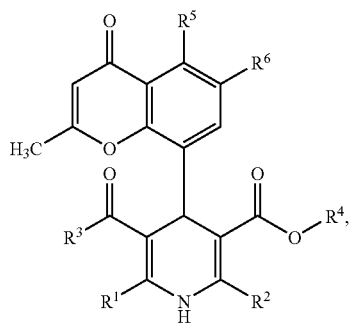

in which
- $R^1$ and $R^2$ are identical or different and are independently of one another $(C_1-C_4)$-alkyl, trifluoromethyl, cyclopropyl or cyclobutyl,
- $R^3$ is $(C_3-C_7)$-cycloalkyl, is $(C_1-C_6)$-alkyl which may be substituted by $(C_3-C_7)$-cycloalkyl or once to three times by fluorine, or is phenyl which may be substituted by halogen, cyano, $(C_1-C_4)$-alkyl, trifluoromethyl, $(C_1-C_4)$-alkoxy or trifluoromethoxy,
- $R^4$ is $(C_3-C_7)$-cycloalkyl or is $(C_1-C_6)$-alkyl which may be substituted by $(C_3-C_7)$-cycloalkyl or once to three times by fluorine,
- $R^5$ is hydrogen, halogen, cyano, nitro, trifluoromethyl, $(C_1-C_4)$-alkyl or $(C_1-C_4)$-alkoxy,
and
- $R^6$ is hydrogen or fluorine, or a salt, solvate, or solvate of a salt thereof.

2. The compound of the formula (I) as claimed in claim 1, in which
- $R^1$ and $R^2$ are identical or different and are methyl or trifluoromethyl,
- $R^3$ is $(C_5-C_7)$-cycloalkyl, is $(C_1-C_6)$-alkyl which may be substituted by $(C_3-C_5)$-cycloalkyl or once to three times by fluorine, or is phenyl which may be substituted by fluorine, chlorine, trifluoromethyl, methyl, isopropyl, tert-butyl or methoxy,
- $R^4$ is $(C_3-C_5)$-cycloalkyl or is $(C_1-C_4)$-alkyl which may be substituted by $(C_3-C_5)$-cycloalkyl or once to three times by fluorine,
- $R^5$ is hydrogen, fluorine, chlorine, nitro or methyl,
and
- $R^6$ is hydrogen or fluorine, or a salt, solvate, or solvate of a salt thereof.

3. The compound of the formula (I) as claimed in claim 1, in which
- $R^1$ is methyl or trifluoromethyl,
- $R^2$ is methyl,
- $R^3$ is methyl, trifluoromethyl, isobutyl, isopentyl, cyclobutylmethyl, cyclopentylmethyl, 2-(cyclopropyl)ethyl, 2-(cyclobutyl)ethyl, 2-(cyclopentyl)ethyl or is phenyl which may be substituted in the para position by fluorine, trifluoromethyl, methyl or methoxy,
- $R^4$ is methyl, ethyl, 2,2,2-trifluoroethyl, n-propyl, isopropyl, tert-butyl, cyclobutyl, cyclopentyl, cyclopropylmethyl or cyclobutylmethyl,
- $R^5$ is hydrogen, fluorine or chlorine,
and
- $R^6$ is hydrogen, or a salt, solvate, or solvate of a salt thereof.

4. A process for preparing compounds of the formula (I) as defined in claim 1, characterized in that a compound of the formula (II)

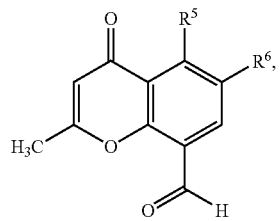

in which $R^5$ and $R^6$ each have the meanings in claim 1 either

[A] is reacted in a one-stage process (one-pot reaction) with a compound of the formula (III)

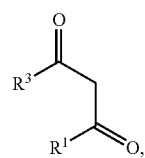

in which $R^1$ and $R^3$ each have the meanings in claim 1, and a compound of the formula (IV)

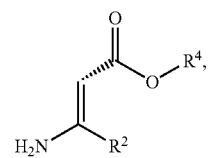

in which $R^2$ and $R^4$ each have the meanings in claim 1, or

[B] is reacted in a one-stage process (one-pot reaction) with a compound of the formula (V)

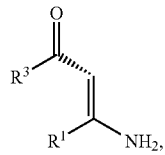

(V)

in which $R^1$ and $R^3$ each have the meanings in claim 1, and a compound of the formula (VI)

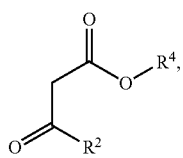

(VI)

in which $R^2$ and $R^4$ each have the meanings in claim 1, or

[C] is converted in a two-stage process firstly with a compound of the formula (III) into a compound of the formula (VII)

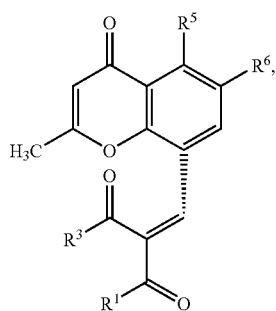

(VII)

in which $R^1$, $R^3$, $R^5$ and $R^6$ each have the meanings in claim 1, and the latter is then reacted in a second step with a compound of the formula (IV), or

[D] is converted in a two-stage process firstly with a compound of the formula (VI) into a compound of the formula (VIII)

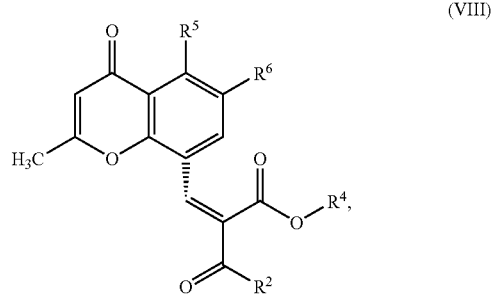

(VIII)

in which $R^2$, $R^4$, $R^5$ and $R^6$ each have the meanings in claim 1, and the latter is then reacted in a second step with a compound of the formula (V).

5. A pharmaceutical composition comprising a compound of the formula (I) as defined in claim 1 in combination with an inert, non-toxic, pharmaceutically suitable excipient.

6. A pharmaceutical composition comprising a compound of the formula (I) as defined in claim 1 in combination with a further active ingredient selected from the group consisting of ACE inhibitors, renin inhibitors, angiotensin II receptor antagonists, beta blockers, acetyl salicylic acid, diuretics, potassium supplements, calcium antagonists, statins, digitalis (digoxin) derivatives, calcium sensitizers, nitrates, anticoagulants, antiarrhythmics, vasodilators, and thrombolytics.

* * * * *